US009658471B2

(12) United States Patent
Ando et al.

(10) Patent No.: US 9,658,471 B2
(45) Date of Patent: May 23, 2017

(54) MULTIFOCAL OPHTHALMIC LENS HAVING A FOCAL POINT FORMATION REGION AND A CANCELLATION REGION AND MANUFACTURING METHOD THEREOF

(71) Applicant: MENICON CO., LTD., Nagoya-shi, Aichi (JP)

(72) Inventors: Ichiro Ando, Kasugai (JP); Hiroaki Suzuki, Kasugai (JP); Atsushi Kobayashi, Kasugai (JP)

(73) Assignee: MENICON CO., LTD., Nagoya-shi (JP)

( * ) Notice: Subject to any disclaimer, the term of this patent is extended or adjusted under 35 U.S.C. 154(b) by 9 days.

(21) Appl. No.: 14/377,819

(22) PCT Filed: Feb. 6, 2013

(86) PCT No.: PCT/JP2013/000650
§ 371 (c)(1),
(2) Date: Aug. 8, 2014

(87) PCT Pub. No.: WO2013/118499
PCT Pub. Date: Aug. 15, 2013

(65) Prior Publication Data
US 2015/0022775 A1    Jan. 22, 2015

(30) Foreign Application Priority Data

Feb. 9, 2012   (JP) .................. 2012-025818

(51) Int. Cl.
*G02C 7/02*      (2006.01)
*G02C 7/04*      (2006.01)
*A61F 2/16*      (2006.01)

(52) U.S. Cl.
CPC ............ *G02C 7/049* (2013.01); *A61F 2/1618* (2013.01); *A61F 2/1654* (2013.01); *G02C 7/028* (2013.01);
(Continued)

(58) Field of Classification Search
CPC ............................................. G02C 7/00–7/165
(Continued)

(56) References Cited

U.S. PATENT DOCUMENTS 4,881,805 A * 11/1989 Cohen .................. G02B 5/1876
                                                351/159.42
5,120,120 A *  6/1992 Cohen .................. G02B 5/1895
                                                264/1.8

(Continued)

FOREIGN PATENT DOCUMENTS

EP    1072906 A2    1/2001
EP    2378319 A1    10/2011
(Continued)

OTHER PUBLICATIONS

International Search Report issued in International Patent Application No. PCT/JP2013/000650 mailed May 21, 2013.
(Continued)

*Primary Examiner* — Scott J Sugarman
*Assistant Examiner* — Henry Duong
(74) *Attorney, Agent, or Firm* — Oliff PLC

(57) ABSTRACT

In order to reduce halos that occur in multifocal ophthalmic lenses, the mechanism of the phenomenon was elucidated and a solution was found based on the results. Thus provided are a multifocal ophthalmic lens having a structure and a manufacturing method for the same which can effectively reduce halos. A multifocal ophthalmic lens having a focal point formation region provided to an optical portion of a lens, which forms at least two focal points, wherein a
(Continued)

cancellation region is provided to the optical portion, the cancellation region providing diffracted light of an amplitude distribution that reduces, on the image plane of the first focal point among the focal points, the amplitudes of light other than the light that forms the first focal point.

27 Claims, 45 Drawing Sheets
(6 of 45 Drawing Sheet(s) Filed in Color)

(52) U.S. Cl.
CPC ............ *G02C 7/041* (2013.01); *G02C 7/044* (2013.01); *A61F 2240/001* (2013.01); *G02C 2202/20* (2013.01)

(58) Field of Classification Search
USPC .............................................. 351/159.01–178
See application file for complete search history.

(56) References Cited

U.S. PATENT DOCUMENTS

| | | | |
|---|---|---|---|
| 5,121,980 A | 6/1992 | Cohen | |
| 5,699,142 A * | 12/1997 | Lee | .................. A61F 2/1618 351/159.11 |
| 6,158,862 A | 12/2000 | Patel et al. | |
| 6,260,966 B1 | 7/2001 | Sawano et al. | |
| 6,829,093 B1 | 12/2004 | Nakai | |
| 7,156,516 B2 * | 1/2007 | Morris | .................. A61F 2/1613 351/159.44 |
| 2008/0269885 A1 | 10/2008 | Simpson et al. | |
| 2008/0269890 A1 | 10/2008 | Simpson et al. | |
| 2009/0195748 A1 * | 8/2009 | Bandhauer | ............ A61F 2/1618 351/159.47 |
| 2010/0161048 A1 | 6/2010 | Schaper, Jr. | |
| 2011/0234974 A1 * | 9/2011 | Lawu | .................. G02B 5/1895 351/159.11 |
| 2011/0270390 A1 * | 11/2011 | Kobayashi | ............ A61F 2/1618 623/6.38 |
| 2011/0317124 A1 | 12/2011 | Weeber et al. | |

FOREIGN PATENT DOCUMENTS

| | | |
|---|---|---|
| JP | A-2000-511299 | 8/2000 |
| JP | A-2001-42112 | 2/2001 |
| JP | A-2007-181726 | 7/2007 |
| JP | A-2010-134282 | 6/2010 |
| JP | A-2010-158315 | 7/2010 |
| JP | A-2010-525884 | 7/2010 |
| JP | A-2010-525885 | 7/2010 |

OTHER PUBLICATIONS

Oct. 20, 2015 Search Report issued in European Application No. 13746957.3.

* cited by examiner

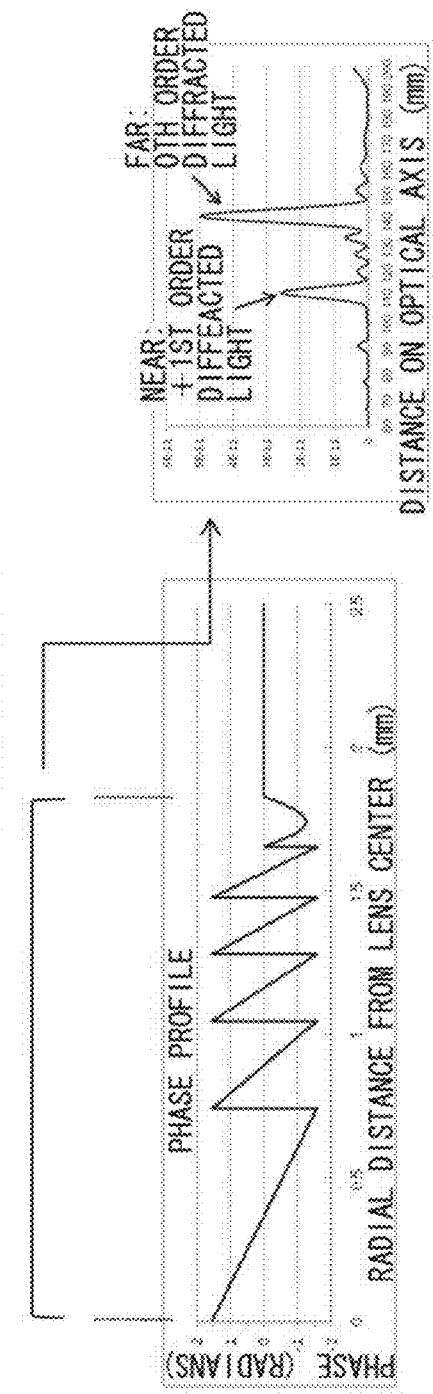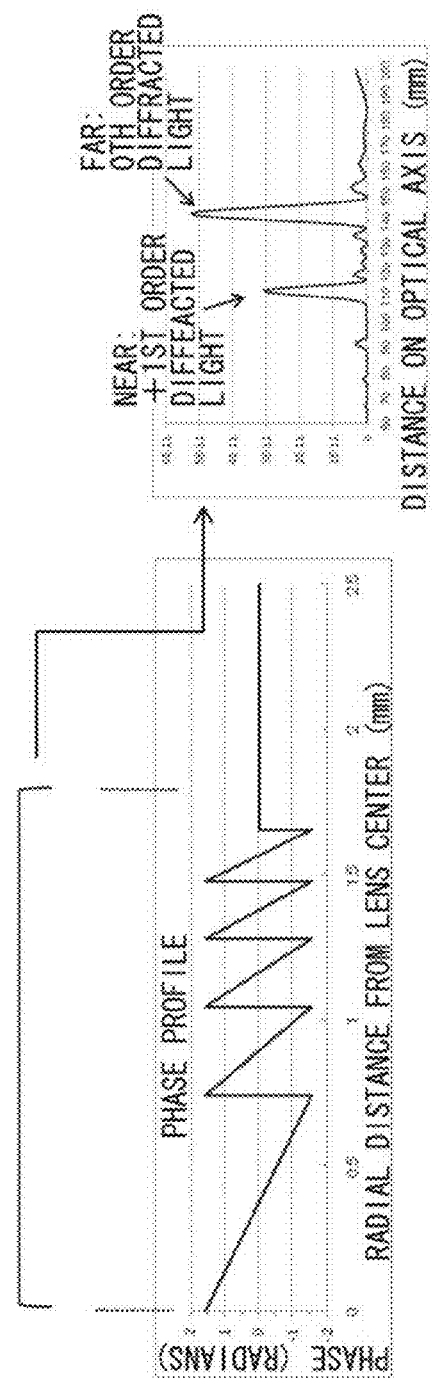

[5TH EMBODIMENT]

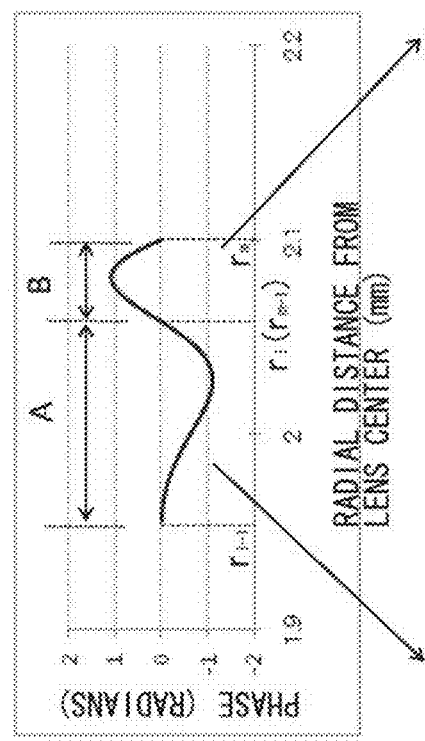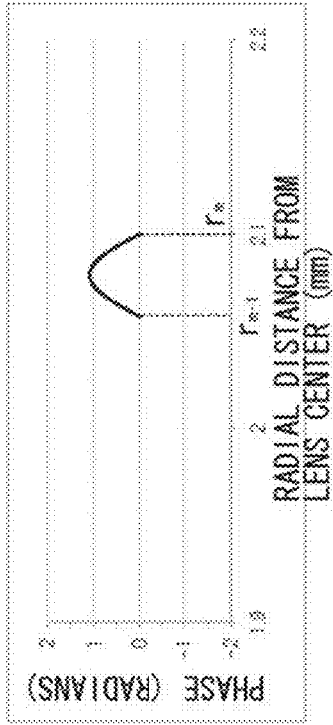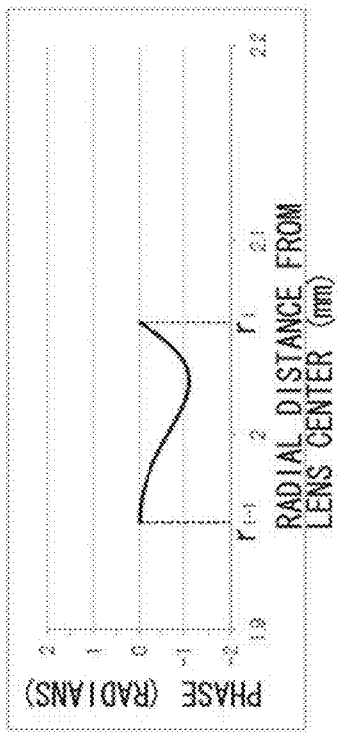
FIG.39A
FIG.39B
FIG.39C

[EXAMPLE OF ANOTHER ASPECT OF 10TH EMBODIMENT]

[14TH EMBODIMENT]

MULTIFOCAL OPHTHALMIC LENS HAVING A FOCAL POINT FORMATION REGION AND A CANCELLATION REGION AND MANUFACTURING METHOD THEREOF

TECHNICAL FIELD

This invention relates to an ophthalmic lens such as a contact lens and an intraocular lens used for the human eye that exert a correction effect and the like in the human optical system, especially to a multifocal ophthalmic lens with a novel diffraction structure, as well as a manufacturing method thereof.

BACKGROUND ART

Conventionally, ophthalmic lenses have been used as optical elements for vision correction in the human optical system and as alternative optical elements after crystalline lens extraction. Among them, contact lenses applied to the eye and intraocular lenses to be inserted therein have been used extensively because they provide a wide vision by being directly used for the human eye while reducing the uncomfortable feeling in seeing objects.

Meanwhile, there are increasing number of people in recent years who reached the presbyopic age and continue to wear contact lenses. Since such seniors who suffer from presbyopia have their focal functions deteriorated, they develop a symptom of hardly being able to focus on objects nearby. Therefore, presbyopia patients will need multifocal contact lenses that allow them to focus on nearby objects, too. Also, since patients who underwent a cataract surgery have their crystalline lens removed that used to adjust the vision, they still have symptoms resulting in difficulties in seeing nearby objects even if intraocular lenses are inserted in their eyes. It is becoming necessary for such intraocular lenses to have a multifocal function realized by multiple focal points. Thus, needs for multifocal lenses are increasingly growing in recent years reflecting our aging society.

As methods of producing such multifocal ophthalmic lenses, there have been known a refraction-type multifocal lens that forms multiple focal points based on the refraction principle and a diffraction-type multifocal lens that forms multiple focal points based on the diffraction principle. In the latter mentioned diffraction-type multifocal lens, the optical part of the lens is provided with a plurality of diffraction structures formed concentrically, and multiple focal points are formed by the effect of mutual interference between light waves that pass through the multiple diffraction structures (zones). Therefore, such lenses have an advantage of being able to set a higher lens power while minimizing the lens thickness as compared to refraction-type lenses that generate focal points by the refraction effect of light waves at the refracting interface, which is a boundary of different refractive indices.

Generally speaking, the diffraction-type multifocal lens has a diffraction structure where the pitch of diffraction zones gradually gets smaller as it moves from the center toward the periphery according to certain rules called 'Fresnel pitch,' and the 0th order diffracted light and first-order diffracted light generated from the structure are used to produce multiple focal points. Usually, the 0th order diffracted light focal points for far vision while the first-order diffracted light focal points for near vision. By providing such a distribution of diffracted light, a bifocal lens having focal points for far and near vision can be produced.

However, the diffraction-type ophthalmic lens has a problem of easily generating band-like or ring-like circles of light around the light source when the light source is viewed by an eye from a distance at night. This circle of light usually called 'halo' tends to appear around a point light source such as a street light or a motor vehicle headlight or the like in a distance, which causes a problem of deteriorated visibility at night using the ophthalmic lens. The halo is one of the phenomena reflecting the imaging characteristics of multifocal lenses, especially those called the simultaneous perception-type, and the cause of the halo formation can be explained as follows:

In case of an ideal monofocal lens with no aberration, light from far distance passes through the lens and focuses an image at a given focal point position so as to intensify the amplitudes of light waves each other to the maximum extent (FIG. 43A). In that process, the image plane intensity distribution at the focal point position shows a simple pattern of only a main peak at the center with very small side lobes defined by the Airy radius existing around it (FIGS. 43B, 43C). FIG. 43C is a magnified view of FIG. 43B. Therefore, when a light source is viewed from a distance, an image is formed with no halo that reflects such intensity distribution (FIG. 43D).

Meanwhile, a diffraction-type multifocal lens having two focal points for far and near vision is designed in such a way that the light from a distance produces an image at the far focal point position so as to maximize the amplitude of light waves each other, while intensifying the amplitude of each other at the near focal point position, too. Light from a distance forms the main peak centered around the image plane at the far focal point, whereas light waves intensified each other at the near focal point position diverge thereafter to reach the image plane at the far focal point (FIG. 44A). At a first glance of FIG. 44B, there seems to be only one main peak on the image plane at the far focal point, but as shown in the magnified view of FIG. 44C, a group of small peaks can be recognized. As mentioned above, these peaks are formed by the light components focusing at the near focal point to be mixed in the far focal plane as a kind of stray light. Thus the intensity of the group of small peaks is very small compared to that of the main peak, but even light with the smallest intensity can be conspicuous in the night environment with dark background, and further, the image can be easily detected by the retina with high visual sensitivity to be perceived as a halo (FIG. 44D).

Such formation of a group of small peaks occurs as a phenomenon of light waves, and as shown in FIG. 45A, the light passing through each diffraction zone of a diffraction-type multifocal lens exhibits an amplitude distribution reflecting the characteristics of each zone on the far focal point image plane. For example, the light passing through each of the zones A, B and C in FIG. 45A forms the amplitude distribution shown in FIG. 45B. Then, a composite of amplitudes of the light beams from each zone determines the overall amplitude distribution on the far focal point image plane (FIG. 45C). The conjugate absolute values of these amplitudes become the intensity of light (FIG. 45D) to be perceived by the eye as the group of small peaks described above. Therefore, in order to reduce the intensity of the group of small peaks, it is necessary to restrict the amplitudes or the expanse thereof on the image plane in the underlying amplitude distribution, and controlling such amplitude distribution leads to the halo reduction.

Some other background arts propose a solution to the halo problem addressed with regard to the diffraction-type multifocal ophthalmic lens. Japanese Domestic Publication of International Patent Application No. JP-A-2000-511299 (Patent Document 1), for example, discloses a method of smoothly reducing the height of the diffraction zone toward the periphery in a diffraction structure composed of one form of diffraction zone called 'echelette' in order to reduce the halo as well as a function that defines such changes in height. This method tries to reduce the amount of energy distributed to the near focal point as it moves toward the periphery and reduce the halo as a result. However, in the background art mentioned above, the amount of energy distributed to the near focal point needs to be substantially lowered in order to reduce the halo to an imperceptible level, in which case there is a problem that the visibility of near objects is significantly deteriorated. Also, because of the changes in energy ratio between far and near focal points following the changes in pupil size, there is a problem of difficulties in providing a constant visibility under a condition of changing illuminance.

Also, Japanese Unexamined Patent Publication No. JP-A-2007-181726 (Patent Document 2) discloses a multifocal ophthalmic lens that blocks or reduces the transmission of blue light and/or near-UV light in order to eliminate glare and halos. In such background art, scattering of light is considered to be the cause of the glare and halos, which can presumably be reduced by preventing the transmission of short-wave light subject to scattering. However, since the halo is attributable more to the intrinsic behavior of light for forming a near focal point rather than the scattering of light, the background art does not produce a basic solution to the problem even though some ancillary effects can be expected. Thus, under the current situation, there is no such thing like a diffraction-type multifocal ophthalmic lens with restricted halo generation and a good balance between far and near vision.

BACKGROUND ART DOCUMENTS

Patent Documents

Patent Document 1: JP-A-2000-511299
Patent Document 2: JP-A-2007-181726

SUMMARY OF THE INVENTION

Problem the Invention Attempts to Solve

This invention offers a diffraction-type multifocal ophthalmic lens with a novel structure capable of reduce the halo effectively, which was found by the studies on the mechanism of halo formation in an attempt to reduce it and from a solution based on the study results, as well as a manufacturing method thereof.

Means for Solving the Problem

Aspects of the present invention designed to solve the above problems will be described below, but the terms and phrases used in the present invention are defined as follows:

'Amplitude function (distribution)' means a function (distribution) that mathematically describes the characteristics of light as waves, which is expressed specifically by Equation 1 below.

$$\text{Amplitude function} = \alpha e^{i\phi(x)} \quad \text{or} \quad \text{Amplitude function} = \alpha \cos\{\phi(x)\} \quad \text{[Equation 1]}$$

x: Variable
α: Constant

'Phase' expressed by $\phi(x)$ in Equation 1 above advances or delays the travel of light waves. In the present invention, phase is denoted by $\phi$ in the unit of radian. For example, one wavelength of light is expressed as $2\pi$ radian and a half wavelength as $\pi$ radian.

'Phase modulation' collectively means a structure or a method provided in a lens that causes a change in the phase of light incident thereon.

'Phase function' is a function that represents phase changes in the exponential or cosine function portion of Equation 1. In the present invention, the term is used mainly to express the lens's phase $\phi$ relative to the position r measured from the lens center in the radial direction and represented more specifically on the r-$\phi$ coordinate plane as shown in FIG. 46. Also, distribution of the phase within the entire frame of the phase modulation structure on the coordinate plane is called a 'phase profile.' When light is incident on the lens at $\phi=0$ relative to the r-axis datum line of $\phi=0$, it means the light emits from the lens without changing the phase. If $\phi$ takes a positive value relative to the datum line, the travel of light is delayed as much as the phase difference, whereas if $\phi$ takes a negative value, the travel of light is advanced as much. In an actual ophthalmic lens, the datum line (plane) is the refracting interface provided with no diffraction structure.

'Optical axis' means a rotationally symmetrical axis of a lens, which refers, in this case, to an axis that penetrates through the lens center projecting into the object space as well as into the image space.

'Image plane' means a plane perpendicular to the optical axis at a certain position in the image space where light incident to a lens emits therefrom.

'0th order focal point' means a focal point position of 0th order diffracted light. In the following paragraphs, the focal point positions of the first and subsequent order diffracted light will be referred to as a first-order focal point, a second-order focal point ... , and so forth.

'0th order focal point image plane' means an image plane at the focal point position of 0th order diffracted light.

The term 'orbicular zone' is used herein as a minimum unit in the diffraction structure. For example, a region where one blaze is formed is called an orbicular zone. It is also called a 'zone.'

'Blaze' refers to one form of phase function with the phase changing in a roof configuration. In the present invention, the basic blaze is the one shown in FIG. 47A wherein each peak and valley of the graph change linearly in each orbicular zone. The concept of blaze in the present invention also includes the one wherein the peaks and valleys are connected to change along a parabolic curve (FIG. 47B) or the one in a convex-concave (square wave) shape. It also includes the one shown in FIG. 47C wherein the peaks and valleys are connected to change in a sine curve as well as the ones wherein each peak and valley are connected to change within an interval with no extrema. In the present invention, the blaze of the $n^{th}$ zone is basically set as shown in FIG. 47A, unless otherwise specified, in such a way that the phase $\phi_n$ of the zone's outer radius $r_n$ and the phase $\phi_{n-1}$ of the inner radius $r_{n-1}$ become equal in the absolute values across the datum plane (line), that is, $|\phi_n|=|\phi_{n-1}|$. The phase function $\phi(r)$ of the blaze is expressed by Equation 2 below.

$$\phi(r) = \left(\frac{\phi_n - \phi_{n-1}}{r_n - r_{n-1}}\right) \times r + \left(\frac{\phi_{n-1} \times r_n - \phi_n \times r_{n-1}}{r_n - r_{n-1}}\right) \quad \text{[Equation 2]}$$

$\phi_n$: Phase at the position on the outer radius of the $n^{th}$ diffraction zone $\phi_{n-1}$: Phase at the position on the inner radius of the $n^{th}$ diffraction zone $r_n$: Outer radius of the $n^{th}$ diffraction zone
$r_{n-1}$: Inner radius of the $n^{th}$ diffraction zone
r: Distance from the lens center in the radial direction As to the phase shift, when a certain phase function $\phi(r)$ is shifted by $\tau$ in the $\phi$-axis direction relative to the datum line (plane) of the r-$\phi$ coordinate system, this $\tau$ is called a phase shift. Its relation with the phase function $\phi'(r)$ that is newly obtained by the shift $\tau$ is expressed as in Equation 3 below. The unit is radian.

$$\phi'(r) = \phi(r) + \tau \quad \text{[Equation 3]}$$

For example, assuming that the position of the blaze described above is shifted in the $\phi$-axis direction relative to the datum plane keeping the blazed step as it is, the relation between the new valley and peak $\phi'_n$, $\phi'_{n-1}$ formed by the shift and the original $\phi_n$, $\phi_{n-1}$ is expressed by Equation 4 below. This positional relation is shown in FIG. 48. In the present invention, the new function $\phi'(r)$ set up by introducing the phase shift $\tau$ can be used as one form of phase function.

$$\phi'_n = \phi_n + \tau$$

$$\phi'_{n-1} = \phi_{n-1} + \tau \quad \text{[Equation 4]}$$

'Phase constant' refers to a constant h defined by Equation 5 below in the blaze-type phase function.

$$h = \frac{\phi_{n-1} - \phi_n}{2\pi} \quad \text{[Equation 5]}$$

h: Phase constant $\phi_{n-1} - \phi_n$: Phase difference between the inner and outer positions in the $n^{th}$ diffraction zone 'Relief' collectively means a microstructure of uneven surface formed on the lens obtained through a conversion of the phase profile specifically into the lens contours reflecting the optical path length equivalent to the phase defined in the phase profile. The specific method of converting the phase profile into the relief configuration is described as follows:

When light enters into a medium with a certain refractive index, its speed is reduced according to the refractive index. The light wavelength changes as much as the change in its speed resulting in a phase change. Since a positive phase in the phase profile means reduced speed of light, incident light into a region of high refractive index is equivalent to bringing it to a positive phase. The terms positive and negative phases are relative expressions, and comparing the phases of $-2\pi$ and $-\pi$ for example, the latter lags behind the former even with the same sign, thus setting a region of higher refractive index than the former.

If lens has a blaze-like phase function for example, the actual form of the blazed step is expressed by Equation 6 below. Such a relief configuration can be added to a lens by machining it with a precision lathe or by a molding method.

$$\text{[Equation 6] blazed step height} = h \times \lambda / (n_s - n_m)$$

h: Phase constant described above
$\lambda$: Wavelength
$n_s$: Refractive index of the lens's base material
$n_m$: Refractive index of the medium facing the lens 'Intensity distribution' is a series of plotted values of the intensity of light that has passed through a lens, which is expressed as conjugate absolute values of the amplitude function described above. In this case, it is divided into two main categories, intensity distribution on the optical axis and intensity distribution on the image plane. The former refers to the position of lens as a base point to plot the distribution of intensity of light on the optical axis on the image side, which is used to find where the focal point is formed on the optical axis and what the intensity ratio of the light is. On the other hand, the image plane intensity distribution shows the distribution of light intensity on a certain image plane, which is expressed in the present invention by plotting the values of intensity at the position p in the direction of zero deviation angle of radius vector seen from the center of the image plane. In the human eye, what is perceived by the retina is the intensity distribution on the image plane.

'Fresnel pitch' means one form of pitch of zones determined in accordance with certain rules. In this context, it indicates the pitch determined by Equation 7 below assuming that the outer radius of the $n^{th}$ zone is $r_n$.

$$r_n = \sqrt{\frac{\{2(n-1) + g\} \times \lambda}{P_{add}}} \quad \text{[Equation 7]}$$

n: Zone number $$g = \frac{P_{add} \times r_1^2}{\lambda}$$

$\lambda$: Wavelength
$P_{add}$: Addition power in setting the focal point of the first-order diffracted light using the focal point position of 0th order diffracted light as a reference
$r_n$: Outer radius of the $n^{th}$ diffraction zone
$r_1$: Outer radius of the $1^{st}$ diffraction zone Generally speaking, the addition power $P_{add}$ (which gives an indication as to where the focal point position for near vision should be set when the 0th order and first-order light are assigned to far and near vision, respectively) corresponding to the focal point of the first order-diffracted light can be set by means of setting the pitch as determined by Equation 7 above. The diffraction-type lens used in the present invention with the Fresnel pitch is different from the Fresnel lens using the refraction principle and refers to a lens using the diffraction principle with the pitches in accordance with the equation above.

Subsequently, some aspects of the present invention designed to solve the above problems will be described below. The components adopted in each aspect described below are also adoptable in as many combinations as possible.

That is, a first aspect of the present invention relating to a multifocal ophthalmic lens provides a multifocal ophthalmic lens having a focal point formation region which is provided in an optical part of the lens and gives at least two focal points, characterized in that at least one cancellation region is provided in the optical part that, on an image plane at a first one of the focal points, produces a diffracted light with an amplitude distribution that reduces amplitudes of a light other than the one that forms the first focal point.

In the multifocal ophthalmic lens of the present aspect, a cancellation region is provided in the optical part that, on the first focal point image plane, produces a diffracted light that can reduce amplitudes of a light other than the one that forms the first focal point. This allows the amplitude distribution of light other than the one that forms the first focal point on the first focal point image plane to be restricted, and as a result, improving the visual quality of images.

The cancellation region of the present aspect can be created by means of providing in the optical part a region that produces diffracted light with an amplitude distribution that can reduce amplitudes in the peripheral region on the image plane at the first focal point out of those described above, for example, and the range of such region is favorably expressed by the following formula:

$\rho$ (peripheral region on the image plane): 0.0007f or more
(f: Focal length (mm) of the first focal point)

Also, the amplitude distribution does not have to be reduced by the diffracted light from the cancellation region for all the light other than the one that forms the first focal point. For example, diffracted light that forms one or more particular focal points other than the first focal point or diffracted light that produces an amplitude distribution located in one or more particular regions on the image plane of the first focal point can be subject to reduction.

A second aspect of the present invention related to a multifocal ophthalmic lens provides the multifocal ophthalmic lens according to the first aspect, wherein the first focal point provided by the focal point formation region is a focal point for far vision and a rest of the focal points provided by the focal point formation region includes a focal point for near vision.

In the multifocal ophthalmic lens of the present aspect, the cause of the halo is considered to be the light from the focal point formation region that provides a focal point for near vision being diffused to stray into the image plane at the focal point for far vision after focusing, and the halo that tends to be a problem especially with far vision at night can be effectively restricted. In other words, since the optical part is provided with the cancellation region that produces diffracted light with an amplitude distribution that can reduce the amplitude of light from the focal point formation region on the image plane at the far vision focal point, the stray light causing the halo can be cancelled, thus reducing the halo formation.

A third aspect of the present invention related to a multifocal ophthalmic lens provides the multifocal ophthalmic lens according to the first or second aspect, wherein the focal point formation region is formed in an inner peripheral portion of the optical part, while the cancellation region is formed in an outer peripheral portion of the optical part.

According to the present aspect, the focal point formation region is formed in the inner peripheral portion of the optical part, while the cancellation region is formed in the outer peripheral portion thereof. This allows the external light to pass through the inner peripheral portion of the optical part under bright conditions where the halo is not a problem due to the diameter reducing effect of the pupil so that a lot of light beams pass through the focal point formation region, while the light passing through the cancellation region is restricted. This reduces the impact of the cancellation region on the imaging characteristics of the focal point formation region, and as a result, maintaining the intrinsic quality of far and near vision in the focal point formation region.

Also, since the pupil dilates at night when the halo tends to be a problem, the light can be made incident into the outer peripheral area where the cancellation region is formed. The light causing the halo can be canceled by the cancelling light generated by the light incident into the cancellation region, making it possible to reduce the halo formation.

A fourth aspect of the present invention related to a multifocal ophthalmic lens provides the multifocal ophthalmic lens according to the third aspect, wherein an inner diameter of a formation area of the cancellation region is made larger than a pupil diameter of a human eye under bright conditions, and an outer diameter of the formation area of the cancellation region is made smaller than the pupil diameter of the human eye under dark conditions.

According to the present aspect, due to the inner diameter of the formation area of the cancellation region made larger than that of the human pupil, more light can be incident through the inner peripheral portion of the optical part in the focal point formation region, for example under bright conditions where the halo is not a problem, while minimizing the impact of the cancellation region on the imaging characteristics of the focal point formation region and maintaining the intrinsic quality of far and near vision in the focal point formation region. Also, the outer diameter of the formation area of the cancellation region is made smaller than that of the human pupil under dark conditions. This makes it possible that enough light passes through the cancellation region that can reduce the halo formation, for example at night when the halo tends to be a problem.

A fifth aspect of the present invention related to a multifocal ophthalmic lens provides the multifocal ophthalmic lens described in the third or fourth aspect, wherein the inner diameter of the formation area of the cancellation region is set at 2-6 mm, while the outer diameter of the formation area of the cancellation region is set at 3-8 mm.

According to the present aspect, due to the inner diameter of the formation area of the cancellation region set at 2-6 mm and the outer diameter of the formation area thereof set at 3-8 mm, the variability of the cancelling effect such as differences of changes in pupil diameters among individuals and races under bright or dark conditions or such changes due to a slight variation of brightness under the conditions can be reduced.

A sixth aspect of the present invention related to a multifocal ophthalmic lens provides the multifocal ophthalmic lens according to in any of the first to fifth aspects, wherein the focal point formation region is made larger than the cancellation region within an area 5 mm or less in diameter of the optical part.

According to the present aspect, the focal point formation region is made larger than the cancellation region within the area 5 mm or less in diameter. This reduces the impact of the cancellation region on the imaging characteristics of the focal point formation region, thus maintaining the intrinsic quality of far and near vision in the focal point formation region.

A seventh aspect of the present invention related to a multifocal ophthalmic lens provides the multifocal ophthalmic lens according to any of the first to sixth aspects, wherein the focal point formation region is composed of a diffraction structure where a plurality of diffraction zones are formed concentrically, and the first focal point is given by a 0th order diffracted light in the diffraction structure while the rest of the focal points is given by a first-order diffracted light in the diffraction structure.

According to the present aspect, the first focal point is given by the 0th order diffracted light in the diffraction structure and the rest of the focal points are given by the first-order diffracted light in the diffraction structure so that they can be designed independently from each other, thus enhancing the degree of design freedom.

An eighth aspect of the present invention related to a multifocal ophthalmic lens provides the multifocal ophthalmic lens according to the seventh aspect, wherein at least two focal points formed by the diffraction structure of the focal point formation region are given by the diffraction zones characterized by a phase function for modulating a light phase.

According to the present aspect, at least two focal points formed by the diffraction structure of the focal point formation region are given by the diffraction zones characterized by the phase function for modulating the light phase. This leads to an advantage of being able to design a diffraction structure of the focal point formation region in higher precision without reducing the amount of transmitted light as compared to the amplitude modulation-type diffraction structure combining a light transmission zone and a non-transmission zone, for example.

A ninth aspect of the present invention related to a multifocal ophthalmic lens provides the multifocal ophthalmic lens according to the eighth aspect, wherein a part or whole of the phase function of the diffraction zones in the diffraction structure of the focal point formation region is composed of a blaze-like function.

According to the present aspect, by making a part or whole of the phase function of the diffraction zones in the diffraction structure of the focal point formation region a blaze-like function, it is now possible to selectively allocate most of the incident light energy between the 0th order diffracted light and the first-order diffracted light, whereby enabling to get a favorable visual balance between far and near vision, and to express an amplitude distribution $A(\rho)$ for reducing the amplitude in the peripheral region on the image plane at the first focal point (namely, the first focal point image plane) using a simple equation, thus enabling simplification and time saving of the computer simulation. Also, it allows calculations in higher precision and more accurate design. In other words, cancellation of light is made possible in higher precision and more accurate reduction of the targeted halo is enabled.

A tenth aspect of the present invention related to a multifocal ophthalmic lens provides the multifocal ophthalmic lens according to any of the seventh to ninth aspects, wherein the diffraction structure of the focal point formation region includes zones having an outer radius of Fresnel pitch determined by Equation 7 above.

According to the present aspect, due to the diffraction structure of the focal point formation region having a periodic structure with the Fresnel pitch, the focal points formed by the 0th order and first-order diffracted light from the diffraction structure of the focal point formation region can be made more distinctive and intense. The zones that meet Equation 7 do not have to constitute the entire diffraction structure of the focal point formation region but they can only constitute part of it. Also, if the first-order diffracted light is made to form the near vision, such a focal point position can freely be determined for any $r_1$ using Equation 7.

An eleventh aspect of the present invention related to a multifocal ophthalmic lens provides the multifocal ophthalmic lens according to any of the seventh to tenth aspects, wherein the diffraction structure of the focal point formation region has a periodic structure with equal pitches.

The publicly known problem of the halo in the diffraction-type lens is caused by the light other than the one that forms the first focal point being diffused after focusing or being on the way to focus straying into the image plane of the first focal point. The strayed light that causes the halo forms a group of small peaks around the main peak on the image plane of the first focal point. According to the present aspect, the diffraction structure of the focal point formation region has a periodic structure with equal pitches. This makes it possible to formulate the group of small peaks which used to be difficult to design by specifying the position and intensity thereof in the conventional Fresnel pitch diffraction-type lens, thus enabling the design of the cancellation region through easy identification of the position and intensity of the peaks. The zones that meet the aforementioned condition of equal pitches do not have to constitute the entire diffraction structure of the focal point formation region, but they can only constitute part of it.

A twelfth aspect of the present invention related to a multifocal ophthalmic lens provides the multifocal ophthalmic lens according to any of the first to eleventh aspects, wherein an amplitude distribution $A(\rho)$ for reducing the amplitude on the image plane at the first focal point by the light other than the one that forms the first focal point is given by a phase function $\phi_c(r)$ for modulating a light phase provided in the cancellation region which is expressed by Equation 8 below using the phase function $\phi_c(r)$.

$$A(\rho) = E_0 \exp\left[i\left(kf + \frac{k\rho^2}{2f}\right)\right] \times \int_{r_{n-1}}^{r_n} \left[\exp\{i\phi_C(r)\} \times \exp\left\{-i\frac{k\rho}{f} \times r\right\}\right] dr \quad \text{[Equation 8]}$$

$\lambda$: Wavelength
$E_0$: Intrinsic amplitude
$k$: Wavenumber, defined by $k=2\pi/\lambda$
$f$: Focal length of the first focal point
$\rho$: Position in the radial direction measured from the center of image plane at the first focal point position
$r_{n-1}$: Inner radius of the cancellation region
$r_n$: Outer radius of the cancellation region
$\phi_c(r)$: Phase function of the cancellation region
$r$: Position measured from the lens center in the radial direction According to the present aspect, the amplitude distribution $A(\rho)$ for reducing the amplitude of the light other than the one that forms the first focal point on the image plane at the first focal point is given by the phase function $\phi_c(r)$ for modulating the light phase provided in the cancellation region, which is expressed by Equation 8 above using the phase function $\phi_c(r)$. This allows the cancellation region to be designed specifically and quantitatively by mathematical analysis.

A thirteenth aspect of the present invention related to a multifocal ophthalmic lens provides the multifocal ophthalmic lens according to the twelfth aspect, wherein the phase function $\phi_c(r)$ of the cancellation region is determined by Equation 9 below.

$$\phi_c(r) = \sum_{i=1}^{l} \left[a_i \times \sin\left\{\alpha_i\pi \times \left(\frac{r - r_{n-1}}{r_n - r_{n-1}}\right)^{s_i} + \beta_i\right\} + \quad \text{[Equation 9]}$$

-continued $$a'_i \times \cos\left\{\alpha'_i \pi \times \left(\frac{r-r_{n-1}}{r_n - r_{n-1}}\right)^{s'_i} + \beta'_i\right\} + \tau$$

$a_i$, $a'_i$, $\alpha_i$, $\alpha'_i$, $\beta_i$, $\beta'_i$: Constant
$s_i$, $s'_i$: Exponent. Real number other than 0
$r_n$: Outer radius of the cancellation region
$r_{n-1}$: Inner radius of the cancellation region
$\tau$: Phase shift (radian)
r: Position measured from the lens center in the radial direction According to the present aspect, it is now possible to obtain the phase function $\phi_c(r)$ of the cancellation region through computer simulation using Equation 9 above. This allows the light causing the halo to be cancelled, thus reducing the halo formation.

A fourteenth aspect of the present invention related to a multifocal ophthalmic lens provides the multifocal ophthalmic lens according to the twelfth aspect, wherein the phase function $\phi_c(r)$ is composed of a blaze-like function.

According to the present aspect, by means of making the phase function $\phi_c(r)$ of the cancellation region a blaze-like function, it is now possible to express the amplitude distribution A(ρ) for reducing the amplitude in the peripheral region on the image plane at the first focal point by a simple equation, thus enabling simplification and time saving of the computer simulation. Also, it enables calculations in higher precision and more accurate design. In other words, cancellation of light is made possible in higher precision and more accurate reduction of the targeted halo is enabled.

A fifteenth aspect of the present invention related to a multifocal ophthalmic lens provides the multifocal ophthalmic lens according to the fourteenth aspect, wherein the blaze-like function is determined by Equation 10 below.

$$\phi_c(r) = \left(\frac{\phi_n - \phi_{n-1}}{r_n - r_{n-1}}\right) \times r + \left(\frac{\phi_{n-1} \times r_n - \phi_n \times r_{n-1}}{r_n - r_{n-1}}\right) + \tau \quad \text{[Equation 10]}$$

$\phi_n$: Phase at the position of outer radius of the cancellation region
$\phi_{n-1}$: Phase at the position of inner radius of the cancellation region
$r_n$: Outer radius of the cancellation region
$r_{n-1}$: Inner radius of the cancellation region
$\tau$: Phase shift (radian)
r: Position measured from the lens center in the radial direction According to the present aspect, the phase function $\phi_c(r)$ is set as a function expressed by Equation 10 above. This allows the amplitude distribution A(ρ) for reducing the amplitude in the peripheral region on the image plane at the first focal point to be expressed by a simple equation, thus enabling simplification and time saving of the computer simulation. Also, it enables calculations in higher precision and more accurate design. In other words, cancellation of light is made possible in higher precision, enabling more accurate reduction of the targeted halo.

A sixteenth aspect of the present invention related to a multifocal ophthalmic lens provides the multifocal ophthalmic lens according to the thirteenth or fifteenth aspect, wherein the phase shift $\tau$ is within a range defined by Equation 11 below.

$$(2m-1.75) \times \pi \leq \tau \leq 2m\pi \ (m: \text{integer}) \quad \text{[Equation 11]}$$

According to the present aspect, the phase shift $\tau$ is set within the range expressed by Equation 11. This makes it possible to design the cancellation region that can effectively reduce the halo in a very easy manner without performing a detailed computer simulation.

A seventeenth aspect of the present invention related to a multifocal ophthalmic lens provides the multifocal ophthalmic lens according to the sixteenth aspect, wherein the phase shift $\tau$ is determined by Equation 12 below.

$$\tau = (2u-1)\pi \ (u: \text{integer}) \quad \text{[Equation 12]}$$

According to the present aspect, the phase shift $\tau$ is to be determined by Equation 12. This makes it extremely easy to obtain the amplitude distribution A(ρ) for reducing the amplitude in the peripheral region on the first focal point image plane in order to cancel the light that causes the halo. In other words, it is now possible to design the cancellation region that can restrict the halo formation in the most simple and effective manner.

An eighteenth aspect of the present invention related to a multifocal ophthalmic lens provides the multifocal ophthalmic lens according to any of the first to seventeenth aspects, wherein the focal point formation region is composed of a diffraction structure where a plurality of diffraction zones are formed concentrically, and an interval of the cancellation region is made equal to pitch of one of the diffraction zones of the diffraction structure in the focal point formation region.

According to the present aspect, the interval of the cancellation region is made equal to pitch of one of the diffraction zones of the diffraction structure in the focal point formation region. This makes it easy to cancel the light that causes the halo generating from the diffraction structure in the focal point formation region, thus achieving the reduction of halo formation by a very simple configuration.

A nineteenth aspect of the present invention related to a multifocal ophthalmic lens provides the multifocal ophthalmic lens according to any of the first to eighteenth aspects, wherein the at least one cancellation region comprises a plurality of cancellation regions arranged in a radial direction of the lens.

According to the present aspect, the cancellation region is provided in plurality in the radial direction of the lens. This enhances the degree of freedom in designing the cancellation region.

A twentieth aspect of the present invention related to a multifocal ophthalmic lens provides the multifocal ophthalmic lens according to any of the first to nineteenth aspects, wherein a part or whole of the cancellation region is provided within a maximum outer diameter of the focal point formation region.

According to the present aspect, part or whole of the cancellation region is provided within the maximum outer diameter of the focal point formation region. This enhances the degree of freedom in designing the cancellation region.

A twenty-first aspect of the present invention related to a multifocal ophthalmic lens provides the multifocal ophthalmic lens according to any of the first to twentieth aspects, wherein the focal point formation region and the cancellation region are alternately formed in a radial direction of the optical part, and at least two cancellation regions are formed in the radial direction of the optical part.

According to the present aspect, the formation areas of the focal point formation region and the cancellation region are alternately formed in the radial direction of the optical part, and at least two formation areas of the cancellation region are formed in the radial direction of the optical part. This enhances the degree of freedom in designing the cancellation region.

A twenty-second aspect of the present invention related to a multifocal ophthalmic lens provides the multifocal ophthalmic lens according to any of the first to twenty-first aspects, wherein the first focal point is given by the diffraction structure provided in the focal point formation region, while the diffraction structure in the focal point formation region and the diffraction structure in the cancellation region are both made as a relief structure reflecting an optical path length equivalent to a phase defined by a phase function representing a phase profile of the diffraction structure.

According to the present aspect, the diffraction structures of the focal point formation region and the cancellation region are both made to be a relief structure. This allows the phase function to be built accurately as a diffraction structure in real form, enabling to manufacture the diffraction structure in high precision. As a result, the targeted halos can be reduced more accurately.

A twenty-third aspect of the present invention related to a multifocal ophthalmic lens provides the multifocal ophthalmic lens according to any of the first to twenty-second aspects, wherein the diffraction structure provided in the focal point formation region to form the first focal point and the diffraction structure in the cancellation region are composed of blaze-like diffraction zones formed concentrically to each other, while an inclination of the blaze in the diffraction zone of the diffraction structure in the cancellation region is reversed from that of the blaze in the diffraction zone in the focal point formation region.

According to the present aspect, the amplitude function of the cancellation region can be shifted by reversing the blaze inclination in the diffraction zones of the diffraction structure in the cancellation region. It is possible to adjust the amount of such shift by setting a value of the phase constant, and the amplitude function deriving from the cancellation region can have its positive and negative signs inverted at a desired position by means of setting a proper phase constant, thus exerting an effective cancelling effect.

A twenty-fourth aspect of the present invention related to a multifocal ophthalmic lens provides the multifocal ophthalmic lens according to the twenty-third aspect, a certain amount of phase shift is set up for the diffraction zone in which the inclination of the blaze is reversed in the cancellation region.

According to the present aspect, the degree of design freedom is enhanced by adopting a reversed inclination of the blaze in the cancellation region and the setting of a phase shift therein individually or in combination with each other, for example by means of properly corresponding to the type of the focal point formation region. Also, there can be another way of designing the lens whereby the level gap between the blaze at the inner peripheral edge of the cancellation region and the blaze at the outer peripheral edge of the focal point formation region adjacent thereto on the inside is minimized, for example by means of setting a proper amount of phase shift in the cancellation region where the blaze inclination is reversed.

A twenty-fifth aspect of the present invention related to a multifocal ophthalmic lens provides the multifocal ophthalmic lens according to any of the first to twenty-fourth aspects, wherein the diffraction structure provided in the focal point formation region to form the first focal point and the diffraction structure in the cancellation region are composed of diffraction zones formed concentrically to each other, while a refraction region provided with a refracting interface is formed between the diffraction zone in the focal point formation region and the diffraction zone in the cancellation region.

According to the present aspect, it is possible to adopt a multifocal ophthalmic lens having a refraction region provided with a refracting interface between the focal point formation region and the cancellation region so that the degree of freedom in designing such multifocal ophthalmic lenses is enhanced. The width dimension of the refraction region in the radial direction can be adjusted as appropriate depending on the desired cancelling effect.

A twenty-sixth aspect of the present invention related to a multifocal ophthalmic lens provides the multifocal ophthalmic lens according to any of the first to twenty-fifth aspects, wherein the diffraction structure provided in the focal point formation region to form the first focal point and the diffraction structure in the cancellation region are each composed of a relief structure, while the relief structure in each of the focal point formation region and the cancellation region is formed on one of front and back surfaces of the optical part of the lens.

According to the present aspect, the relief structures in the focal point formation region and the cancellation region are adoptable on either front or back surface of the optical part of the lens so that such focal point formation region and cancellation region are applicable to various ophthalmic lenses, while the degree of freedom in designing such multifocal ophthalmic lenses can further be enhanced.

A twenty-seventh aspect of the present invention related to a multifocal ophthalmic lens provides the multifocal ophthalmic lens according to any of the first to twenty-sixth aspects, wherein the multifocal ophthalmic lens is a multifocal contact lens.

According to the present aspect, the light causing the halo can be cancelled by applying the present invention to a multifocal contact lens, enabling to offer a multifocal contact lens that can reduce the halo formation.

A first aspect of the present invention related to a manufacturing method of a multifocal ophthalmic lens provides a manufacturing method of a multifocal ophthalmic lens having a focal point formation region which is provided in an optical part of the lens and gives at least two focal points, characterized by setting a cancellation region in the optical part of the lens that, on an image plane at a first one of the focal points, is capable of reducing amplitudes of a light other than the one that forms the first focal point by means of a phase function $\phi_c(r)$ of Equation 8 above that expresses an amplitude distribution $A(\rho)$ that reduces the amplitudes of the light other than the one that forms the first focal point on the image plane at the first focal point.

Also in the present aspect, the cancellation region is set up in the optical part of the lens to be able to reduce the amplitude in the peripheral region on the first focal point image plane using the phase function $\phi_c(r)$ of Equation 8 that expresses the amplitude distribution $A(\rho)$ capable of reducing the amplitude in the amplitude distribution in the peripheral region on the first focal point image plane so that the stray light causing the halo and the like can be cancelled, thereby alleviating the halo problem.

A second aspect of the present invention related to a manufacturing method of a multifocal ophthalmic lens provides the manufacturing method of the multifocal ophthalmic lens according to the first aspect, wherein the phase function $\phi_c(r)$ of the cancellation region is determined by Equation 9 above.

According to the present aspect, it is now possible to obtain the phase function $\phi_c(r)$ of the cancellation region through computer simulation using Equation 9. This allows the light causing the halo to be cancelled, thus reducing the halo formation.

A third aspect of the present invention related to a manufacturing method of a multifocal ophthalmic lens provides the manufacturing method of the multifocal ophthalmic lens according to the first aspect, wherein the phase function $\phi_c(r)$ of the cancellation region is determined by Equation 10 above.

Even in the present aspect, it has become possible to obtain the phase function $\phi_c(r)$ of the cancellation region through computer simulation using Equation 10. This allows the light causing the halo to be cancelled, thus reducing the halo formation.

Effect of the Invention

The present invention was completed based on the publicly known halo problem in the multifocal lens such as a diffraction-type lens is caused by that the light other than the one that forms the first focal point to be used as a far focal point is diffused after focusing or is on the way to focus straying into the image plane of the first focal point. Then, according to the multifocal ophthalmic lens of the present invention, a cancellation diffraction structure is provided in the optical part that, on the first focal point image plane, produces a diffracted light that can reduce amplitudes of a light other than the one that forms the first focal point. Thus, the stray light causing the halo can be cancelled, thus reducing the halo formation and the like and enhancing the visual quality of images.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 10A and 10B are graphs for comparing a result of simulation of intensity distribution on the optical axis of the present invention with that of the comparative example.

FIGS. 39A-39C are enlarged views of the phase profile in the cancellation region of the third embodiment.

EMBODIMENTS FOR CARRYING OUT THE INVENTION

For the present invention, the mechanism of the halo phenomenon will be described first for the purpose of reducing it and then some methods of halo reduction will be described based on such mechanism. Then, such methods and characteristics will be described based on specific embodiments.

As described above, the cause of the halo is the group of small peaks generated around the main peak on the image plane at far focal point. This group of peaks will hereinafter be called "side-band peaks." Such peaks have the amplitude distribution deriving from the property of light as waves. Therefore, based on the wave superposition, it is easily understandable that the amplitude is reduced by superposing another amplitude with its positive and negative signs inverted. Once the amplitude is reduced, the peak intensity drops down in the same region. That is, the halo reduces its intensity. In other words, the primary purpose of the present invention is to provide a method of actively reducing the halo formation by means of identifying the amplitude distribution that causes the halo and sending light waves that offset such amplitude.

Figure 1A:
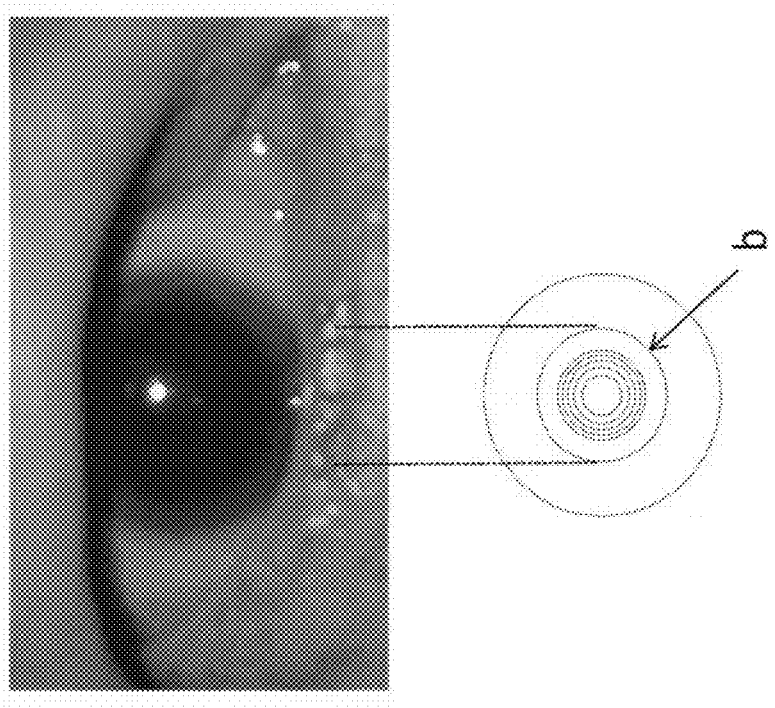
FIGS. 1A and 1B are views suitable for explaining pupil diameters during daytime and nighttime.
Figure 1B:
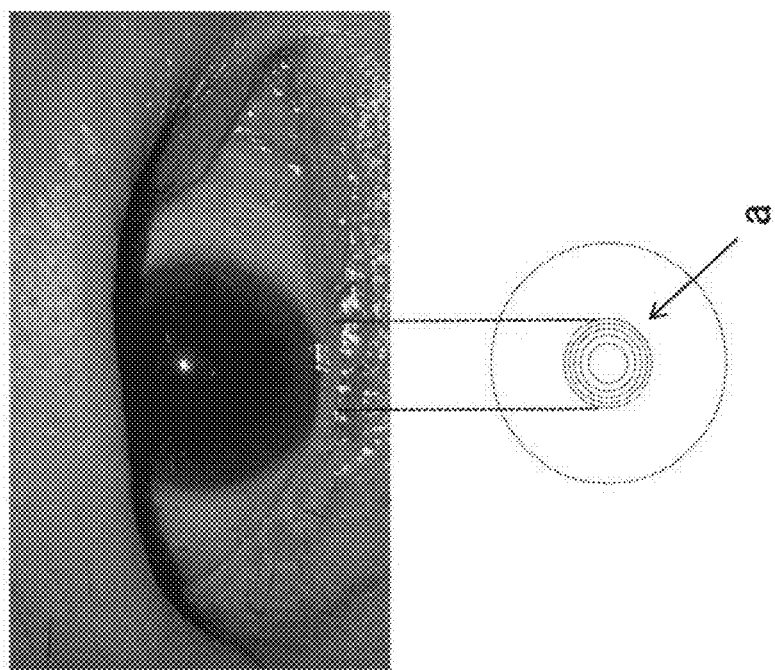

The next important thing is to find out which region of the optical part of the lens the light is emitted from to offset the amplitude without compromising the quality of far and near vision. A further important aspect of the present invention is the use of the physiological mechanism of the human eyesight in setting such a region. The diameter of a human pupil changes in response to the brightness of the environment. In a bright environment with ample light explained by a term 'photopic vision,' the pupil gets smaller in diameter ranging from about 1.8 to 2 mm, for example, in a highly illuminated outdoor environment under clear sky, and from about 2.5 to 3.5 mm in an environment with the standard office illuminance (FIG. 1A shows an actual photo of a human pupil taken in the standard office illuminance with the pupil diameter at about 3.5 mm). In a slightly darker environment in early evening explained by a term 'mesopic vision,' the pupil gets larger in diameter at about 4 mm, and in a dark environment at night explained by a term 'scotopic vision,' the pupil is further dilated up to 5 to 7 mm in diameter (FIG. 1B shows a photo of a human pupil taken in a darkroom with the pupil diameter at about 6 mm). Despite individual variation, the pupil diameter is generally to change in the range from the minimum of about 2 mm to the maximum of about 8 mm. In case of the multifocal ophthalmic lens, it is highly required that far and near vision be well balanced in environments ranging from photopic to mesopic, but in a dark environment at night, the necessity and importance of the near vision are not considered so high.

Therefore, the lens region equivalent to the pupil diameter in a photopic to mesopic environment (region 'a' in FIG. 1A) is considered to be the one to be designed with emphasis placed on far and near vision, whereas the halo at night can be reduced without compromising far and near vision in a photopic to mesopic environment by means of setting a region in the lens for cancelling and reducing the amplitude of light that causes halos around the newly emerged region (region 'b' in FIG. 1B) due to the dilated pupil at night. In other words, by means of separately providing a region specialized for far and near vision and a region exclusively for restricting the halo arising therefrom and making the best of changes in the pupil diameter in response to the environment, far and near vision are well balanced and a diffraction-type ophthalmic lens with reduced generation of halos can be offered. FIGS. 1A and 1B specifically show the lens region to be used by taking advantage of such changes in the pupil diameter, which clearly indicates that the region to be used in response to changes of the environment ranging from photopic to scotopic changes dynamically.

In the present invention, it is desirable that the region equivalent to the pupil diameter for photopic, or photopic to mesopic vision be specified as a region for focal point formation and the cancellation region be provided in the lens region newly emerged due to dilatation of the pupil in the darkness. The range of these regions is defined not precisely but approximately, taking into account the individual variation mentioned earlier.

The focal point formation region can adopt a commonly known diffraction structure for the purpose of forming desired multiple focal points. This can be achieved by the diffraction structure where a plurality of structural units generally called diffraction zones that can cause changes to the light phase are concentrically arranged. The focal point formation region can be designed as part of a multifocal lens with two focal points for far and near vision, or can be designed as part of a multifocal lens with three focal points that forms an intermediate focal point between far and near distances in addition to the far and near focal points. It can also be a multifocal lens that generates four or more focal points.

As a method of forming such focal points, conventionally known design methods and means can be used for generating multiple focal points in a diffraction-type lens. For example, the diffraction grating with zone pitches according to certain rules called 'Fresnel pitch' that can cause changes to the phase called blaze is something favorable for such focal point formation region. The focal point formation region needs to be arranged in the lens center to be able to properly form focal points for far and near distances mainly in a photopic environment or at each of far, intermediate and near positions.

Figure 2A:
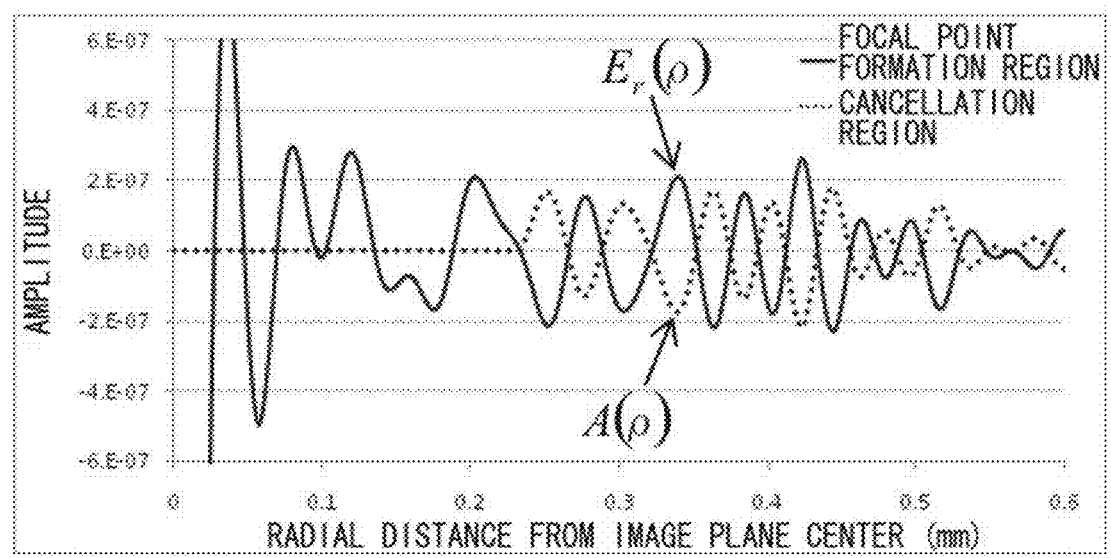
FIGS. 2A and 2B are conceptual diagrams of the cancelling mechanism of the present invention.

Next, the concept and specific method for designing a cancellation region will be described as follows: Assuming that a focal point formation region composed of diffraction zones for generating multiple focal points and a cancellation region are provided at different locations in a lens having a specific refracting interface. If the 0th order diffracted light from the focal point formation region is set up for far vision, it is necessary to obtain information on the amplitude function to control it on the 0th order focal point image plane in order to reduce the halo at night. Therefore, it becomes important in dealing with the light emitting from the cancellation region to make use of 0th order diffracted light and understand the behavior thereof. Assuming that the phase function of the cancellation region is $\phi_c(r)$, the amplitude function $E_c(\rho)$ formed on the 0th order focal point image plane by the light emitted from the cancellation region is expressed by Equation 13 below.

$$E_c(\rho) = E_0 \exp\left[i\left(kf + \frac{k\rho^2}{2f}\right)\right] \times \int_0^{2\pi} \int_{r_{n-1}}^{r_n} r \times \exp[i\phi_c(r)] \times \exp\left[-i\frac{k\rho\cos\theta}{f} \times r\right] dr\, d\theta \quad \text{[Equation 13]}$$

r: Distance from the lens center in the radial direction

θ: Angle representing the radius vector on the lens surface $r_{n-1}$: Inner radius of the cancellation region $r_n$: Outer radius of the cancellation region $\phi_c(r)$: Phase function of the cancellation region ρ: Position in the radial direction measured from the center of the 0th order focal point image plane $E_c(\rho)$: Amplitude function deriving from the cancellation region on the 0th order focal point image plane λ: Wavelength k: Wavenumber. Defined as k=2π/λ f: Focal length of the 0th order diffracted light $E_0$: Intrinsic amplitude value Since both the focal point formation region and cancellation region generally deal with a phase profile in a form symmetrical about the lens center, it is good enough to discuss the amplitude function in the vector direction of θ=0. Therefore, the cancelling conditions can be examined using Equation 14 below that expresses the amplitude deriving from the line segment region in the radius vector direction at θ=0.

$$E_c(\rho) = \quad \text{[Equation 14]}$$

$$E_0 \exp\left[i\left(kf + \frac{k\rho^2}{2f}\right)\right] \times \int_{r_{n-1}}^{r_n} \exp[i\phi_c(r)] \times \exp\left[-i\frac{k\rho}{f} \times r\right] dr$$

r: Distance from the lens center in the radial direction
$r_{n-1}$: Inner radius of the cancellation region
$r_n$: Outer radius of the cancellation region
$\phi_c(r)$: Phase function of the cancellation region
$\rho$: Position in the radial direction measured from the center of the 0th order focal point image plane
$E_c(\rho)$: Amplitude function deriving from the cancellation region on the 0th order focal point image plane
$\lambda$: Wavelength
k: Wavenumber. Defined as $k=2\pi/\lambda$
f: Focal length of the 0th order diffracted light
$E_0$: Intrinsic amplitude value Meanwhile, assuming that the amplitude function formed on the 0th order focal point image plane from the focal point formation region is $E_r(\rho)$ as shown in FIG. 2A, this amplitude function includes an amplitude that forms a main peak for generating a focal point for far vision and an amplitude that forms side-band peaks that cause the halo. Since the amplitudes around the main peak generally cause the halo, it is necessary to identify and extract them from the function $E_r(\rho)$ and let the light with an amplitude function that can reduce them be emitted from the cancellation region.

Figure 2B:
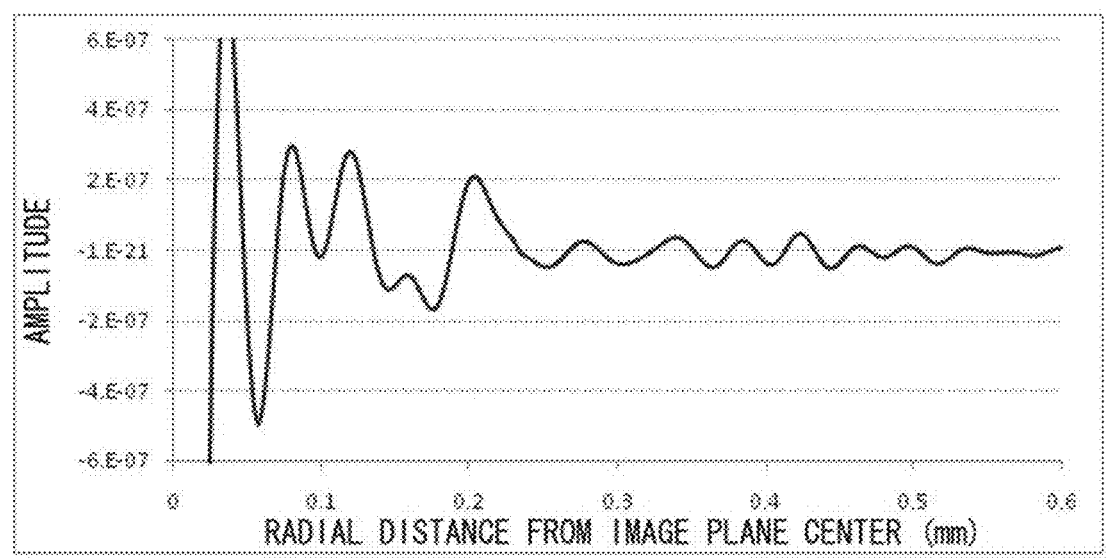

As shown in FIG. 2A, assuming that the amplitude function $A(\rho)$ is the one that can reduce the amplitude distribution in the peripheral region shown in the amplitude function $E_r(\rho)$, if the function $E_c(\rho)$ deriving from the cancellation region is equal to the function $A(\rho)$, it is possible to reduce amplitudes that cause the halo by having them offset each other as shown in FIG. 2B. In other words, once the phase function $\phi_c(r)$ of the cancellation region shown in Equation 8 is determined, such halo reduction can be achieved.

Since it is difficult to mathematically analyze Equation 8 for an actual diffraction-type lens, it is necessary to make an estimate of the phase function using the approximation method, numerical analysis method, or value fitting method as appropriate.

In order to determine the phase function by such means as numerical analysis, an algorithm or a program exclusively made for the purpose should be used. Steps of the procedure are exemplified as follows:

(1) Determine the amplitude distribution from the focal point formation region.

(2) Determine the amplitudes to be cancelled and the region thereof.

(3) Take samples of amplitude data in the region to make an amplitude function out of them.

(4) Analyze Equation 8 by using the exclusive algorithm or program.

(5) Make an estimate of the phase function.

In Step (1), an amplitude distribution can be calculated using the exclusive software for designing a diffraction-type lens such as the one for simulated calculation of diffraction used for the present invention.

In Step (2), the structure of the halo and the like is assumed in order to identify the region where amplitudes need to be cancelled. Especially when the halo is too expansive, the view of objects is blocked by the halo to make it difficult to visually recognize them so that it is important to reduce the expanse. For that reason, the amplitude function in the peripheral region of the image plane intensity distribution is extracted. Such data are obtained as discrete data.

Specific calculation methods relating to Steps (4) and (5) to achieve the purpose include the one using an algorithm such as the Fast Fourier transform.

Also, since Equation 8 is in a form of Fourier transform, the phase function $\phi_c(r)$ of the cancellation region can be estimated by means of defining a group of constants to fit the desired amplitude distribution as a phase function expressed by the series shown in Equation 9.

The paragraphs below show some examples of estimated phase functions based on a specific amplitude function or intensity distribution, and the effect of halo reduction.

The method, conditions and output data of the simulated calculation used in the present invention are as follows:

For the calculation, a simulation software was used that can calculate intensity distribution and the like based on diffraction integral equations. A far point light source was set up as light source for calculation, and the calculation was performed on the assumption that parallel light beams in the same phase enter into the lens. Also, in the calculation, it was assumed that the media on the object and image sides are vacuum and the lens is an ideal lens having no aberration (light beams passing through the lens form an image at the same focal point regardless of the emitting position of the light). Further, the calculation was performed based on the assumption that the wavelength equals 546 nm and the refractive power of the lens for the 0th order diffracted light (basic refractive power) equals 7D (Diopter).

As to the intensity distribution on the optical axis, intensity values were plotted relative to the distance along the optical axis from the lens as a base point. Also, as to the intensity distribution on the image plane, intensity values were plotted relative to the distance from the center in the direction of radius vector at zero angle. Unless otherwise noted, the vertical scale of intensity values in the image plane intensity distribution was fixed constant in the comparison between each embodiment and its comparative example. In addition, the amplitude function was represented by its real part in the present invention. The amplitude function is shown by plotting amplitude values relative to the distance from the center of the image plane in the radial direction as is the case with the intensity distribution on the image plane.

Because the focal point position of 0th order diffracted light is set at 7 (Diopter) (equivalent to the focal length f=142.8 mm) in the simulated calculation of the present invention, it should be noted that the values on the horizontal axis in the image plane coordinate is limited to those at such focal point position. A new position on the image plane with a different focal length can be calculated by the conversion using Equation 15 below.

$$\rho' = \frac{f'}{f}\rho \quad \text{[Equation 15]}$$

f: Focal length of 0th order diffracted light used for the calculation of the present embodiment ρ: Position in the radial direction measured from the center of the 0th order focal point image plane when the focal length=f f': Another focal length ρ': Position in the radial direction measured from the center of the 0th order focal point image plane when the focal length=f'

The position ρ' on the image plane when the focal length is 16.6 mm (assuming an ideal lens in the ophthalmic optics) can be calculated by the following conversion equation:

$$\rho'=(16.6/142.8)\times\rho=0.1167\times\rho$$

assuming that the position on the image plane in the present embodiment is ρ.

In order to further clarify the specifics of the present invention, embodiments of the present invention will be described in detail in reference to the drawings.

First Embodiment

Figure 3:
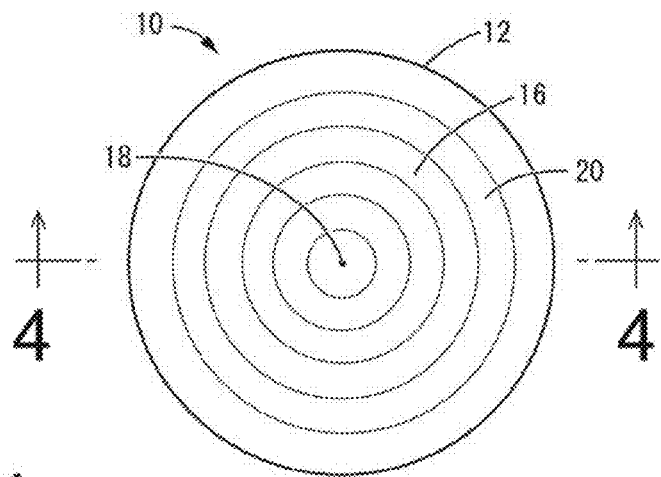
FIG. 3 is a rear specific view of a contact lens as a first embodiment of the present invention.
Figure 4:
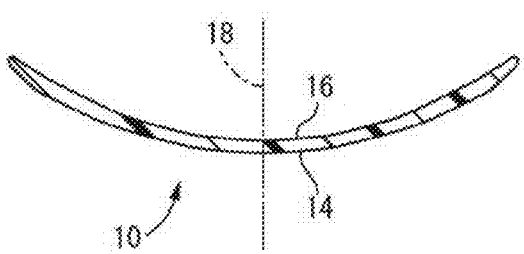
FIG. 4 is a cross sectional specific view of the contact lens of FIG. 3, taken along line 4-4 of FIG. 3.

First of all, FIG. 3 shows a rear model view of an optical part 12 of an ophthalmic lens 10, which is a contact lens as a first embodiment of the present invention related to a diffraction-type multifocal ophthalmic lens, while FIG. 4 shows a cross sectional model view of the optical part 12 of the ophthalmic lens 10.

The ophthalmic lens 10 has a broad region at its center as the optical part 12, and the publicly known peripheral and edge portions, not shown in the figure, are formed outside thereof. Also, the optical part 12 is formed as a whole with an optical part front surface 14 having a convex face in an approximate shape of a crown and an optical part back surface 16 having a concave face in approximately the same shape. And the optical part 12 of the ophthalmic lens 10 is made as a whole in an approximate form of a bowl with its center slightly thinned if it is to be used for correcting myopia or slightly thickened if it is to be used for correcting hyperopia, both being made into a solid of revolution about a lens central axis 18 as a geometric axis. Such ophthalmic lens 10 is directly worn on the cornea of the eye. Therefore, the optical part 12 of the ophthalmic lens 10 is preferably set to about 4 to 10 mm in diameter.

The optical part 12 of the ophthalmic lens 10 uses the optical part front surface 14 and the optical part back surface 16 as refracting interfaces. And a given focal length is set for the refracted light (0th order diffracted light) through the optical part front surface 14 and the optical part back surface 16, with a far focal point provided in the present embodiment.

As materials to form the ophthalmic lens 10, publicly known resin materials composed of various polymerizable monomers with optical properties such as light transmissivity or gel-like synthetic polymer composites (hydrogel) are preferably used, and more specifically, polymethylmethacrylate (PMMA), polyhydroxyethylmethacrylate (Poly-HEMA) and so forth can be quoted as examples.

Then, especially in the optical part back surface 16 of the present embodiment, a diffraction structure 20 is formed. The diffraction structure 20 is formed concentrically in plurality around the lens central axis 18 comprising a relief 21, which are contours in the radial direction extending continuously in an annular form in the circumferential direction of the lens. In the present embodiment, a far focal point as a first focal point is set by the 0th order diffracted light in the diffraction structure 20, and the rest of the focal points in the near region are set by the first-order diffracted light. And the focal point formation region is formed by the diffraction structure 20 that gives at least two of these focal points. As described above, the individual diffraction structure 20 is called a zone (diffraction zone) or an orbicular zone, which is characterized by a phase function that can modulate the light phase.

Figure 5A:
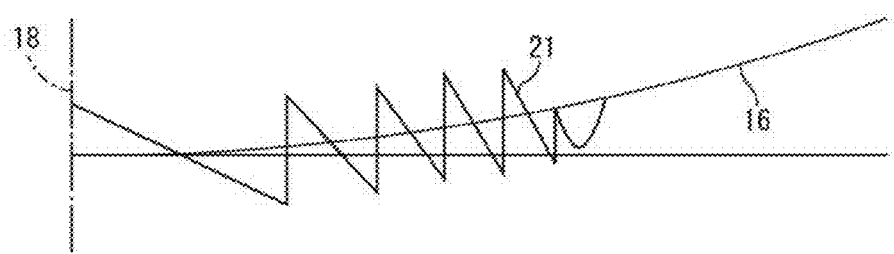
FIGS. 5A and 5B are cross sectional specific views suitable for explaining the relief configuration formed on the back surface of the contact lens shown in FIG. 3.
Figure 46:
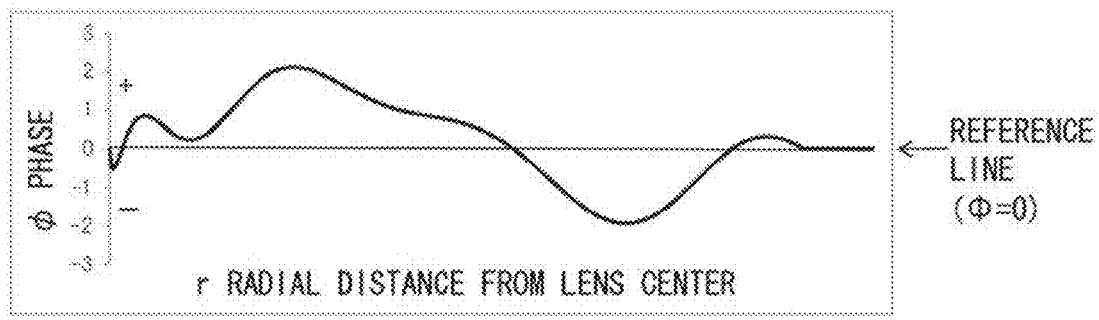
FIG. 46 is a conceptual diagram suitable for explaining the phase profile.
Figure 47A:
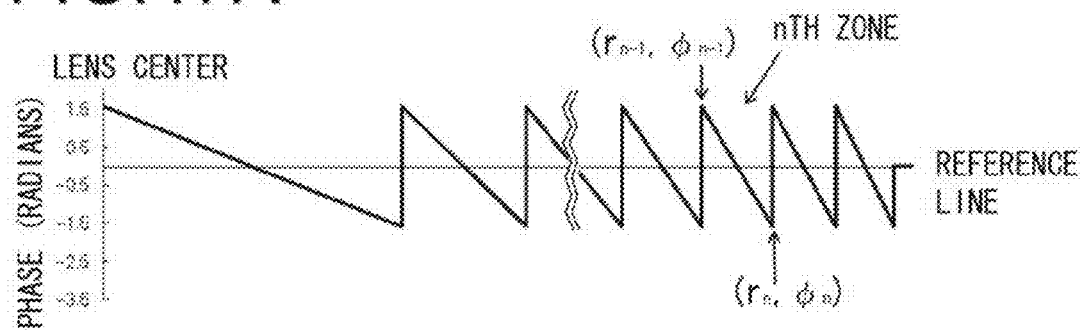
FIGS. 47A-47C are diagrams suitable for explaining the phase profile of the blaze-type phase profile.
Figure 47B:
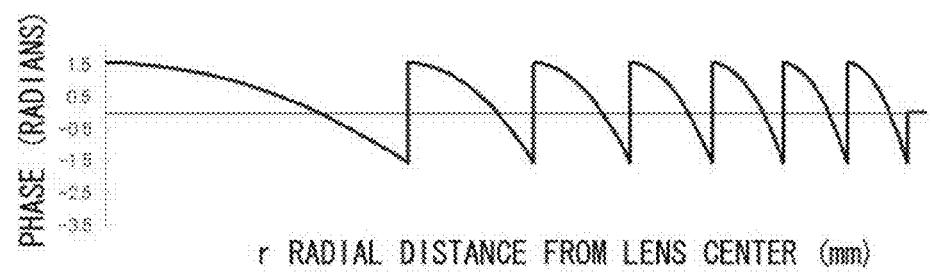
Figure 47C:
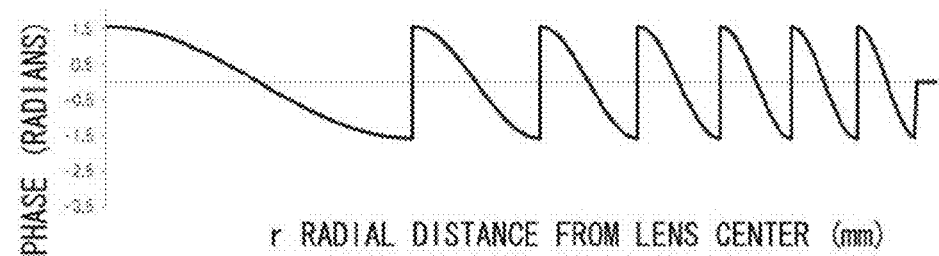
Figure 48:
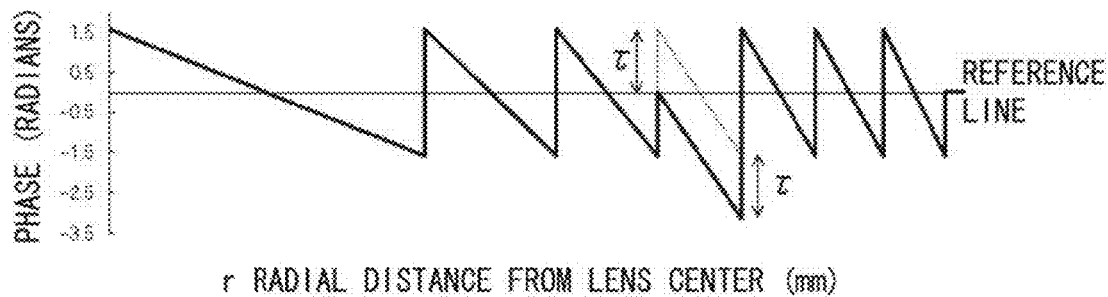
FIG. 48 is a diagram suitable for explaining the phase profile when a phase shift is given to the phase function.

FIG. 5A shows a magnified cross section of the relief 21 on the optical part back surface 16. The size of the relief 21 is exaggerated for better understanding in FIG. 5. As shown in FIG. 5A, the relief 21 is formed like stairs going up to the right reflecting the original configuration of the optical part back surface 16 of the ophthalmic lens 10. When the front and back surfaces of the optical part of the ophthalmic lens are made to have a single refractive power, there should be no problem to understand that the optical part back surface 16 is the datum line for the r-φ coordinate plane (FIG. 46) defined above. Also in FIG. 5A, the region below the boundary of the relief 21 is made of a contact lens base material and the upper region is made of an external medium. For better understanding, the shape of the relief 21 will be examined hereinafter without considering the original configuration on the optical part back surface 16 of the ophthalmic lens 10, that is, using the optical part back surface 16 as a linear x-coordinate in the radial direction as shown in FIG. 5B.

Figure 5B:
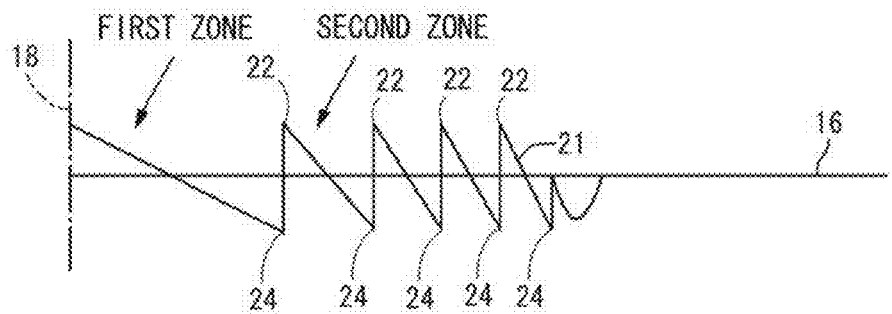

As shown in FIG. 5B, the relief 21 extends concentrically around the lens central axis 18, while being made with contours having ridge lines 22 protruding outward of the ophthalmic lens 10 (upward in FIGS. 4 and 5) and valley lines 24 protruding inward of the same (downward in FIGS. 4 and 5).

In the following descriptions, 'grating pitch' means a dimension between the ridge line 22 and the valley line 24 in the radial direction. 'Orbicular zone' or 'zone' means the area between the ridge line 22 and the valley line 24 and each zone is assigned a zone number starting from 1 for the central zone followed by 2, 3, and so forth. Also, 'zone radius' means an outer radius of each zone, that is, a radius of the ridge line 22 or the valley line 24 in each zone located outside the concentric center (lens central axis 18 in the present embodiment) measured from the concentric center. Therefore, 'grating pitch' means a width of each zone in the radial direction, and a grating pitch of a particular zone refers to a difference in radius between the zone and another zone with one less number. The diffraction structure composed of a relief configuration was described above together with specific examples of a contact lens, but in the descriptions below, the phase function or phase profile on which the design of the relief is based on will be used to explain the diffraction structure. Therefore, unless otherwise noted, the phase profile as a diffraction structure will hereinafter be displayed on the r-φ coordinate plane shown in FIG. 46.

Figure 6A:
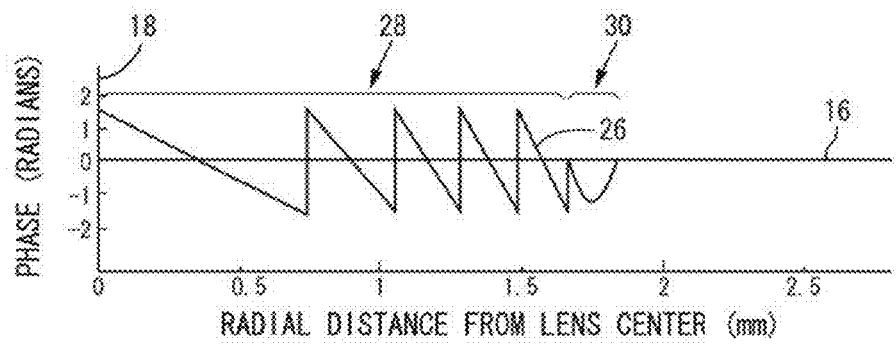
FIG. 6A is a phase profile of the first embodiment of the present invention and FIG. 6B is a phase profile of a comparative example.
Figure 6B:
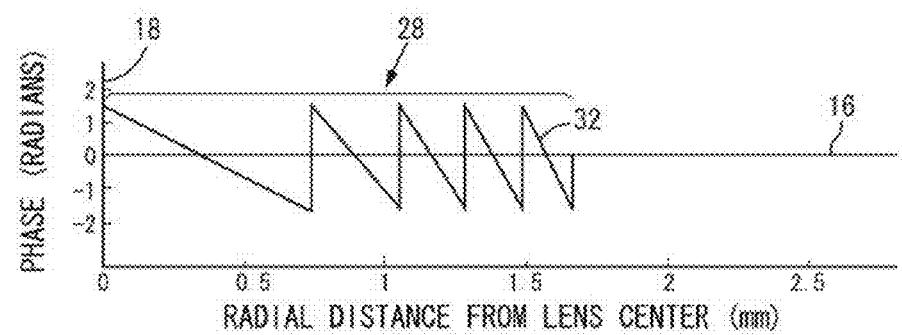
Figure 7:
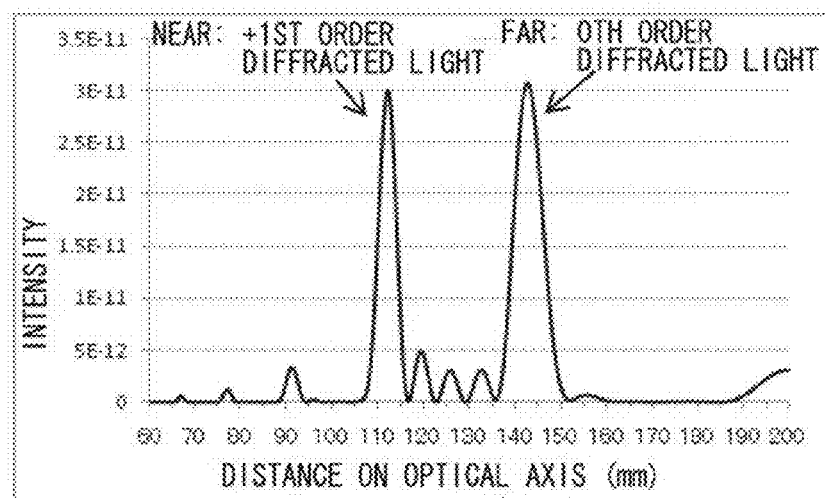
FIG. 7 is a graph showing a result of simulation of intensity distribution on the optical axis of the comparative example shown in FIG. 6B.

In order to present imaging characteristics of the conventional diffraction-type multifocal ophthalmic lens, the optical part 12 of the ophthalmic lens 10 is shown with a focal point formation region 28 at its center composed of five diffraction zones having a blaze-type phase function and following the Fresnel pitch (only the focal point formation region 28 of Table 1, the phase profile 32 of FIG. 6B). The optical part 12 has a given refractive power determined by the curvature of the optical part front surface 14 and the optical part back surface 16 in FIG. 4, and the outer region of the diffraction zone is made to be a refraction region that forms a single focal point based on such refractive power. In other embodiments described below, the outer region of the diffraction zone is made to be a refraction region having a single refractive power in the same way. Such diffraction structure 20 is designed to provide 0th order diffracted light for far vision and first-order diffracted light for near vision, and the near vision focal point is set to have addition power over the far vision focal point by 2 Diopter. Such diffraction structure is configured to have the phase constant at h=0.5 and designed to almost equalize the amount of light allocated to far and near distances under a photopic environment as evident from the intensity distribution on the optical axis in the present embodiment shown in FIG. 7.

TABLE 1

[First embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.738918 | 0 | −1.57079 | 1.57079 | 0.5 |
| | 2 | 1.044988 | 0.738918 | −1.57079 | 1.57079 | 0.5 |
| | 3 | 1.279844 | 1.044988 | −1.57079 | 1.57079 | 0.5 |
| | 4 | 1.477836 | 1.279844 | −1.57079 | 1.57079 | 0.5 |
| | 5 | 1.652271 | 1.477836 | −1.57079 | 1.57079 | 0.5 |
| Cancellation region | 6 | 1.809972 | 1.652271 | [Equation 16] | | — |

Also, calculation of intensity distribution on the 0th order focal point image plane in the conventional example described above gives the distribution shown in FIG. 8B, which indicates the existence of a group of side-band peaks in the peripheral region on the image plane. It is expected that halos will emerge at night reflecting these side-bands. Thus, a first aspect of the present invention is the one provided with a cancellation region 30 shown in Table 1 at a location adjacent to the focal point formation region 28 on the outside. In the following paragraphs, the regions such as the cancellation region 30 in the tables are marked with serial zone numbers for convenience sake, for example No. 6 in the present embodiment.

Figure 8A:
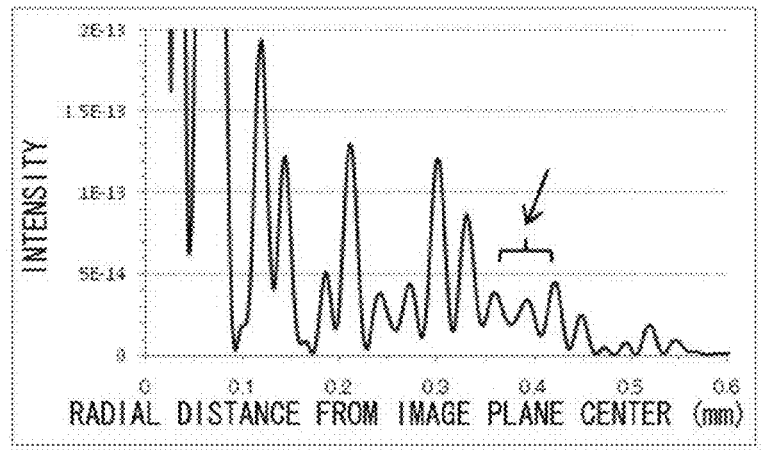
FIGS. 8A and 8B are graphs for comparing simulation results of image plane intensity distribution at the focal point position of 0th order diffracted light of the present embodiment with those of the comparative example.
Figure 8B:
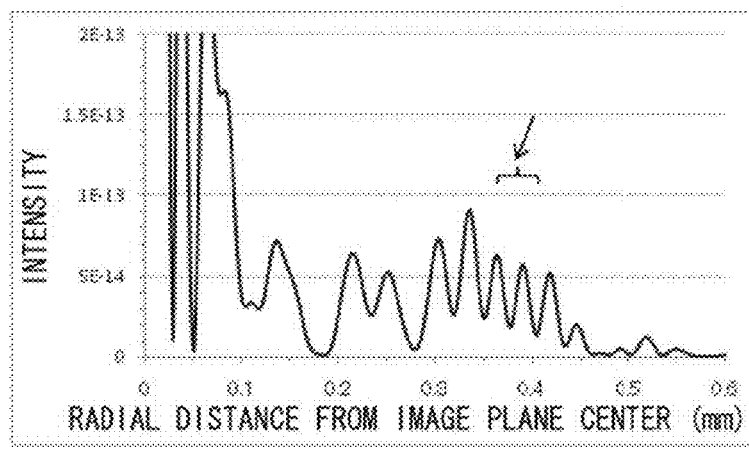
Figure 9:
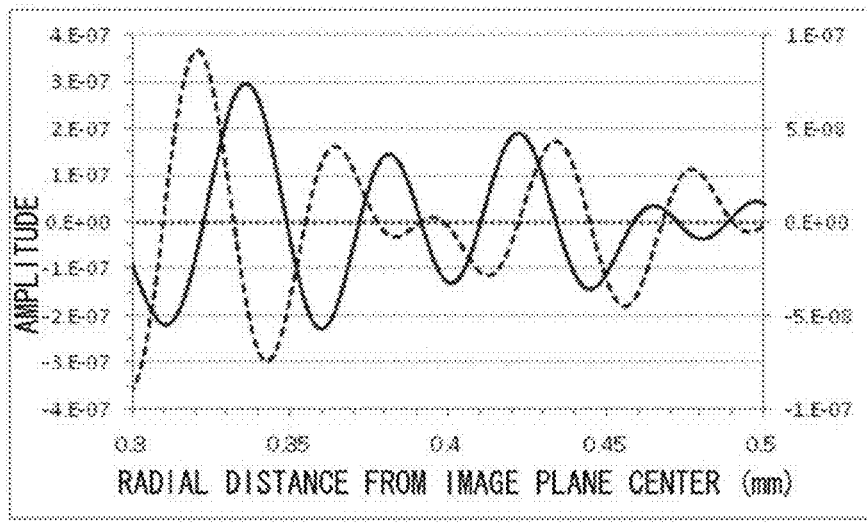
FIG. 9 is a graph for comparing the amplitude distribution deriving from the focal point formation region of the present embodiment with the amplitude distribution deriving from the cancellation region that reduces the aforementioned amplitude distribution.

For the purpose of reducing the halo expansion, a range of amplitude from 0.35 to 0.4 mm in the intensity distribution on the 0th order focal point image plane of the conventional example shown in FIG. 8B was given a special attention, and a group of various constants used in Equation 9 (τ=0) that provide amplitude distribution that can reduce such amplitude were obtained by computer calculation. As a result, a function expressed by Equation 16 below was obtained as an example. FIG. 9 shows amplitude distribution on the 0th order focal point image plane deriving from the cancellation region 30 when the function is assumed to be a phase function. The solid line in FIG. 9 indicates an amplitude function of the focal point formation region 28 in a range of distance from 0.35 to 0.4 mm on the image plane, while the dotted line indicates an amplitude function given by the phase function of Equation 16. It can be seen that waves with nearly inverted amplitudes are generated in the region from 0.35 to 0.4 mm.

$$\phi_c(r) = -0.4\pi \times \sin\left\{\pi \times \left(\frac{r - r_{n-1}}{r_n - r_{n-1}}\right)\right\} \qquad \text{[Equation 16]}$$

The phase function in the cancellation region 30 replaced with the function of Equation 16, that is, a phase profile 26 of the first embodiment of the present invention is shown in FIG. 6A. FIG. 8A shows a calculation result of intensity distribution on the 0th order focal point image plane in the first embodiment of the present invention. FIG. 8A reveals that the intensity of the side-band peaks in the range of the position on the image plane from 0.35 to 0.4 mm is reduced to about ½ to ⅓. Thus, it is observed that the halo expansion is reduced. On the contrary, the intensity of the peaks near the position on image plane at around 0.3 mm is slightly up, but the intensity of the group of peaks near the center does not seem to have a significant impact on the halo formation unless it gets too large, because reduction in the expansion of halos is considered more important.

Also, in order to examine the impact of introducing such cancellation region 30 on the far and near vision, intensity distribution on the optical axis was calculated (FIGS. 10A, 10B) for both cases of including the cancellation region 30 and not including the cancellation region 30 to replace it with a refractive region equivalent thereto. Since there is virtually no difference in the intensity ratio of far and near vision between them, it is found that even when the cancellation region 30 is partially overlapping on the pupil diameter when the brightness gets slightly lower than that of a photopic environment, almost the same far and near vision can be obtained as without the cancellation region 30. Therefore, it is observed that the cancellation region 30 can specifically reduce only the halo without compromising the far and near vision not only in a photopic environment but also in a slightly darker environment.

An embodiment of the present invention has been described in detail above, but it is just an example and the present invention should not be interpreted in a way limited by such specific descriptions. Other aspects that can favorably be used in the present invention are described below, but it should be noted that the present invention is not limited to those aspects. In the following paragraphs, detailed descriptions of substantially the same members and parts as those of the embodiments described above are omitted by assigning the same numerals to the equivalent components.

Second Embodiment

As shown in Table 2, the phase function for the present embodiment was determined in the same way as in the previous embodiment as a phase function with a little wider zone width than that of the cancellation region 30 while keeping the focal point formation region 28 as it is. As a result, the function given by Equation 17 below was obtained.

TABLE 2

[Second embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.738918 | 0 | −1.57079 | 1.57079 | 0.5 |
| | 2 | 1.044988 | 0.738918 | −1.57079 | 1.57079 | 0.5 |
| | 3 | 1.279844 | 1.044988 | −1.57079 | 1.57079 | 0.5 |
| | 4 | 1.477836 | 1.279844 | −1.57079 | 1.57079 | 0.5 |
| | 5 | 1.652271 | 1.477836 | −1.57079 | 1.57079 | 0.5 |
| Cancellation region | 6 | 1.826706 | 1.652271 | [Equation 17] | | — |

$$\phi_c(r) = -\pi \times \sin\left\{4\pi \times \left(\frac{r-r_{n-1}}{r_n-r_{n-1}}\right)^2\right\} - \quad \text{[Equation 17]}$$

$$0.5\pi \times \sin\left\{2\pi \times \left(\frac{r-r_{n-1}}{r_n-r_{n-1}}\right)^2\right\}$$

Figure 11:
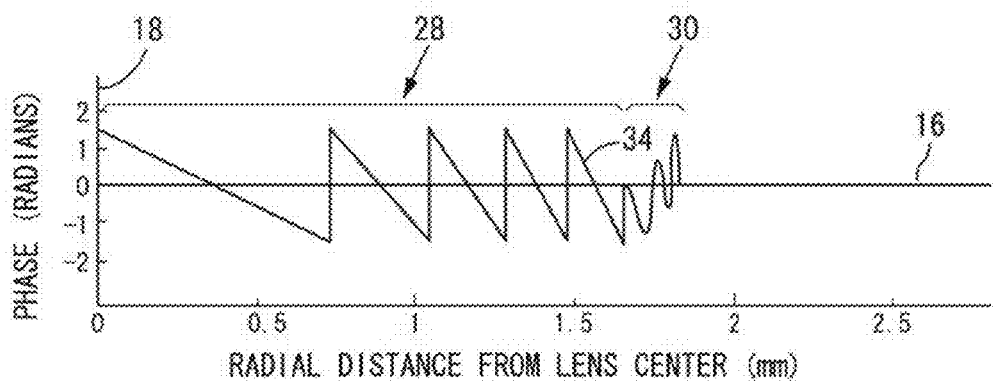
FIG. 11 is a phase profile of a second embodiment of the present invention.
Figure 12:
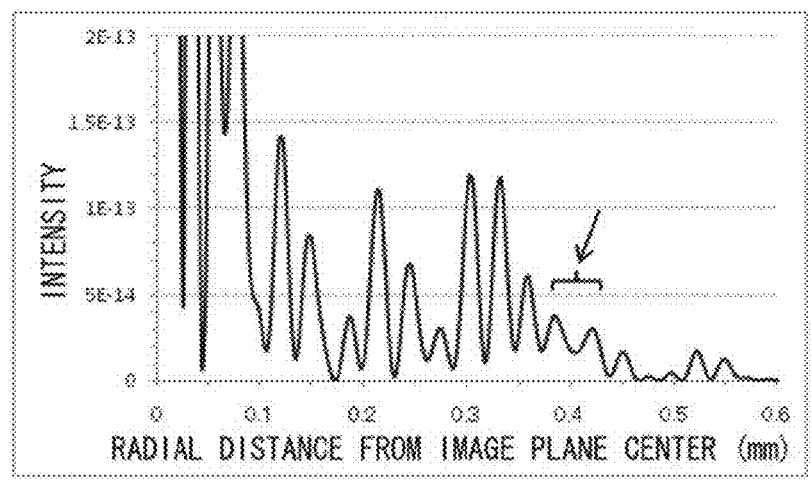
FIG. 12 is a simulation result of the image plane intensity distribution at the focal point position of 0th order diffracted light of the present embodiment.
Figure 13:
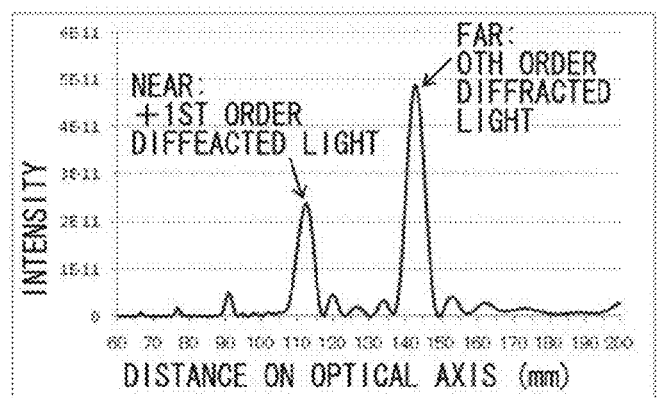
FIG. 13 is a result of simulation of intensity distribution on the optical axis of the present embodiment.
Figure 14:
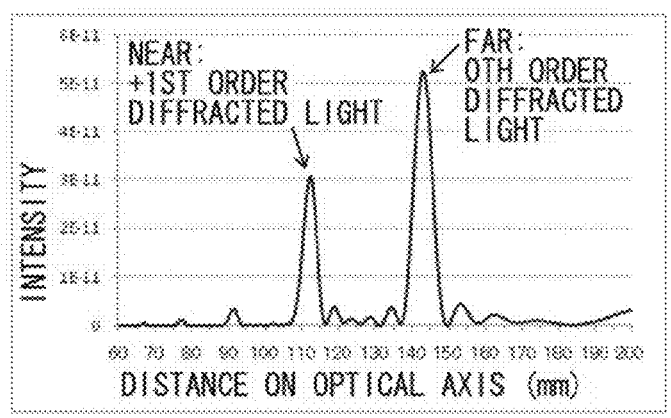
FIG. 14 is a result of simulation of intensity distribution on the optical axis of a comparative example.

The phase function in the cancellation region 30 replaced with the function of Equation 17, that is, a phase profile 34 of the second embodiment of the present invention is shown in FIG. 11. FIGS. 12 and 13 show the calculation results of intensity distribution on the 0th order focal point image plane of the present embodiment and intensity distribution on the optical axis, respectively. Also, as a comparative example, a result of intensity distribution on the optical axis in case of not including the cancellation region 30 and having it replaced by a refraction region is shown in FIG. 14.

FIG. 12 indicates that the peaks of side-bands that emerged in the peripheral region on the image plane (FIG. 8B) at around 0.37 to 0.42 mm are reduced. Also, FIGS. 13 and 14 show that the cancellation region 30 of the present embodiment has almost no impact on the far vision. All of these indicate that the reduction of halos is possible without compromising the quality of far and near vision by setting such cancellation region 30.

Third Embodiment

Figure 15B:
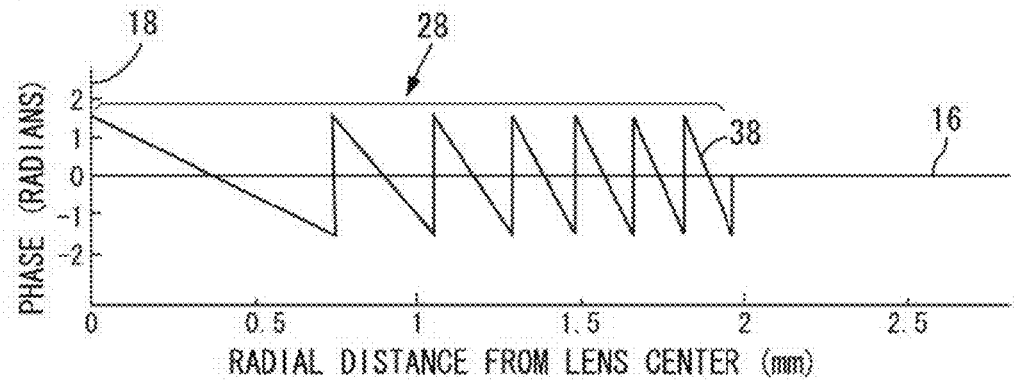
Figure 16A:
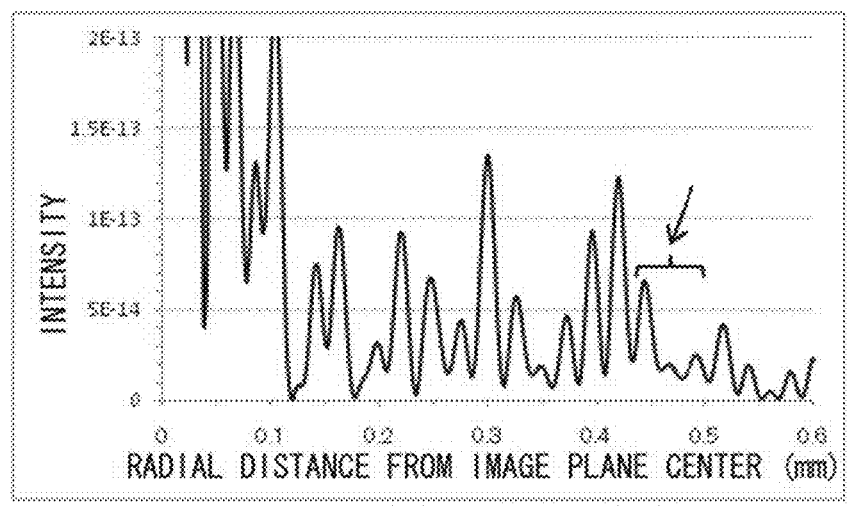
FIGS. 16A and 16B are graphs for comparing simulation results of the image plane intensity distribution at the focal point position of 0th order diffracted light of the present embodiment with those of a comparative example.
Figure 16B:
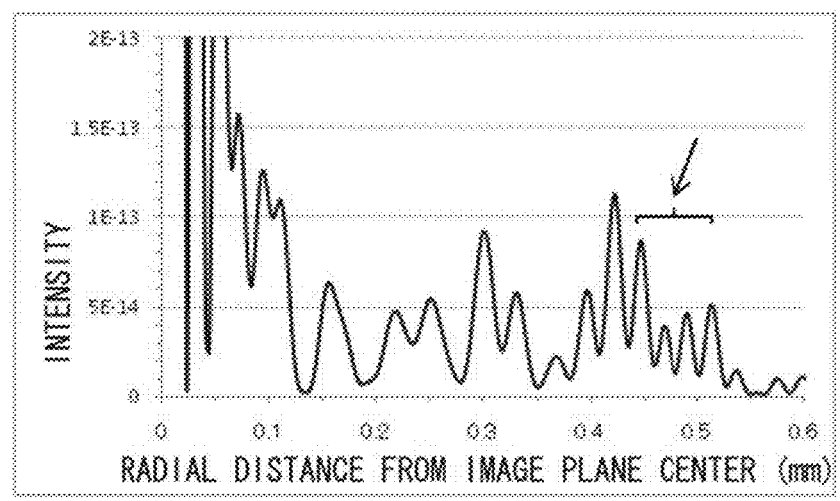

As shown in Table 3, the number of diffraction zones in the focal point formation region 28 of the first embodiment was increased to design a diffraction-type multifocal lens with its zones 1 to 7 made to be diffraction zones following the Fresnel pitch rules. Such diffraction-type multifocal lens is designed to have a constant energy allocation ratio between far and near distances either in daytime brightness or in a slightly darker environment. A phase profile 38 of this focal point formation region 28 is shown in FIG. 15B and intensity distribution on the 0th order focal point image plane is shown in FIG. 16B. It is observed that the side-band distribution on the far focal point image plane of this case is further extended toward the periphery compared to the distribution in FIG. 8B due to the increased number of diffraction zones. Now, in order to reduce the side-band intensity on the image plane at the position around 0.45 to 0.52 mm, a group of constants used in Equation 9 that provide amplitude distribution capable of reducing such amplitude were obtained by computer calculation. As a result, a function expressed by Equation 18 below was obtained.

$$\phi_c(r) = -0.35\pi \times \sin\left\{2\pi \times \left(\frac{r-r_{n-1}}{r_n-r_{n-1}}\right)^2\right\} \quad \text{[Equation 18]}$$

Figure 15A:
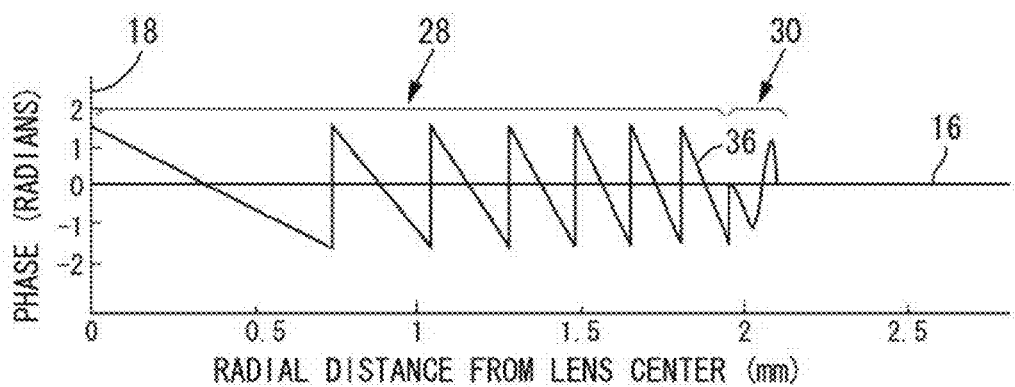
FIGS. 15A and 15B are phase profiles of a third embodiment of the present invention and of a comparative example.
Figure 17A:
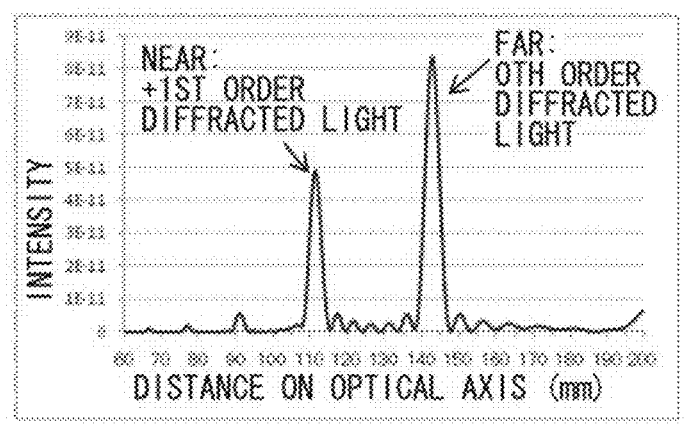
FIGS. 17A and 17B are graphs for comparing a result of simulation of intensity distribution on the optical axis of the present invention with that of the comparative example.
Figure 17B:
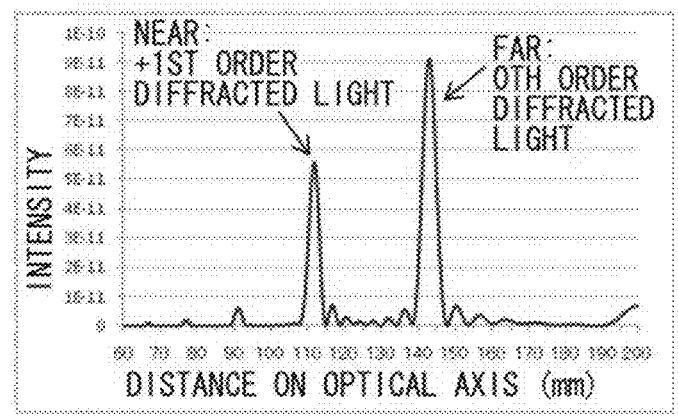

The phase function in the cancellation region 30 replaced with the function of Equation 18, that is, a phase profile 36 of the third embodiment of the present invention is shown in FIG. 15A. FIGS. 16A and 17A show the calculation results of intensity distribution on the 0th order focal point image plane of the multifocal lens including the cancellation region 30 and intensity distribution on the optical axis, respectively. Also, as a comparative example, intensity distribution on the optical axis in case of not including the cancellation region 30 and having it replaced by a refraction region is shown in FIG. 17B.

FIG. 16 indicates that the side-band peaks that had emerged in the peripheral region on the image plane have been reduced when the cancellation region 30 does not exist. Since there is no virtual difference in the intensity distribution on the optical axis, it is implied that setting the cancellation region 30 has almost no impact on the far and near vision. Therefore, it is found possible to reduce the halo at night without compromising the far and near vision in a photopic to mesopic environment.

Fourth Embodiment

Figure 19A:
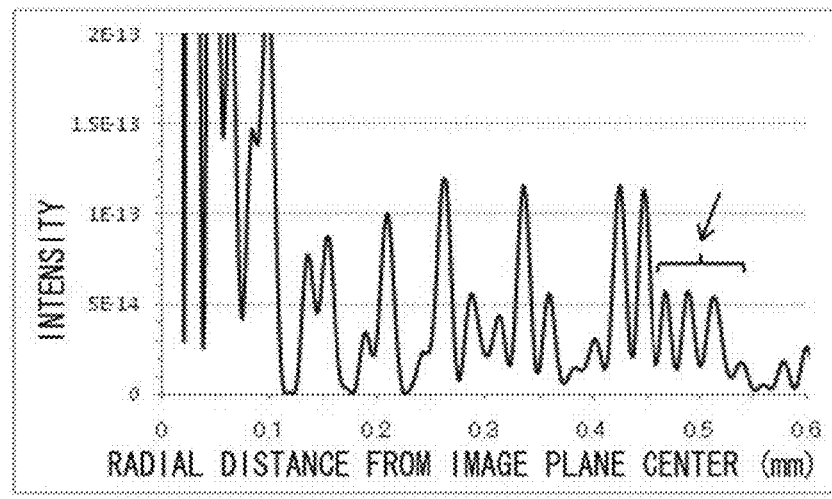
FIGS. 19A and 19B are graphs for comparing simulation results of the image plane intensity distribution at the focal point position of 0th order diffracted light of the present embodiment with those of the comparative example.
Figure 19B:
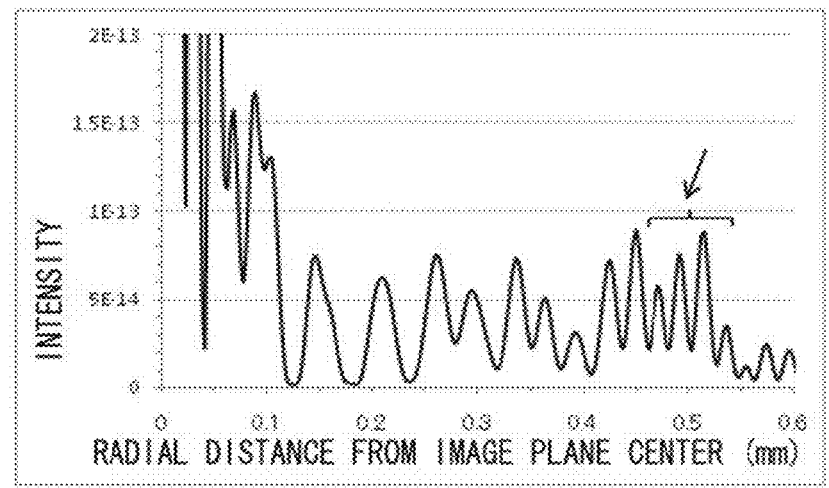

As shown in Table 4, phase cancellation was examined against a multifocal lens with more diffraction zones to make the 1st to 8th zones included in a diffraction structure following the Fresnel pitch rules. Such a diffraction-type multifocal lens is designed to make the intensity ratio of far and near vision almost equal in a darker environment. When the number of diffraction zones is increased to 8th zone, the side-band amplitude distribution has no significant difference from that of the third embodiment described above, but the intensity in the region from about 0.45 to 0.53 mm gets higher (FIG. 19B, pointed by an arrow). In case of such a diffraction-type lens, the brightness around the halo increases at night and objects around the halo are likely to become hardly visible. So, in order to make the region adjacent to 8th zone on the outside the cancellation region 30 and reduce the amplitudes within a range of 0.45 to 0.53 mm among the side-band amplitude distribution, a group of constants used in Equation 9 above that provide amplitude distribution capable of reducing such amplitude were obtained by computer calculation. As a result, a function was obtained as shown in Equation 19.

TABLE 3

[Third embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.738918 | 0 | −1.57079 | 1.57079 | 0.5 |
| | 2 | 1.044988 | 0.738918 | −1.57079 | 1.57079 | 0.5 |
| | 3 | 1.279844 | 1.044988 | −1.57079 | 1.57079 | 0.5 |
| | 4 | 1.477836 | 1.279844 | −1.57079 | 1.57079 | 0.5 |
| | 5 | 1.652271 | 1.477836 | −1.57079 | 1.57079 | 0.5 |
| | 6 | 1.809972 | 1.652271 | −1.57079 | 1.57079 | 0.5 |
| | 7 | 1.954994 | 1.809972 | −1.57079 | 1.57079 | 0.5 |
| Cancellation region | 8 | 2.1 | 1.954994 | [Equation 18] | | — |

TABLE 4

[Fourth embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.738918 | 0 | −1.57079 | 1.57079 | 0.5 |
| | 2 | 1.044988 | 0.738918 | −1.57079 | 1.57079 | 0.5 |
| | 3 | 1.279844 | 1.044988 | −1.57079 | 1.57079 | 0.5 |
| | 4 | 1.477836 | 1.279844 | −1.57079 | 1.57079 | 0.5 |
| | 5 | 1.652271 | 1.477836 | −1.57079 | 1.57079 | 0.5 |
| | 6 | 1.809972 | 1.652271 | −1.57079 | 1.57079 | 0.5 |
| | 7 | 1.954994 | 1.809972 | −1.57079 | 1.57079 | 0.5 |
| | 8 | 2.089976 | 1.954994 | −1.57079 | 1.57079 | 0.5 |
| Cancellation region | 9 | 2.216754 | 2.089976 | [Equation 19] | | — |

$$\phi_c(r) = -0.5\pi \times \sin\left\{2\pi \times \left(\frac{r - r_{n-1}}{r_n - r_{n-1}}\right)^2\right\} \quad \text{[Equation 19]}$$

Figure 18A:
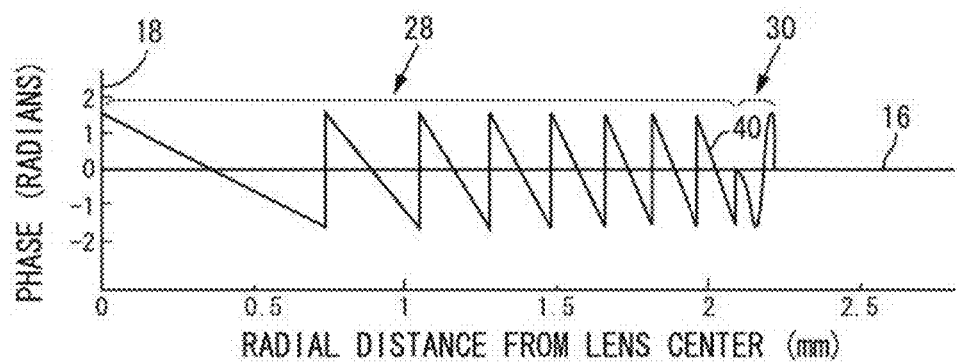
FIGS. 18A and 18B are phase profiles of a fourth embodiment of the present invention and of a comparative example.
Figure 18B:
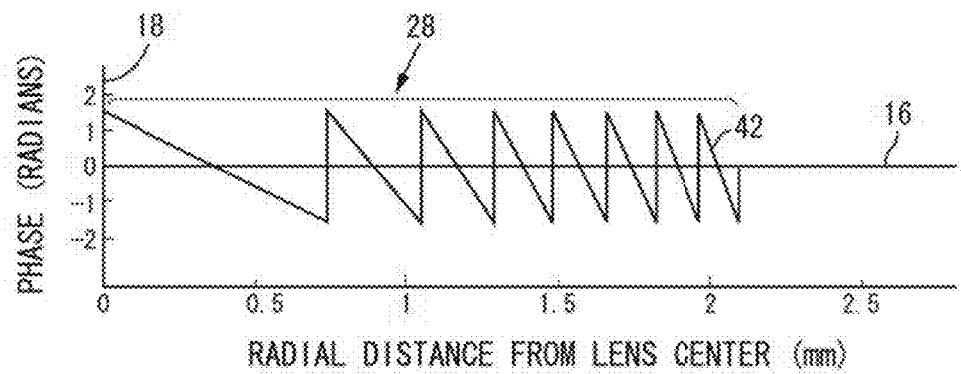

The phase function in the cancellation region 30 replaced with the function of Equation 19, that is, a phase profile 40 of the fourth embodiment of the present invention is shown in FIG. 18A. FIG. 19A shows a calculation result of intensity distribution on the 0th order focal point image plane of the multifocal lens including the cancellation region 30. It is observed that the high-intensity side-band peaks that had emerged in the peripheral region on the image plane have been reduced when the cancellation region 30 does not exist (a phase profile 42 in FIG. 19B). Also, by determining intensity distribution (not shown in the figure) on the optical axis as has been done for all the previous embodiments, it was confirmed that there is virtually no difference in the intensity ratio on the optical axis of far and near vision between the cases with and without the cancellation region 30. Therefore, it is observed that the halo at night can be reduced without compromising the far and near vision in a photopic to mesopic environment by means of setting such cancellation region 30. The embodiments described above indicate that the cancelable phase function can be determined by obtaining a function that fits the amplitude distribution thereof By the way, if the phase function for cancellation is a blaze-type phase function, it is possible to estimate the phase function for cancellation without relying on the fitting calculation described above. In other words, since the side-band distribution is based on the composite amplitudes of all diffraction zones, once a zone contributing to the most outstanding amplitude among the side-band distribution is found, the halo reduction can be achieved by cancelling such amplitude.

Another method to estimate a phase function for cancelling amplitudes in a specific zone will be described below. Generally, if a phase function is expressed by a linear first-degree equation such as Equation 2 above, Equation 14 becomes integrable when $\phi(r)$ in Equation 2 is substituted for Equation 14 as $\phi_c(r)$ in a form including the phase shift $\tau$ so as to be expressed by Equation 20 below. Only the real part as the amplitude function is shown here. Such equation can be applied commonly to the cancellation region 30 and the focal point formation region 28. Therefore, $E_c(\rho)$ of Equation 14 is expressed in a general form of $E(\rho)$ in Equation 20.

$$E(\rho) = \quad \text{[Equation 20]}$$

$$E_c \times \cos\left\{\frac{k\rho^2 - k(r_n + r_{n-1})\rho}{2f} + \frac{\phi_n + \phi_{n-1}}{2} + \tau + kf\right\} \times$$

$$\text{Sinc}\left\{\frac{\phi_n - \phi_{n-1}}{2} - \frac{k(r_n - r_{n-1})\rho}{2f}\right\} \times (r_n - r_{n-1})$$

$\phi_n$: Phase at the position on the outer radius of the $n^{th}$ diffraction zone
$\phi_{n-1}$: Phase at the position on the inner radius of the $n^{th}$ diffraction zone
$r_n$: Outer radius of the $n^{th}$ diffraction zone
$r_{n-1}$: Inner radius of the $n^{th}$ diffraction zone
$\rho$: Position in the radial direction measured from the center of the 0th order focal point image plane k: Wavenumber. Defined as $k=2\pi/\lambda$
f: Focal length of zero-diffracted light
$E_0$: Intrinsic amplitude value
r: Distance from the lens center in the radial direction
$\tau$: Phase shift If any two zones have the same interval (width) and phase constant, the form of the Sinc function on the right side of Equation 20 turns out to be the same for both zones. Therefore, the wave interference behavior of light emitted from both zones ends up being dominated by the cosine function on the right side of the equation. Assuming that a specific zone range of the focal point formation region 28 is $r_{p-1}$ to $r_p$ and the cancellation region 30 is $r_{n-1}$ to $r_n$, it is observed that the amplitudes intensify each other at a position on the image plane $\rho_q$ corresponding to the order q expressed by Equation 21 below.

$$\rho_q = \frac{2q\pi f}{k(r_n - r_p)} \quad \text{[Equation 21]}$$

k: Wavenumber. Defined as $k=2\pi/\lambda$
q: Order. Integer except zero.
$\rho_q$: Position where amplitudes from zones with equal intervals intensify each other at the 0th order focal point image plane
$r_n$: Outer radius of the cancellation region
$r_p$: Outer radius of a specific zone in the focal point formation region If a cancellation region 30 having a blaze-type phase function is set at a position adjacent to the focal point formation region 28 composed of five diffraction zones shown in the first embodiment and the interval of the cancellation region 30 is made equal to the interval of each zone in the focal point formation region 28, the positions where the two cosine functions intensify each other are as shown in Table 5 below.

TABLE 5

Positions where cosine functions intensify each other ($\rho_q$)

| q | Cancellation region interval = 2nd zone interval | Cancellation region interval = 3rd zone interval | Cancellation region interval = 4th zone interval | Cancellation region interval = 5th zone interval |
|---|---|---|---|---|
| 1 | 0.085385 | 0.128419 | 0.209401 | 0.447083 |
| 2 | 0.170770 | 0.256838 | 0.418803 | 0.894167 |
| 3 | 0.256156 | 0.385258 | 0.628205 | 0.341250 |
| 4 | 0.341541 | 0.513677 | 0.837600 | 1.788334 |
| 5 | 0.426926 | 0.642097 | 1.047009 | 2.235417 |

Figure 20:
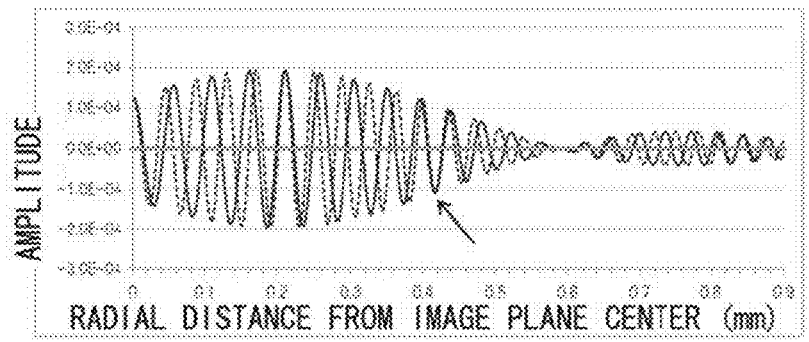
FIG. 20 is amplitude distributions at 0th order focal point image plane from two orbicular zones wherein the interval in the cancellation region is made equal to that of the fourth zone in the focal point formation region in the first embodiment.
Figure 21:
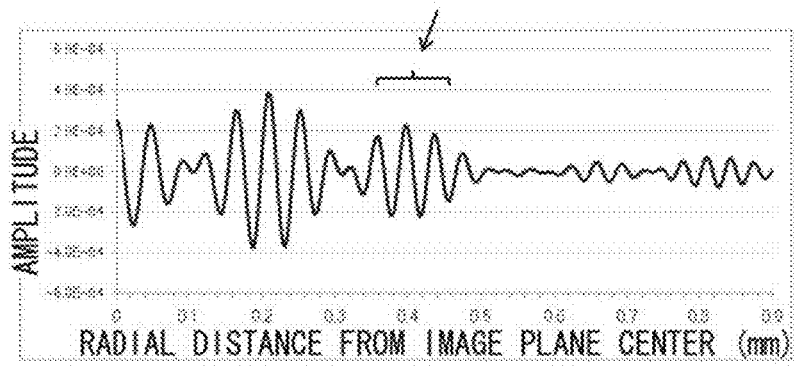
FIG. 21 is a composite amplitude function of the two orbicular zones in FIG. 20.

Assuming that the amplitude peak at the position where p is about 0.41 mm on the image plane is to be reduced in the amplitude distribution deriving from the focal point formation region 28 in the first embodiment, a combination of the diffraction zone and the cancellation region 30 to intensify each other at a point nearest to the position under a condition of smaller order q is reached when the interval of the cancellation region 30 becomes equal to the 4th zone interval. Under such conditions, the amplitudes at the position intensify each other to increase the composite amplitude. The relation between the amplitude functions of both zones are shown in FIG. 20 (two amplitude functions shown overlapped) and FIG. 21 (composite amplitude function). In FIG. 20, the solid line indicates the amplitude of the 4th zone and the dotted line indicates the amplitude deriving from the cancellation region 30. It is observed that two amplitudes intensify each other at the location marked by the arrows. However, if the amplitude phases of the two regions are shifted from each other by half a wavelength, the amplitudes blaze-type, it is understood that the cancellation effect takes place by means of setting the interval of the cancellation region 30 equal to that of the target zone and by giving the phase shift τ (FIG. 25). Thus, the cancellation effect can be also produced by setting a blaze-type phase function and shifting the entire phase function relative to the datum line.

TABLE 6

[Fifth embodiment]

Figure 22:
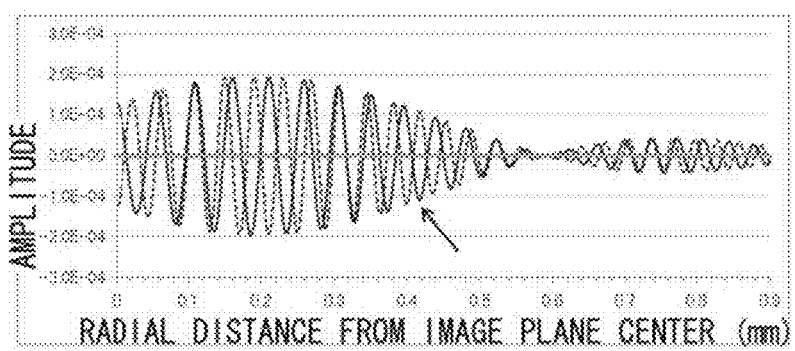
FIG. 22 is amplitude distributions of the two orbicular zones when the phase shift in the cancellation region is set at $(2u-1)\pi$.
Figure 23:
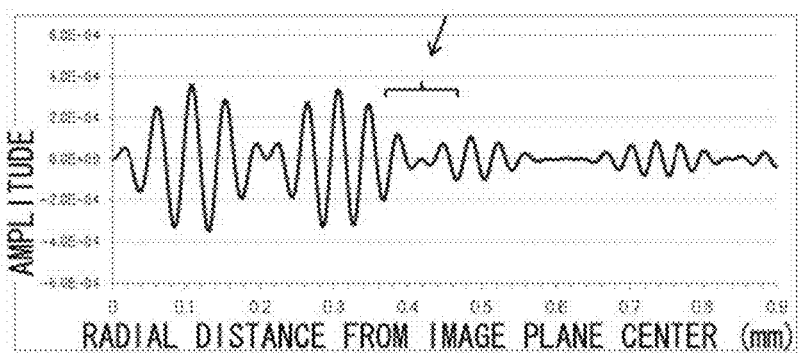
FIG. 23 is a composite amplitude function of the two orbicular zones in FIG. 22.

| Region | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|
| Focal point formation region | 1 | 0.738918 | 0 | −1.57079 | 1.57079 | 0.5 | 0 |
| | 2 | 1.044988 | 0.738918 | −1.57079 | 1.57079 | 0.5 | 0 |
| | 3 | 1.279844 | 1.044988 | −1.57079 | 1.57079 | 0.5 | 0 |
| | 4 | 1.477836 | 1.279844 | −1.57079 | 1.57079 | 0.5 | 0 |
| | 5 | 1.652271 | 1.477836 | −1.57079 | 1.57079 | 0.5 | 0 |
| Cancellation region | 6 | 1.850263 | 1.652271 | −4.71238 | −1.57079 | 0.5 | −π | cancel each other, instead of intensifying each other, to become zero. That means the amplitude can be reduced at this particular position. FIGS. 22 and 23 show the relation between the amplitude functions of both zones in this case. Their amplitudes get in opposite phases at the position marked by the arrows in FIGS. 22 and 23 to cancel each other. Here, in an attempt to shift the phase of the cancellation region 30 by means of substituting the phase shift τ in Equation 10 at τ=(2u−1) π (u is an integer) for the phase function of the cancellation region 30, the amplitudes deriving from the cancellation region 30 take equal values with the positive and negative signs inverted to reduce the composite amplitude at the position on the image plane, thereby resulting in reducing the overall amplitude of the diffraction zone. The condition of smaller order q is a condition for selecting a larger amplitude at the corresponding position, that is, a condition added to make the cancellation more effective when the phase shift is introduced. An embodiment that uses such characteristics is described below.

Fifth Embodiment

Figure 24:
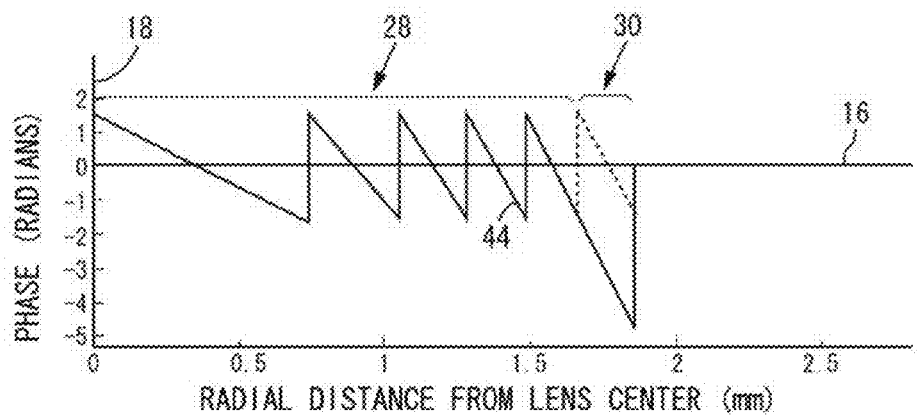
FIG. 24 is a phase profile of a fifth embodiment of the present invention.
Figure 25A:
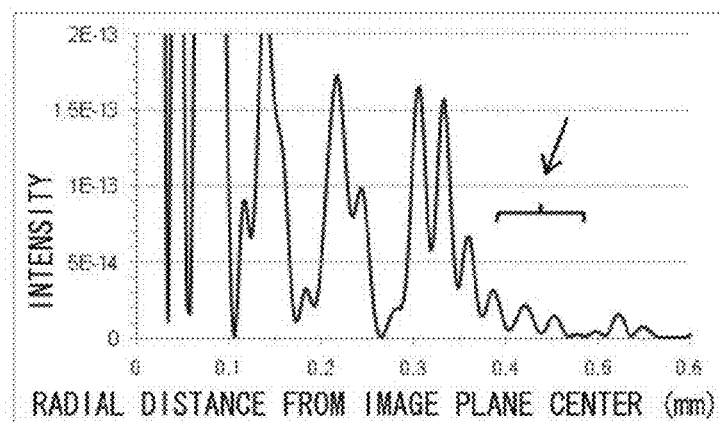
FIGS. 25A and 25B are graphs for comparing simulation results of the image plane intensity distribution at the focal point position of 0th order diffracted light of the present embodiment with those of a comparative example.
Figure 25B:
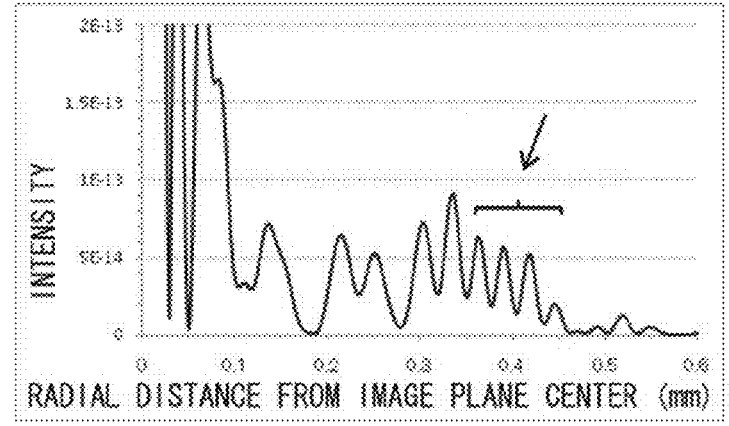

As shown in Table 6, a fifth embodiment of the present invention has the same focal point formation region 28 as that of the first embodiment (FIG. 6A), but the phase function of the cancellation region 30 is changed to a blaze-type at h=0.5 and its interval is made equal to that of the 4th zone of the focal point formation region 28. The symbols $\phi_n$ and $\phi_{n-1}$ indicate values after the phase shift τ is introduced. If the phase shift τ of the cancellation region 30 is set at −π, a phase profile 44 turns out to be as shown in FIG. 24. The dotted-line portion in the cancellation region 30 of the figure indicates a blaze with no phase shift, and by setting the phase shift τ at −π, the blaze drops down below the datum line in the figure so as to make the cancellation region 30. By determining intensity distribution on the 0th order focal point image plane when the cancellation region 30 is included, it is observed that the intensity of the group of peaks around ρ=0.38 to 0.42 mm (FIG. 25B) generated by the focal point formation region has been reduced as shown in FIG. 25A. As can be seen in such an example where the phase function of the cancellation region 30 is changed to a The diffraction-type lens with equal pitches of diffraction zone is useful as a multifocal ophthalmic lens because of its multi-focus forming function similar to that of a diffraction-type lens with the Fresnel pitch. The cancellation effect can be applied to the focal point formation region 28 having such equal-pitch zones. Since all the terms of Sinc function in the amplitude function in Equation 20 turn out to be in the same form even when the equal pitch zones having the blaze-type phase function appear in succession, the wave interference behavior will be dominated by the cosine function term. Let the pitch of the equal pitch zone be Δr and assuming the zone to be arranged in succession, the position where amplitudes of each zone intensify each other is given by Equation 22.

$$\rho_q = \frac{2q\pi f}{k\Delta r} \quad \text{[Equation 22]}$$

Figure 26A:
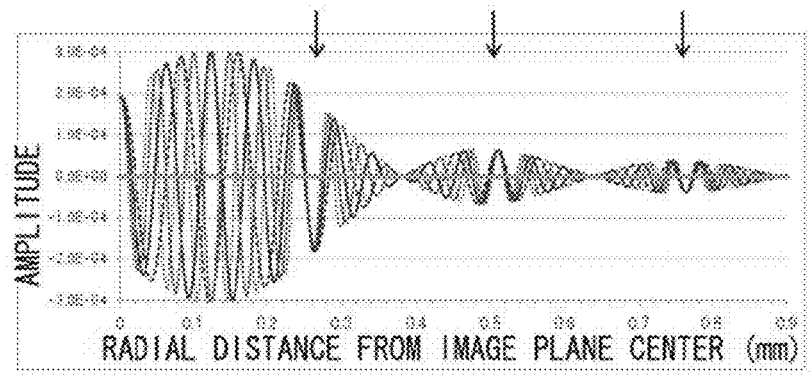
FIGS. 26A-26C are graphs suitable for explaining amplitude functions of the orbicular zones in an equal pitch relation.
Figure 26B:
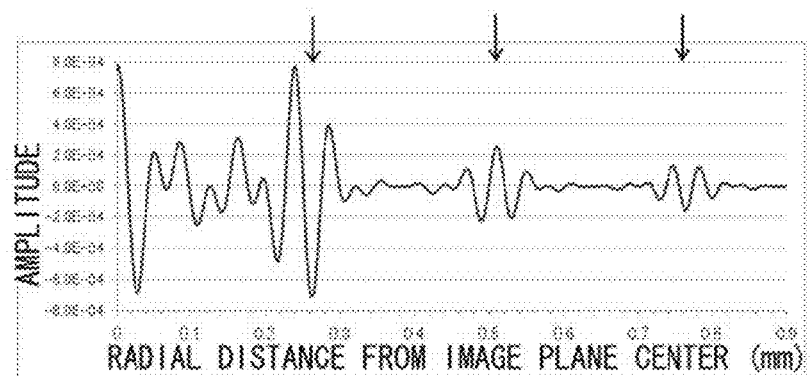
Figure 26C:
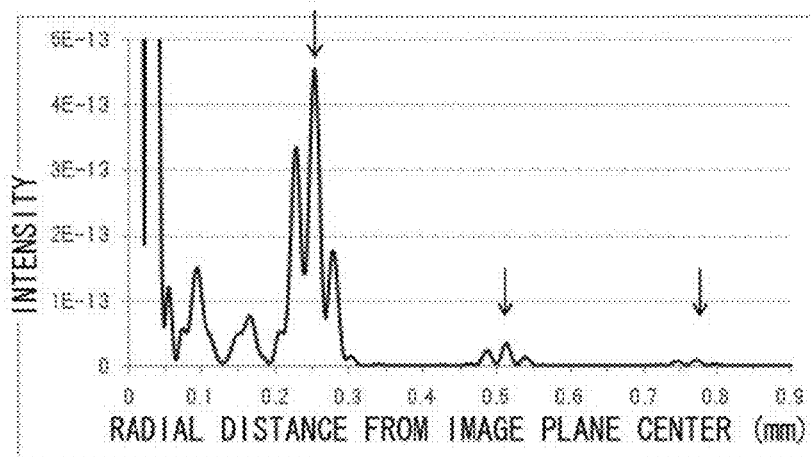

$\rho_q$: Position where amplitudes from zones with equal pitches intensify each other at the 0th order focal point image plane
q: Order. Integer except zero.
f: Focal length of 0th order diffracted light
k: Wavenumber. k=(2π)/λ (wavelength of light)
Δr: Pitch of equal-pitch zone
FIG. 26A shows amplitude functions on the 0th order focal point image plane from the respective zones in the equal-pitch region of the diffraction zone where the 1st and 2nd zones shown in Table 7 are in a Fresnel-pitch relation that results in an addition power of 2 Diopter and the 3rd to 5th zones are in an equal-pitch relation. FIG. 26A reveals that the phases of the amplitude function intensify each other at the position on the image plane expressed by Equation 22 (marked by arrows in FIG. 26A). Meanwhile, FIG. 26B shows that the waves interfere with and cancel each other in other regions. Therefore, intensity distribution of such diffraction zone turns out to be characteristic as shown in FIG. 26C with the peaks appearing at positions where the amplitude functions intensify each other and only with low noise in other regions. The vertical scale of FIG. 26C is reduced to two-fifth of that of the previous embodiments in order to show the overall configuration of the side-band peaks.

TABLE 7

[Sixth embodiment]

| Region | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|
| Focal point formation region | 1 | 0.738918 | 0 | −1.57079 | 1.57079 | 0.5 | 0 |
| | 2 | 1.044988 | 0.738918 | −1.57079 | 1.57079 | 0.5 | 0 |
| | 3 | 1.351057 | 1.044988 | −1.57079 | 1.57079 | 0.5 | 0 |
| | 4 | 1.657127 | 1.351057 | −1.57079 | 1.57079 | 0.5 | 0 |
| | 5 | 1.963197 | 1.657127 | −1.57079 | 1.57079 | 0.5 | 0 |
| Cancellation region | 6 | 2.269267 | 1.963197 | −4.71238 | −1.57079 | 0.5 | −π |

If the interval of the cancellation region 30 is made equal to pitch of the equal-pitch zone as described in the fifth embodiment, the amplitude functions of the cancellation region 30 overlap to intensify each other at the same position. Therefore, the amplitude function of the cancellation region 30 is inverted between positive and negative values when the phase shift $\tau=(2u-1)\pi$ (u is an integer) is substituted for the phase function of the cancellation region 30, thereby reducing the amplitude of the focal point formation region 28. Especially in case of including such multiple equal-pitch zones, the amplitudes intensify each other only at specific regular positions, which leads to an advantage of being able to reduce the amplitude at those positions in a selective and effective manner. The following embodiment shows the cancellation effect against the diffraction zone composed of such equal-pitch zones.

Sixth Embodiment

Figure 27A:
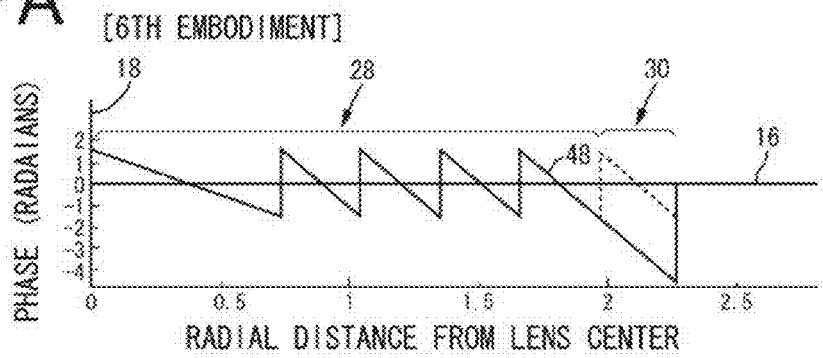
FIGS. 27A and 27B are phase profiles of a sixth embodiment and of a comparative example.
Figure 27B:
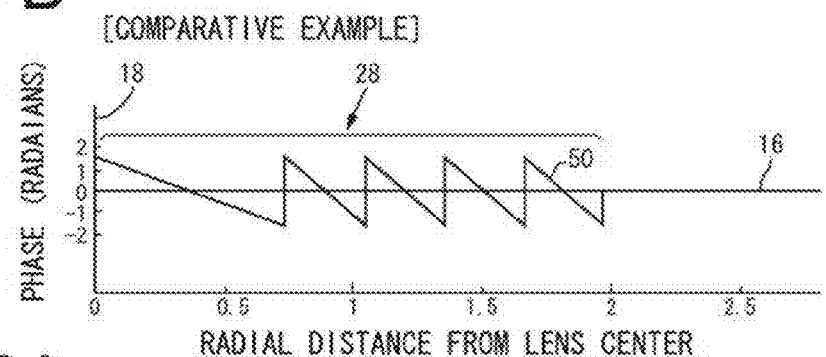
Figure 28A:
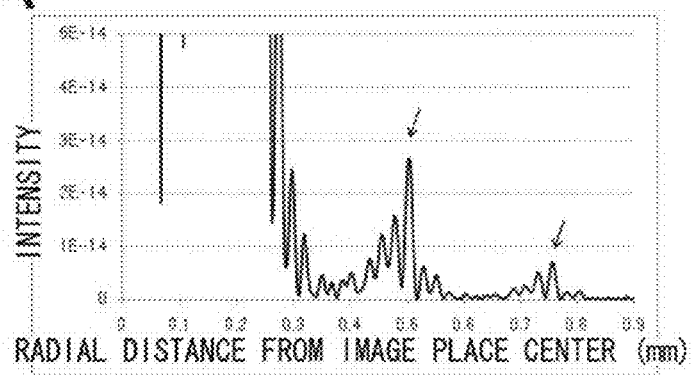
FIGS. 28A and 28B are graphs for comparing simulation results of the image plane intensity distribution at the focal point position of 0th order diffracted light of the present embodiment with those of the comparative example.
Figure 28B:
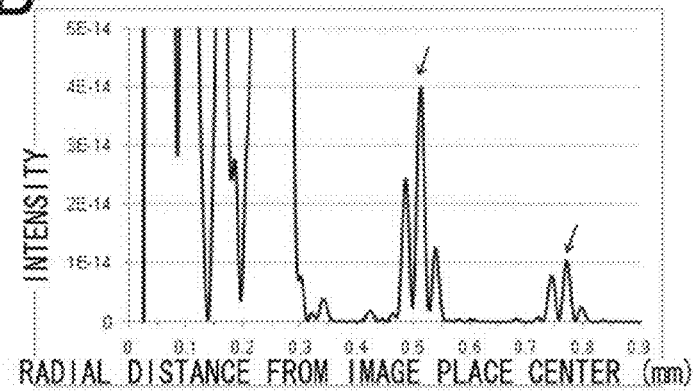

FIG. 27A shows a phase profile 48 (Table 7) as a sixth embodiment of the present invention together with a phase profile 50 (FIG. 27B) as a comparative example. The cancellation region 30 having an interval equal to pitch of the equal-pitch region of the focal point formation region 28 is set for the focal point formation region 28 of the comparative example, and the phase constant of the blaze is set at h=0.5, and the phase shift at τ=−π. As is the case with the fifth embodiment, the dotted-line portion in the cancellation region 30 indicates a blaze with no phase shift, and by setting the phase shift τ at −π, the shift was given to make the cancellation region 30 (solid line portion). FIG. 28 shows intensity distribution on the 0th order focal point image plane of the present embodiment (FIG. 28A) together with a comparative example thereof (FIG. 28B). FIG. 28B indicates that the peaks of the focal point formation region 28 having equal-pitch zones appear at positions (marked by arrows) where the amplitudes intensify each other as described above. Also, as shown in FIG. 28A, it was found that the peak intensity was reduced to about two-thirds to one-half by setting the cancellation region 30 with the phase shift at τ=−π. The vertical scale of the image-plane intensity distribution of the present embodiment through the ninth embodiment is shown quadrupled compared to those of the preceding embodiments.

As to the present embodiment, contact lenses were actually manufactured to verify the halo reduction effect. More specifically, a contact lens was produced for each of the phase profile 50 shown in FIG. 27B composed solely of the focal point formation region 28 and the phase profile 48 shown in FIG. 27A that also includes the cancellation region 30, and night photos of these contact lenses were taken. The diffraction structure was made as a relief structure based on the phase profile with the refractive indices of the lens's base material and the medium set at 1.438 and 1.335, respectively, which was converted into a relief configuration assuming the wavelength of light to be 546 nm.

The contact lenses produced this time are hydrogel soft contact lenses with the water content of 37.5% mainly composed of 2-hydroxyethyl methacrylate with the lens diameter of 14 mm, the optical part diameter 8 mm, and the base curve at 8.5 mm, and the focal point formation region 28 and the cancellation region 30 were set on the back surface thereof. To take actual photos of halos at night, the prototype contact lenses were soaked in physiological saline filled in a glass cell, which were placed in front of the camera lens to take night photos of the light source at far distance. The photos were taken under the condition of open aperture of the camera lens assuming the situation where the pupil diameter is increased during night hours. Since the conditions of the prototype contact lenses to be taken in photos and the image shooting conditions are the same as those of this time, they are omitted hereinafter.

Figure 29A:
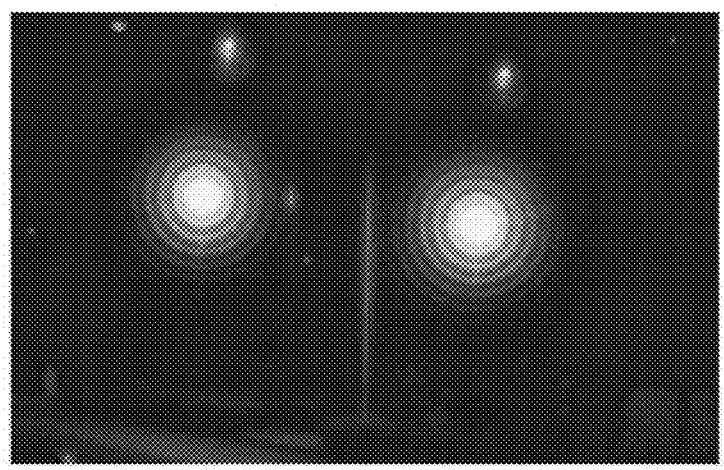
FIGS. 29A and 29B are actual photos of halos of the present embodiment and of the comparative example.
Figure 29B:
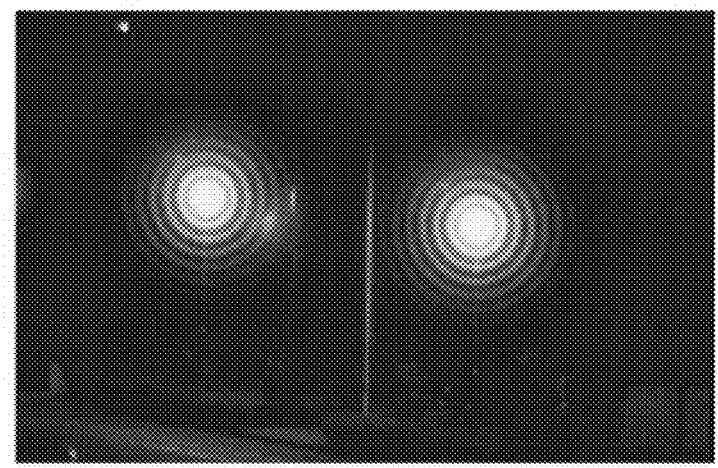

FIG. 29B shows an actual photo of halos of contact lenses without the cancellation region 30. FIG. 29A shows an actual photo of halos of contact lenses with the cancellation region 30 set up. These photos of halos reveal that the lens with the cancellation region 30 has lower ring brightness than the lens without it on the whole and has a less conspicuous glaring expanse around the rings. This indicates that setting the cancellation region 30 is useful in reducing the halo formation.

The interval of the cancellation region 30 is preferably set equal to pitch of the equal-pitch zone of the focal point formation region 28 in terms of maximizing the cancelling effect. However, it should be noted that this is not a requirement since using a different interval as described below can bring the same cancelling effect.

Figure 30A:
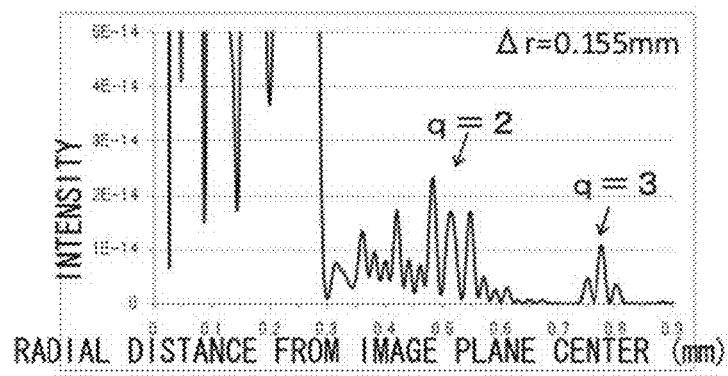
FIGS. 30A-30C are graphs showing interval dependence in the cancellation region found from simulation results of the image plane intensity distribution at the focal point position of 0th order diffracted light of the present embodiment.
Figure 30B:
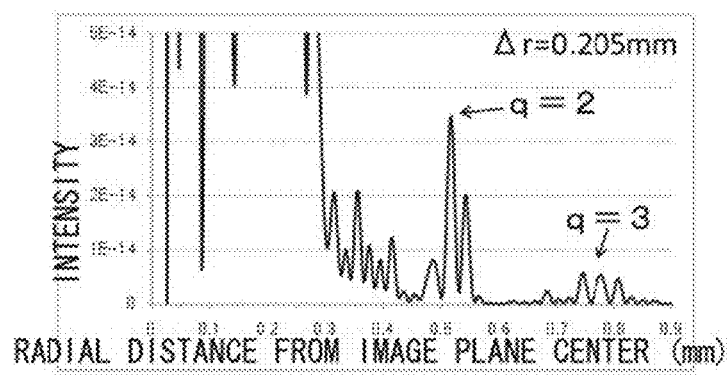
Figure 30C:
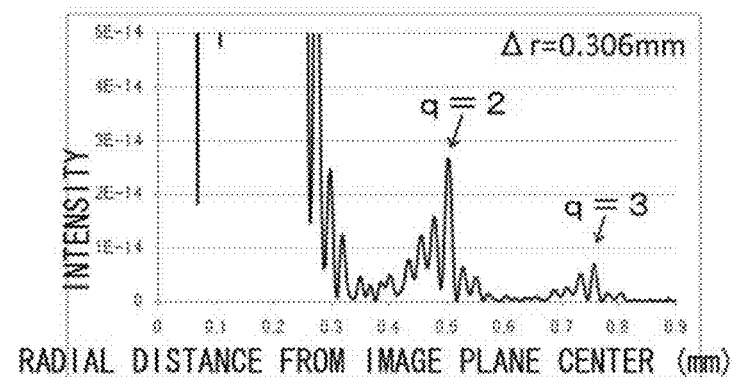

As a couple of examples, the cancelling effects of the sixth embodiment of the present invention are shown in FIGS. 30A and 30B keeping the phase constant and phase shift of the cancellation region 30 as they are and simply changing the interval. The sixth embodiment of the present invention is shown in FIG. 30C. FIG. 30A shows a case with about half the interval of FIG. 30C at 0.155 mm where the peak intensity is reduced at q=2, although not quite reduced at q=3. FIG. 30B shows a case with the interval of 0.205 mm where the peak intensity has clearly been reduced at q=3, although not quite reduced at q=2. Thus, the identity of the Sinc function form, which is an assumption for obtaining Equation 22 that represents the position of mutual intensification, is lost between zones with different intervals, and consequently, the periodic intervals and the amplitude positions tend to differ. However, since the characteristics of the cosine function are still reflected in the distribution even with a different form of Sinc function, the peak intensity can be cancelled at a position of order q, which is equivalent to the lowest common multiple of intervals divided by the interval at issue. For example, in case of FIG. 30B with the interval of 0.205 mm, the position of order q=3 is calculated by dividing the lowest common multiple of about 0.6 by the interval 0.205 mm. Therefore, the interval does not always have to be constant and can be changed in the cancellation region 30 depending on the situations.

The degree of freedom in setting such intervals in the cancellation region 30 can also be applied to the setting of the cancellation region 30 for the Fresnel pitch in the fifth embodiment of the present invention. Also, the phase constant h does not have to be equal between the focal point formation region 28 and the cancellation region 30, but it can be set in consideration of the intended vision, namely, which vision should be given priority among visions for far, near, and intermediate regions in a photopic or mesopic environment, especially in the focal point formation region 28. Moreover, the phase constant h can be different in the cancellation region 30. Different constants h result in different forms of Sinc function, but since the periodic interval of Sinc function is larger than that of cosine function, the period of amplitude distribution does not undergo any change as long as the extrema of Sinc function are within the same extrema region of either positive or negative. In other words, the phase constant h of the cancellation region 30 can be set arbitrarily to exert the cancellation effect. In the method of exerting the cancellation effect by reversing the blaze inclination, which will be described later, the extrema of Sinc function are sometimes changed on purpose so that the phase constant can be set at a value which is able to exhibit such characteristics, namely, the characteristics which exert the cancellation effect by changing the extrema.

In all of the previous embodiments, examples were shown where the cancellation region 30 lies adjacent to the focal point formation region 28. Now, the phase cancellation effect will be described in the embodiments below in case where the cancellation region 30 is set at a position away from the focal point formation region 28. The advantage of having the cancellation region 30 away from the focal point formation region 28 is being able to reduce the impact of the cancellation region 30 on photopic or mesopic vision.

Seventh Embodiment

Figure 31A:
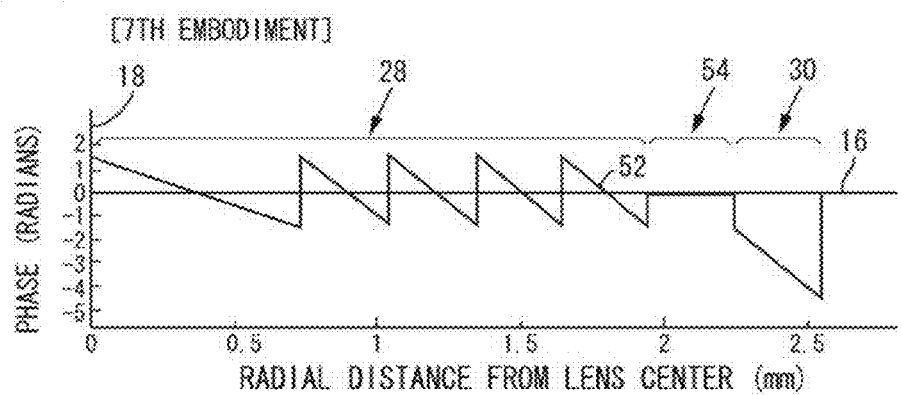
FIGS. 31A-31D are phase profiles of a seventh embodiment of the present embodiment and of a comparative example.
Figure 31B:
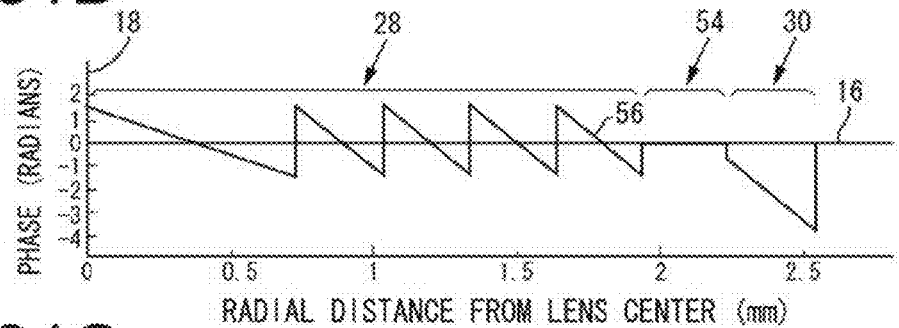
Figure 31C:
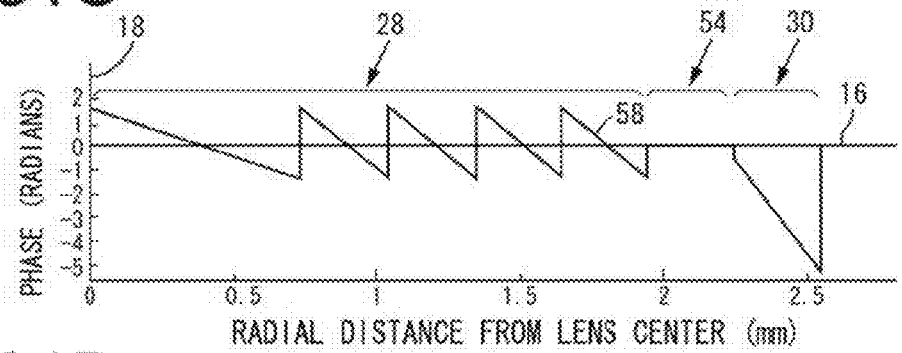
Figure 31D:
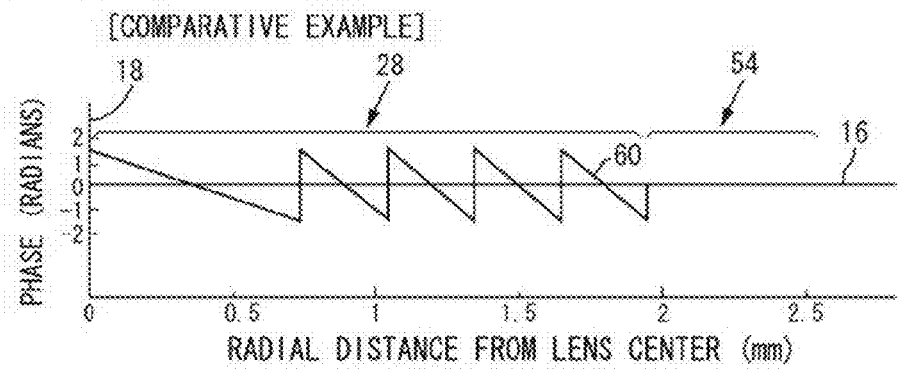

The phase profiles 52, 56 and 58 of the seventh embodiment of the present invention are the profiles, wherein the distance between the cancellation region 30 and the focal point formation region 28 is set equal to each pitch of the 3rd to 5th zones on the phase profile 60 (FIG. 31D) of the focal point formation region 28 having the 3rd to 5th zones in an equal-pitch relation and the 1st and 2nd zones in a Fresnel-pitch relation with the addition power of 2 Diopter as shown in Table 8 (FIGS. 31A, 31B, 31C). The region 54 between the cancellation region 30 and the focal point formation region 28 is made into a refraction region with a phase constant at h=0. For the convenience sake, this region was named 6th zone. This refraction region 54 separates the cancellation region 30 from the focal point formation region 28 by a certain distance. The cancellation region 30 was divided into sections a, b and c for each different phase constant or phase shift for convenience.

TABLE 8

[Seventh embodiment]

| Region | Zone No. | | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|---|
| Focal point formation region | 1 | | 0.738918 | 0 | −1.57079 | 1.57079 | 0.5 | 0 |
| | 2 | | 1.044988 | 0.738918 | −1.57079 | 1.57079 | 0.5 | 0 |
| | 3 | | 1.344988 | 1.044988 | −1.57079 | 1.57079 | 0.5 | 0 |
| | 4 | | 1.644988 | 1.344988 | −1.57079 | 1.57079 | 0.5 | 0 |
| | 5 | | 1.944988 | 1.644988 | −1.57079 | 1.57079 | 0.5 | 0 |
| Refraction region | 6 | | 2.244988 | 1.944988 | 0 | 0 | 0 | 0 |
| Cancellation region | 7 | a | 2.544988 | 2.244988 | −4.71238 | −1.57079 | 0.5 | −π |
| | | b | 2.544988 | 2.244988 | −3.86415 | −0.72256 | 0.5 | −0.73π |
| | | c | 2.544988 | 2.244988 | −5.65486 | −0.62831 | 0.8 | −π |

Figure 32A:
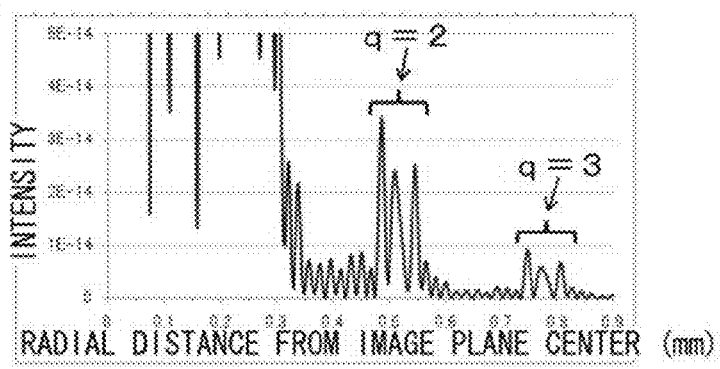
FIGS. 32A-32D are graphs for comparing simulation results of the image plane intensity distribution at the focal point position of 0th order diffracted light of the present embodiment with those of the comparative example.
Figure 32B:
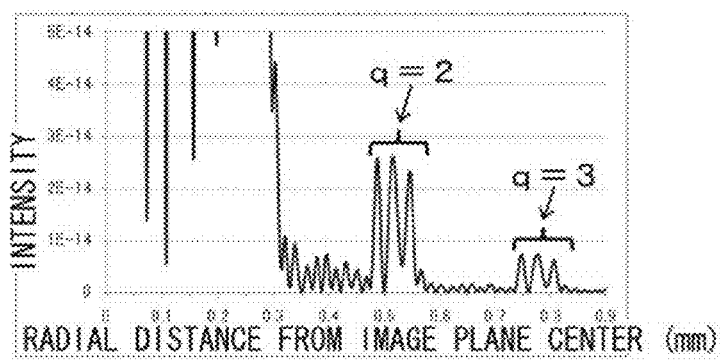

FIGS. 32A, 32B, 32C and 32D show image plane intensity distribution in case of including the focal point formation region 28 and the cancellation region 30. Assuming the phase shift of the cancellation region 30 to be τ=−π relative to the focal point formation region 28 (FIG. 32D), the maximum peak intensity of the side-band of each order is reduced but it does not bring the halo reduction effect because the satellite peaks existing around it are increased (FIG. 32A). However, if the phase shift is set at 1.27π or −0.73π, it is observed that the maximum peak intensity of the side-bands is reduced while restricting the increase of the satellite peaks as shown in FIG. 32B, thus achieving further halo reduction.

In the above example, the reason for the increase in intensity of the satellite peaks in the side-band when the phase shift is set at (2u−1)π (u is an integer) is the overcrowding of the amplitudes due to shorter periodic interval of the amplitude function as the cancellation region 30 moves further away from the focal point formation region 28 to the outside, resulting in overlapping of the amplitudes with the nearby waves to intensify each other rather than cancelling at the position of cancellation. Therefore, the phase shift is not always half the wavelength, but a higher cancellation effect can be obtained by adjusting the phase shift τ in consideration of the setting position and the like of the cancellation region 30.

Figure 32C:
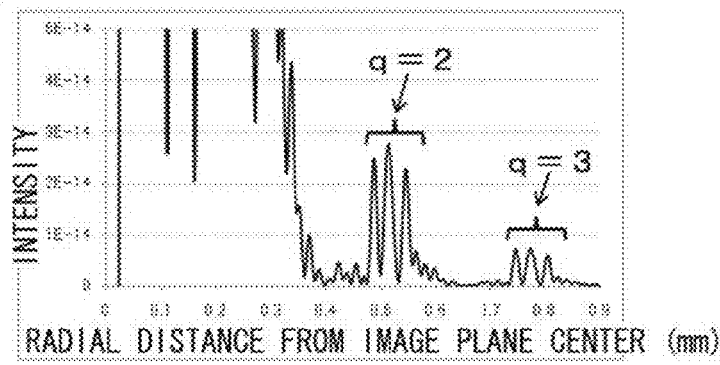
Figure 32D:
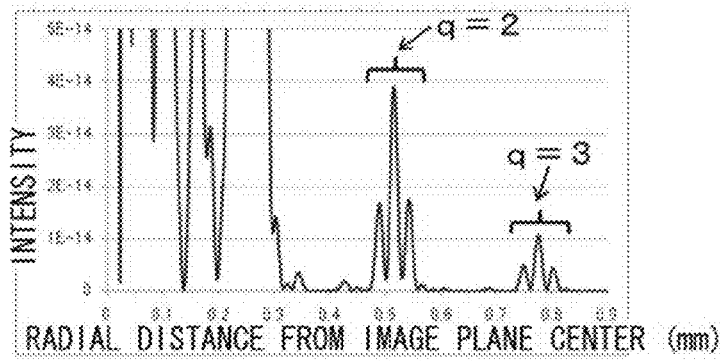

On the other hand, while the increase in the satellite peaks is restricted, the main peak intensity of the side-band can be reduced by means of modifying the phase constant of the blaze of the cancellation region 30 keeping the phase shift at −π. A specific example of such case is shown in FIG. 32C where the phase constant of the cancellation region 30 is set at h=0.8. If the phase constant of the cancellation region 30 is set at h=0.8, the peak intensity is reduced to the level equal to where the phase constant h is set at 0.5 and the phase shift at 1.27π or −0.73π.

Thus, it is possible to maximize the cancellation effect also by means of modifying the phase constant or phase shift of the blaze of the cancellation region 30. Such optimization of the cancellation effect through adjustment of the phase constant h and the phase shift τ can be equally applied to the case of cancellation for the Fresnel-pitch zone represented by the fifth embodiment or the case of cancellation for the equal-pitch zone represented by the sixth embodiment.

Another Aspect of Seventh Embodiment

Figure 33A:
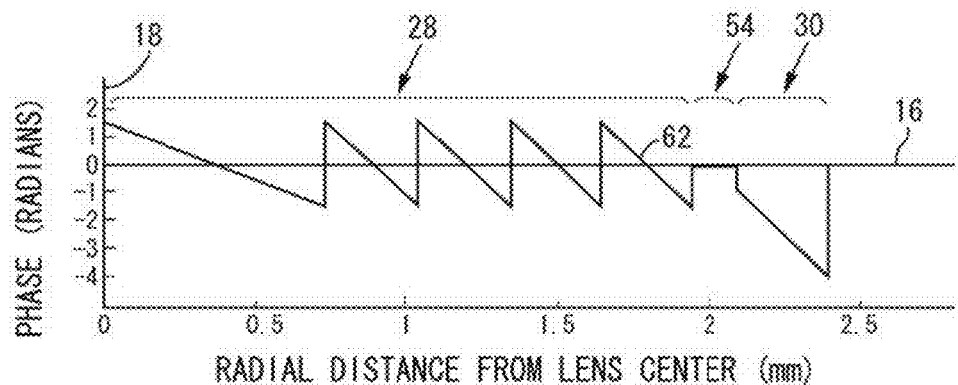
FIGS. 33A-33C are phase profiles of other aspects of the seventh embodiment of the present invention.
Figure 33B:
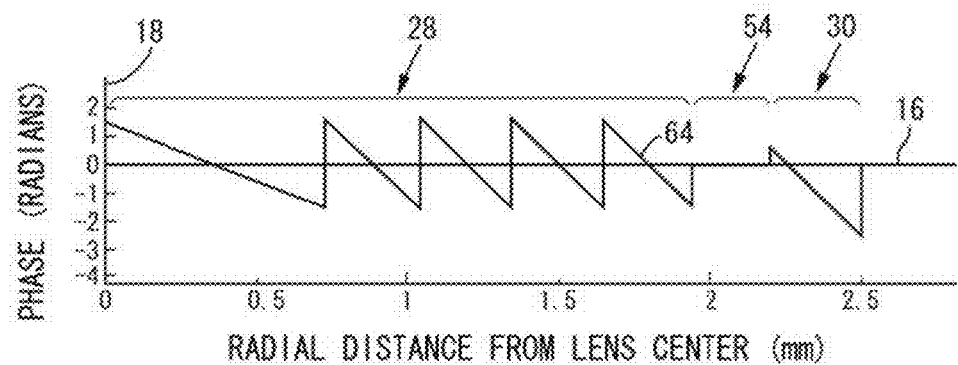
Figure 33C:
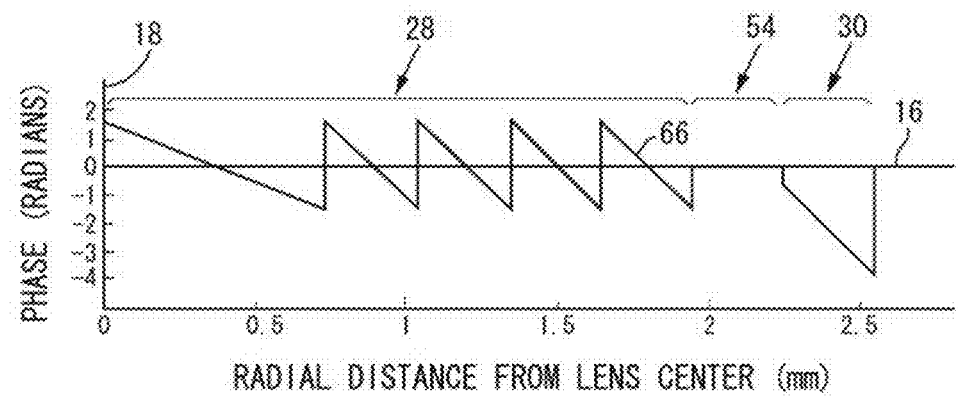

Meanwhile, the cancellation effect in case of setting the cancellation region 30 including the equal-pitch zone described above at a position away from the focal point formation region 28 may sometimes rely on the separation distance. The interval of the cancellation region 30 is equal to pitch of the equal-pitch zone of the focal point formation region 28, and cancellation effect in several cases where the separation distance is not equal will be described below. Cases where some of the separation distances (width of the refraction region 54) in the focal point formation region 28 of the seventh embodiment (Table 8) are changed will be examined. As shown in Table 9, the separation distances (the figures listed under No. 6) are set at 0.155 mm ('a' in Table 9), 0.255 mm ('b' in Table 9) and 0.3 mm ('c' in Table 9), and the phase shift of the cancellation region 30 that causes the most cancellation effect was examined in each interval (corresponding to 'a,' 'b' and 'c' in Table 9). FIGS. 33A, 33B and 33C show phase profiles 62, 64 and 66, respectively, corresponding to Table 9 and FIGS. 34A, 34B and 34C) show intensity distribution on the 0th order focal point image plane corresponding thereto.

Figure 34A:
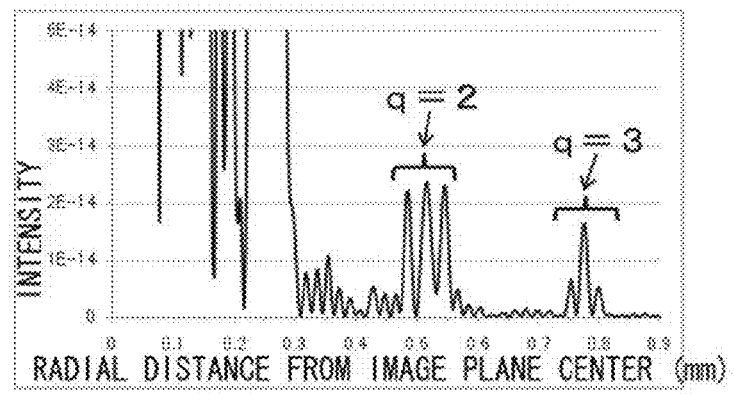
FIGS. 34A-34C are simulation results of the image plane intensity distribution at the focal point position of 0th order diffracted light of the present embodiment.
Figure 34B:
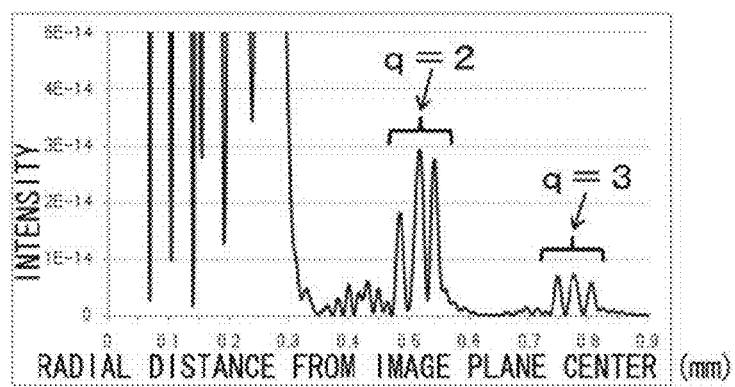
Figure 34C:
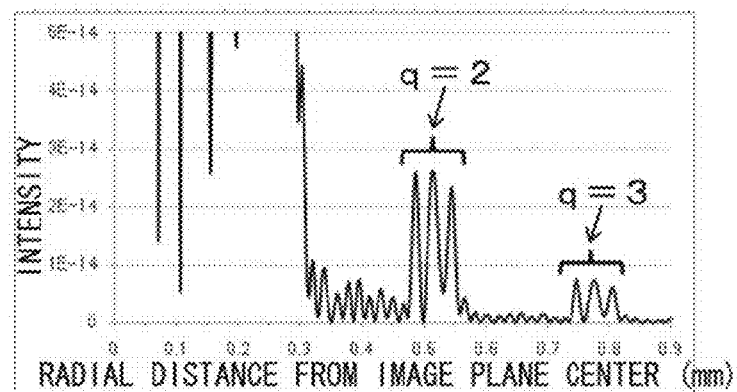

The line 'c' in Table 9 and FIG. 34C correspond to the case where the phase shift in the cancellation region 30 of the seventh embodiment is set at −0.73π and the separation distance is made equal to pitch of the equal-pitch zone. Meanwhile, in the case where the separation distance is about half at 0.155 mm, the peaks at q=2 are reduced as shown in FIG. 34A as is the case of FIG. 34C, but the peaks at q=3 are increased in contrast. When the separation distance is 0.255 mm, the peak reduction effect is not so great when q=2 but the peaks are reduced to the same level as those of the seventh embodiment when q=3, which indicates the halo expansion can be restricted in this case, too. These examples reveal that the cancellation effect is also dependent on the separation distance. Therefore, in case of setting the cancellation region 30 away from the focal point formation region 28, it is preferable to consider such characteristics to be able to obtain the desired cancellation effect.

A lens with the cancellation region 30 pre-integrated into the focal point formation region 28 within a range not to impair the focal point formation function thereof can be one of other aspects of the present invention. For example, if a phase shift is introduced to any of the zones in the focal point formation region 28 of the sixth embodiment, such zone would work as a kind of the cancellation region 30.

Eighth Embodiment

Figure 35:
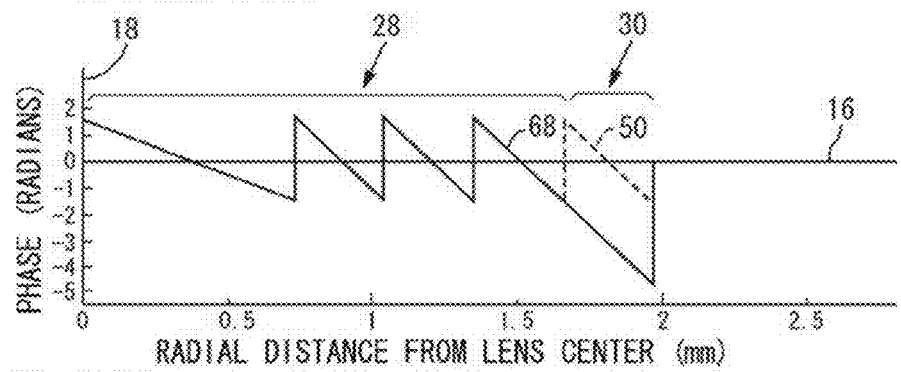
FIG. 35 is a phase profile of an eighth embodiment of the present invention.

Table 10 shows a phase profile of an eighth embodiment of the present invention. In such phase profile, a phase shift τ=−π is introduced to the phase function of the 5th zone in the focal point formation region 28 of the sixth embodiment (FIG. 27B). FIG. 35 shows a phase profile 68 with such

TABLE 9

[Another aspect of the seventh embodiment]

Figure 36:
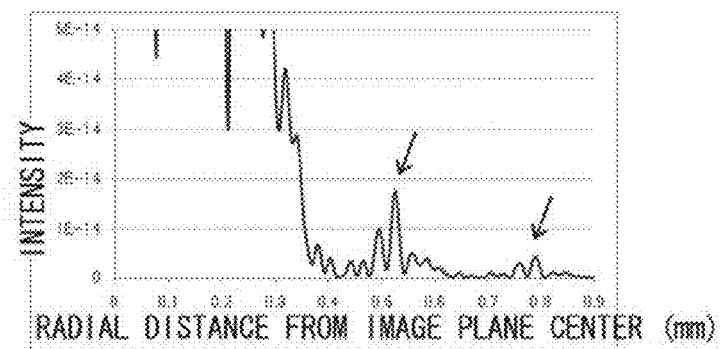
FIG. 36 shows simulation results of the image plane intensity distribution at the focal point position of 0th order diffracted light of the eighth embodiment.
Figure 37A:
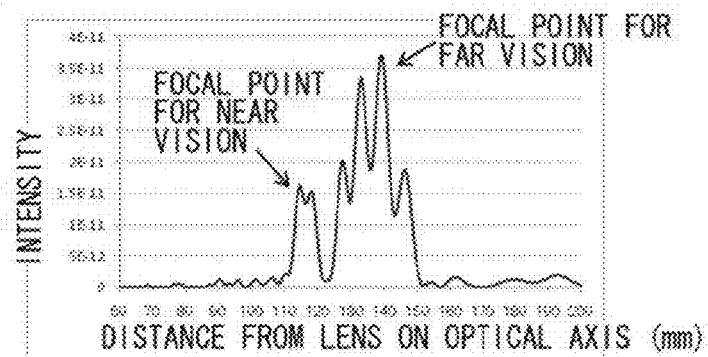
FIGS. 37A and 37B are graphs for comparing a result of simulation of intensity distribution on the optical axis of the present embodiment with that of the comparative example.
Figure 37B:
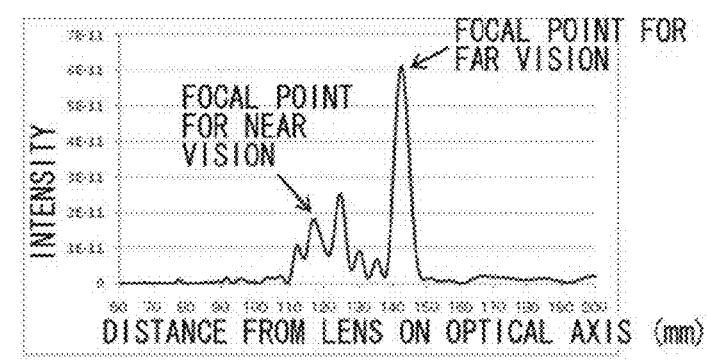

| Region | | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|---|
| Focal point | | 1 | 0.738918 | 0 | −1.57079 | 1.57079 | 0.5 | 0 |
| formation | | 2 | 1.044988 | 0.738918 | −1.57079 | 1.57079 | 0.5 | 0 |
| Region | | 3 | 1.344988 | 1.044988 | −1.57079 | 1.57079 | 0.5 | 0 |
| | | 4 | 1.644988 | 1.344988 | −1.57079 | 1.57079 | 0.5 | 0 |
| | | 5 | 1.944988 | 1.644988 | −1.57079 | 1.57079 | 0.5 | 0 |
| Refraction | a | 6 | 2.1 | 1.944988 | 0 | 0 | 0 | 0 |
| Region | b | 6 | 2.2 | 1.944988 | 0 | 0 | 0 | 0 |
| | c | 6 | 2.244988 | 1.944988 | 0 | 0 | 0 | 0 |
| Cancellation | a | 7 | 2.4 | 2.1 | −4.14690 | −1.00530 | 0.5 | −0.82π |
| Region | b | 7 | 2.5 | 2.2 | −2.51327 | 0.62831 | 0.5 | −0.3π |
| | c | 7 | 2.544988 | 2.244988 | −3.86415 | −0.72256 | 0.5 | −0.73π | phase shift introduced. Also, FIG. 36 shows an image plane intensity distribution of the present embodiment. Comparing it with the one with no phase shift introduced to the 5th zone (FIG. 28B), it is observed that the one with the phase shift introduced to the zones in the focal point formation region 28 has the intensity of the side-band peaks reduced significantly. Also, comparing the intensity distribution of the present embodiment on the optical axis (FIG. 37A) to that of the comparative example where no phase shift is introduced (FIG. 37B), despite the fact that part of the focal point formation region 28 is substituted for the cancellation region 30, the peaks appear substantially equally at far and near distances, which indicates that it can function as a multifocal ophthalmic lens.

TABLE 10

[Eighth embodiment]

| Region | Zone No. | $r_n$ (mm) | $r_{n-1}$ (mm) | $\phi_n$ (radian) | $\phi_{n-1}$ (radian) | Phase constant h | Phase shift $\tau$ (radian) |
|---|---|---|---|---|---|---|---|
| Focal point formation region | 1 | 0.738918 | 0 | −1.57079 | 1.57079 | 0.5 | 0 |
| | 2 | 1.044988 | 0.738918 | −1.57079 | 1.57079 | 0.5 | 0 |
| | 3 | 1.351057 | 1.044988 | −1.57079 | 1.57079 | 0.5 | 0 |
| | 4 | 1.657127 | 1.351057 | −1.57079 | 1.57079 | 0.5 | 0 |
| Cancellation region | 5 | 1.963197 | 1.657127 | −4.71238 | −1.57079 | 0.5 | −π |

Figure 38A:
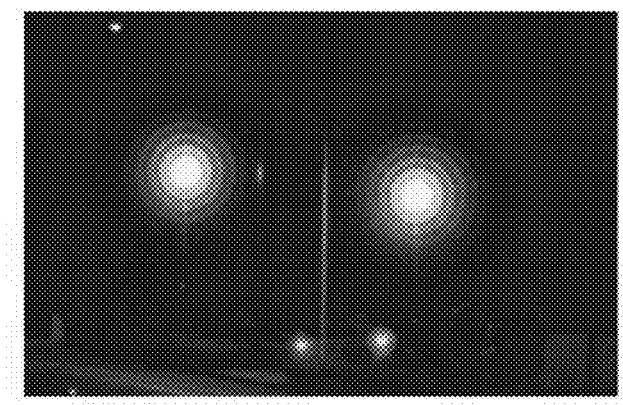
FIGS. 38A and 38B are actual photos of halos of the present embodiment and of the comparative example.
Figure 38B:
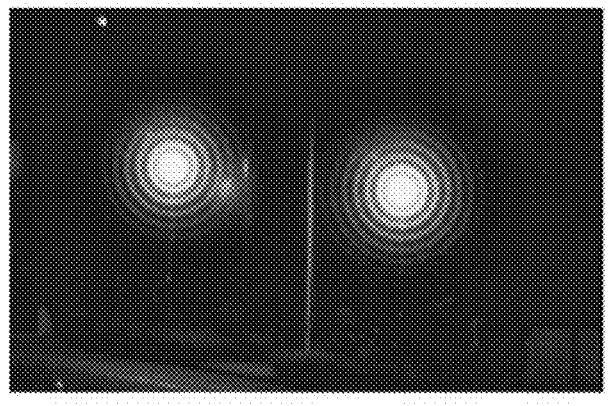

Contact lenses according to the present embodiment were manufactured in the same way as in the sixth embodiment, and photos were taken of their halos at night. As a comparison, a test result of contact lenses composed only of the focal point formation region 28 of the sixth embodiment is quoted. FIG. 38B is the same photo as shown in FIG. 29B, which features halos at night in case of having no cancellation region 30. FIG. 38A shows an actual photo of halos at night as provided by the present embodiment. As evident from FIG. 38A, the halo is substantially reduced. By means of integrating a region having the cancellation effect in part of the focal point formation region 28 represented by the examples above, it is possible to reduce the halo more effectively.

The phase function of the cancellation region 30 shown in the third embodiment (Equation 23, FIG. 39A) can be deemed as a composite of two phase functions (Equations 24, 25) that can be divided into two different regions A $(r_{l-1}-r_l)$, B$(r_{m-1}-r_m)$. Thus, since the phase function for cancellation can be expressed as a composite of multiple phase functions, an embodiment with multiple cancellation region 30 having different phase functions can be favorably used in the present invention. In that case, the divided cancellation region 30 can be set in separation or in succession.

Phase function of the third embodiment [Equation 23]
$$\phi_c(r) = -0.35\pi \times \sin\left\{2\pi\left(\frac{r-r_{n-1}}{r_n-r_{n-1}}\right)^2\right\}$$

Phase function of Region A: [Equation 24]
$$\phi_s(r) = -0.35\pi \times \sin\left\{\pi\left(\frac{r-r_{i-1}}{r_i-r_{i-1}}\right)^2\right\}$$

Phase function of Region B: [Equation 25]
$$\phi_c(r) = 0.35\pi \times \sin\left\{\pi\left(\frac{r-r_{n-1}}{r_m-r_{m-1}}\right)\right\}$$

The previous embodiments showed cases where the cancellation region 30 exists independently from the focal point formation region 28. As another aspect, there could be a system where a region is partially included that enhances the phase cancellation effect through a synergy with the cancellation region 30. However, it is desirable to set such a region as a supplement to work to the extent not to impair the far and near vision in a photopic to mesopic environment, which should originally be achieved by the focal point formation region 28. An example of such phase cancellation through a synergy is shown below. The present aspect can be interpreted as the one having part of the cancellation region 30 included in the focal point formation region 28.

Ninth Embodiment

Figure 40:
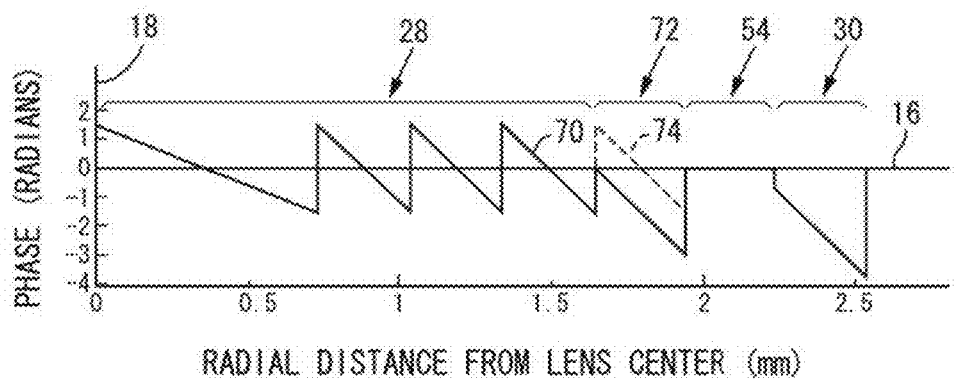
FIG. 40 is a phase profile of a ninth embodiment of the present invention.
Figure 41A:
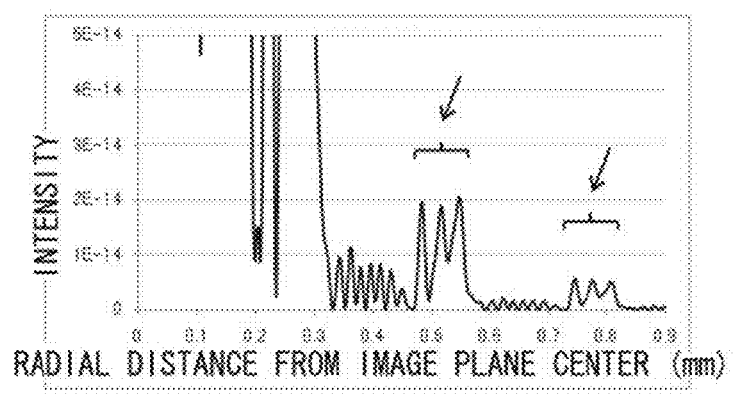
FIGS. 41A and 41B are graphs for comparing simulation results of the image plane intensity distribution at the focal point position of 0th order diffracted light of the present embodiment with those of the comparative example.
Figure 41B:
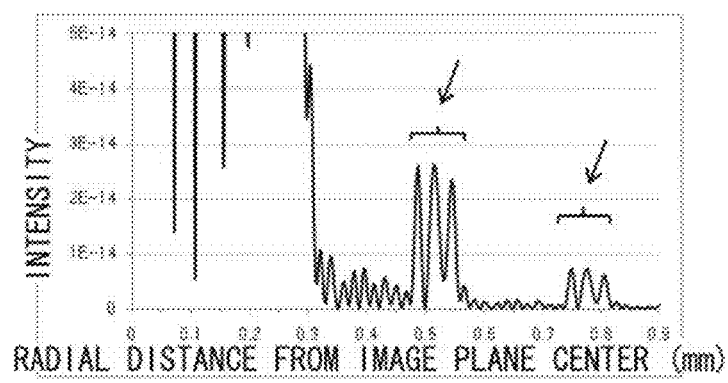
Figure 42A:
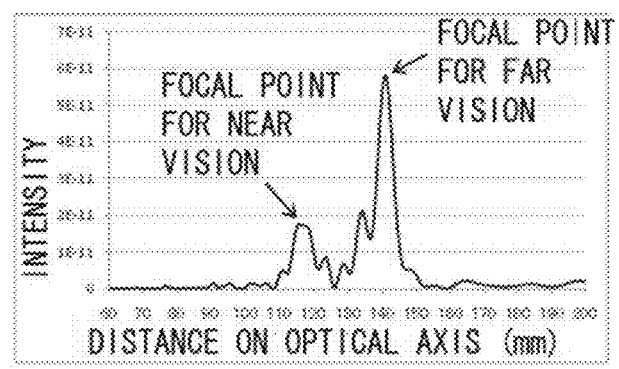
FIGS. 42A and 42B are graphs for comparing a result of simulation of intensity distribution on the optical axis of the present embodiment with that of the comparative example.
Figure 42B:
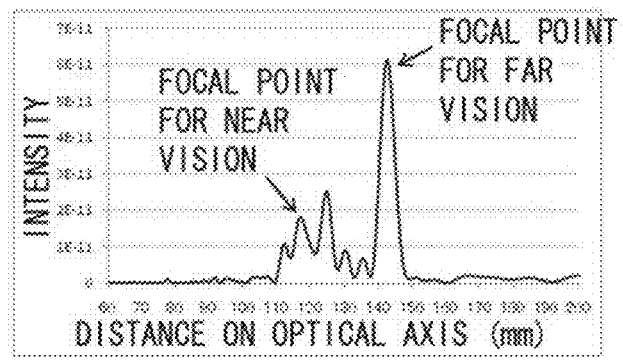
Figure 43A:
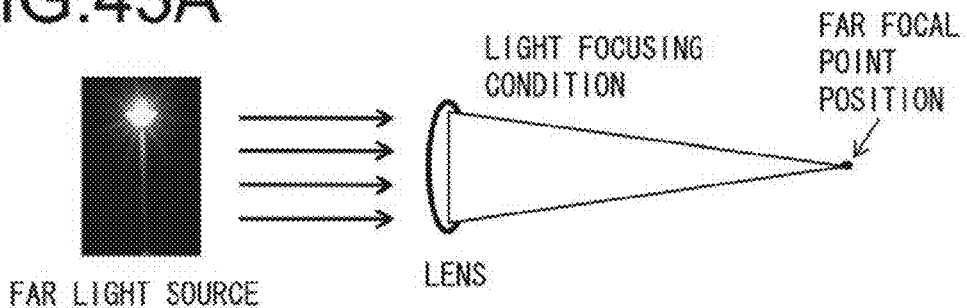
FIGS. 43A-43D are diagrams and graphs suitable for explaining imaging characteristics of a monofocal lens.
Figure 43B:
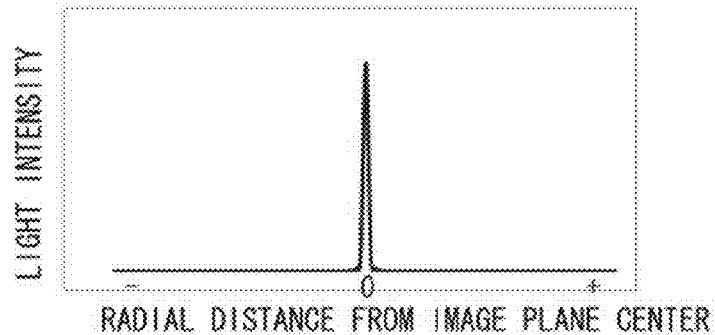
Figure 43C:
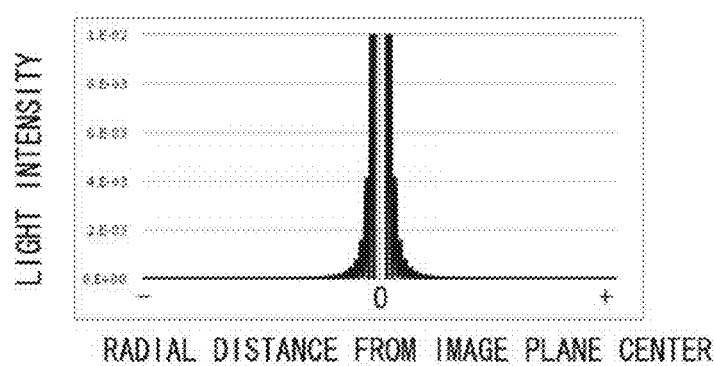
Figure 43D:
Figure 44A:
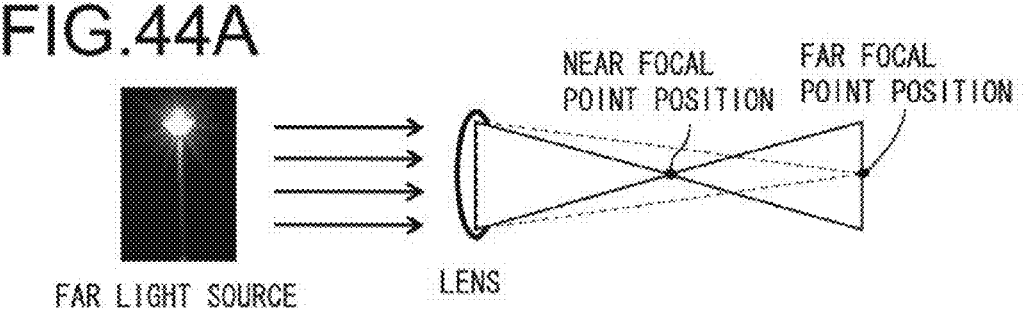
FIGS. 44A-44D are diagrams and graphs suitable for explaining generation of halos in a diffraction-type lens.
Figure 44B:
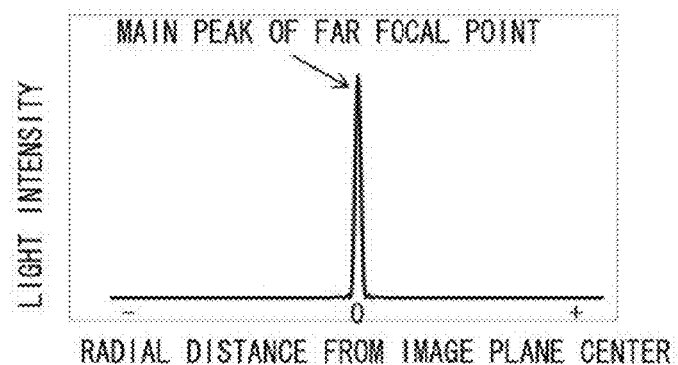
Figure 44C:
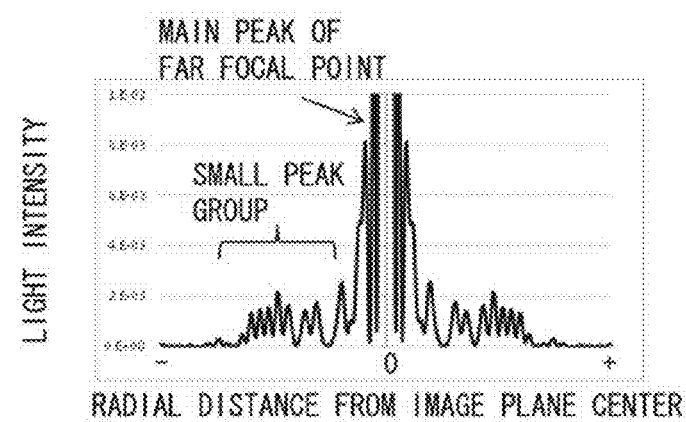
Figure 44D:
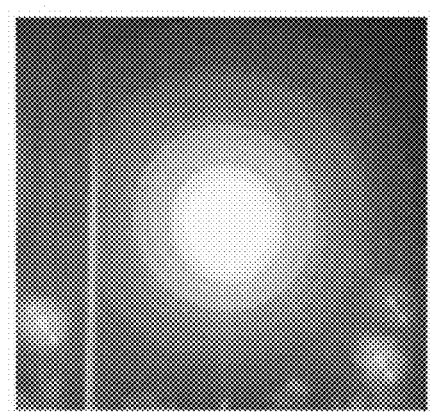
Figure 45A:
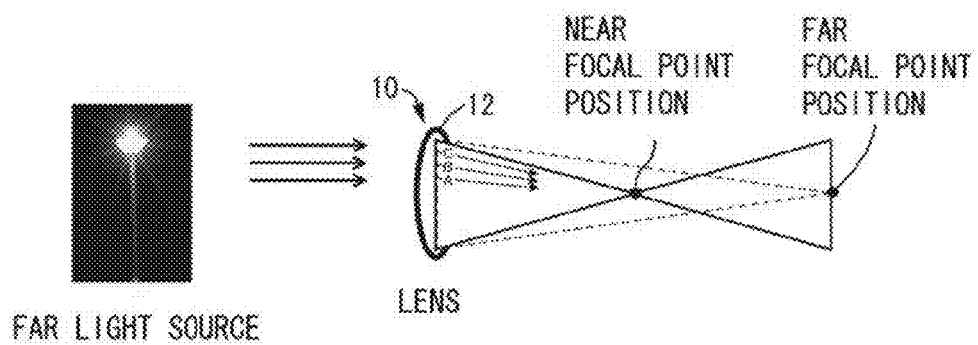
FIGS. 45A-45D are illustrative diagram and graphs showing halo-forming models of a diffraction-type lens.
Figure 45B:
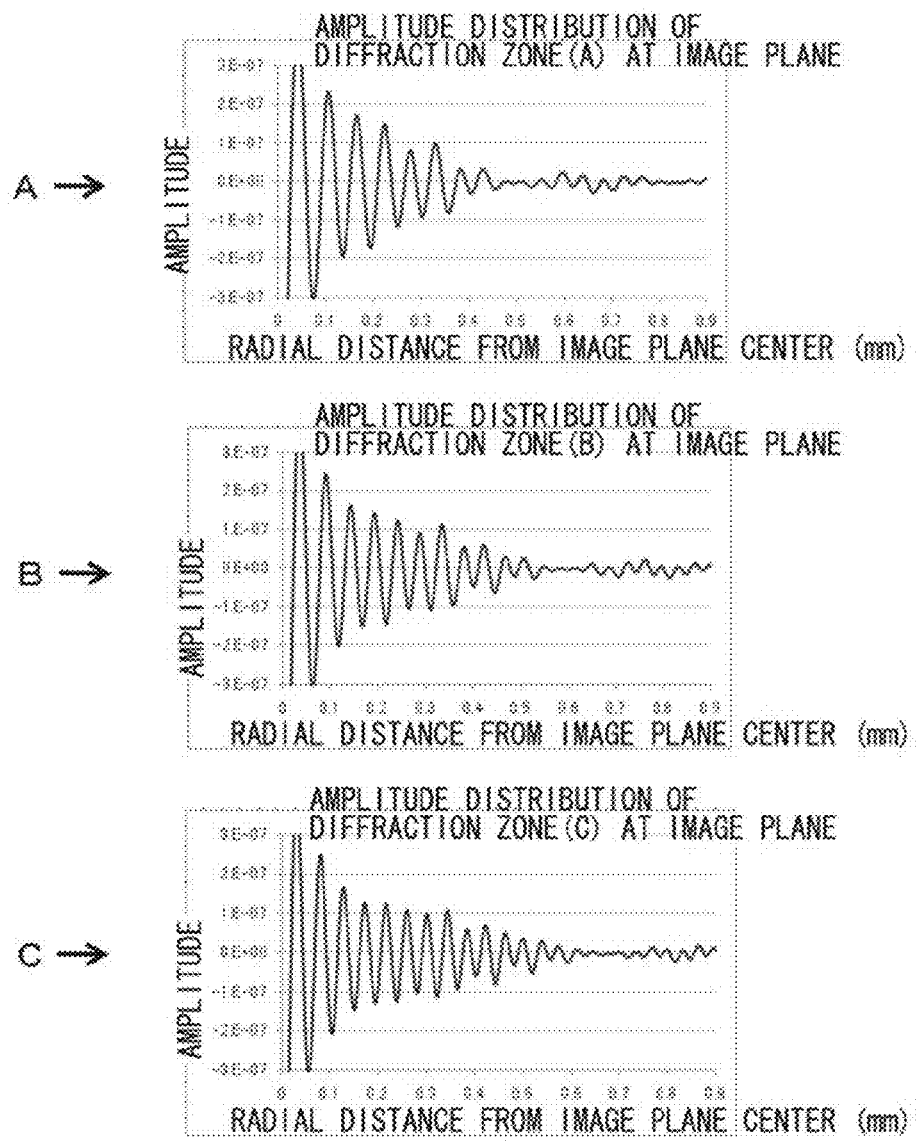
Figure 45C:
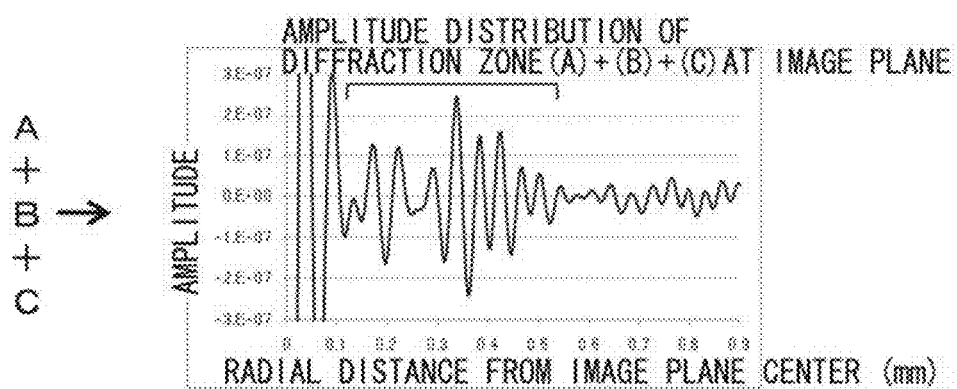
Figure 45D:
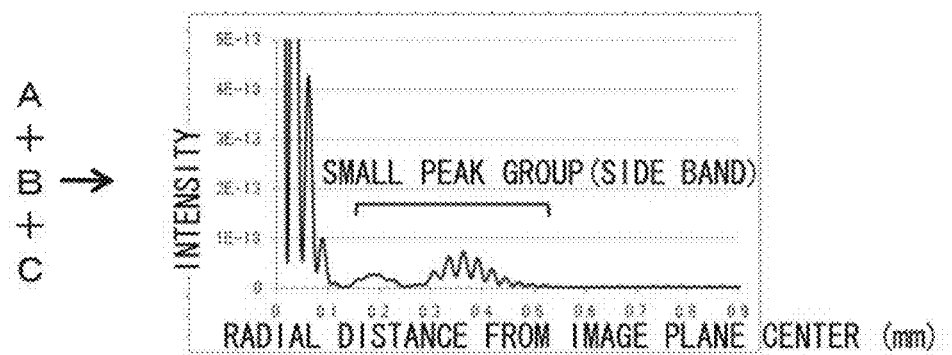

FIG. 40 shows a phase profile used in the seventh embodiment that makes the 6th zone the refraction region 54 with the phase constant at h=0, the phase constant being set at h=0.5 and the phase shift at τ=−0.73π for the cancellation region 30 in the 7th zone (FIG. 31B), wherein the 5th zone is made to be a supplementary cancellation region 72 with the blaze shifted by the phase shift at τ=−0.5π, that is, a phase profile 70 (Table 11) of a ninth embodiment of the present invention. The dotted line portion of FIG. 40 indicates a blaze position when it is not used for supplementary cancellation. FIG. 41A shows intensity distribution on the 0th order focal point image plane of such phase profile 70. In this case, it is observed that the peak intensity is further reduced from the level of the image plane intensity distribution of the seventh embodiment (FIG. 41B) where the 5th zone is not turned into the supplementary cancellation region 72. Next, in order to examine the impact on the focal point formation region 28 with respect to the far and near vision, intensity distribution on the optical axis with and without setting the supplementary cancellation region 72 was calculated. FIGS. 42A and 42B show intensity distribution on the optical axis by the focal point formation region 28 including the supplementary cancellation region 72 in case of setting up the supplementary cancellation region 72 and not setting it up (a phase profile 74 in a dotted line in FIG. 40), respectively. Comparison of the intensity distribution of both cases reveals that setting the supplementary cancellation region 72 makes no significant difference in the intensity ratio of far and near vision. Therefore, it is observed that the supplementary cancellation region 72 of the present embodiment plays a supplementary role in potentially further reducing the halo formation in cooperation with the cancellation region 30 without impairing the focal point formation function of the focal point formation region 28.

TABLE 11

[Ninth embodiment]

| Region | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|
| Focal point formation region | 1 | 0.738918 | 0 | −1.57079 | 1.57079 | 0.5 | 0 |
| | 2 | 1.044988 | 0.738918 | −1.57079 | 1.57079 | 0.5 | 0 |
| | 3 | 1.344988 | 1.044988 | −1.57079 | 1.57079 | 0.5 | 0 |
| | 4 | 1.644988 | 1.344988 | −1.57079 | 1.57079 | 0.5 | 0 |
| | 5 | 1.944988 | 1.644988 | −3.14159 | 0 | 0.5 | −0.5π |
| Refraction region | 6 | 2.244988 | 1.944988 | 0 | 0 | 0 | 0 |
| Cancellation region | 7 | 2.544988 | 2.244988 | −3.86415 | −0.72256 | 0.5 | −0.73π |

As can be understood from the description based on the aforementioned embodiments, it is desirable to arrange a part or whole of the cancellation region 30 on the outside of the focal point formation region 28, but some zones included in the focal point formation region 28 can be used in some embodiments. In the present invention, the inner diameter of the cancellation region 30 is preferably in a range of 2 to 6 mm and the outer diameter thereof in a range of 3 to 8 mm. Also, the phase shift τ is preferably in a range defined by Equation 11 above.

Also, as another aspect of the cancellation region, an embodiment wherein the blaze inclination is reversed from that of the focal point formation region can work effectively in the present invention. An embodiment based on such method will be described below.

Tenth Embodiment

Figure 49A:
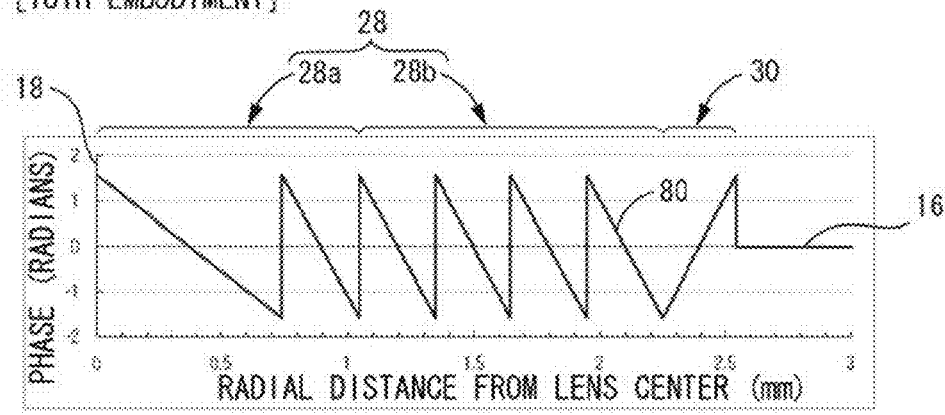
FIG. 49A is a phase profile of a tenth embodiment of the present invention and FIG. 49B is a phase profile of a comparative example.
Figure 49B:
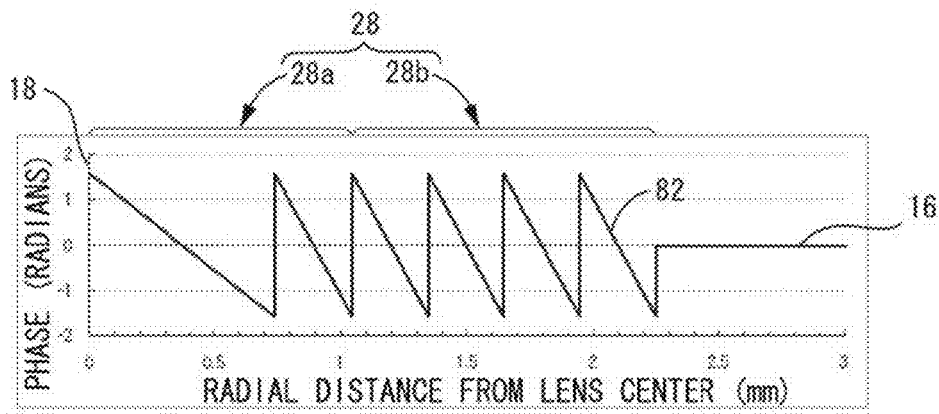
Figure 50A:
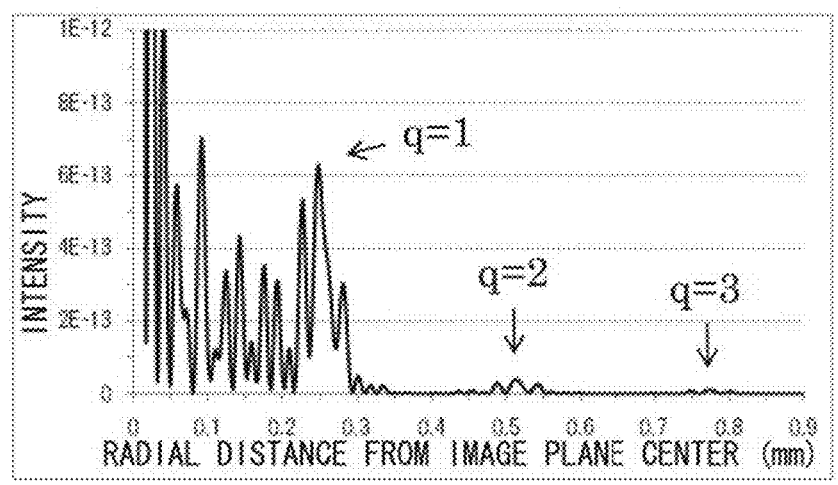
FIG. 50A shows simulation results of the image plane intensity distribution at the focal point position of 0th order diffracted light of the present embodiment and FIG. 50B is an enlarged view of a principle part of FIG. 50A.
Figure 50B:
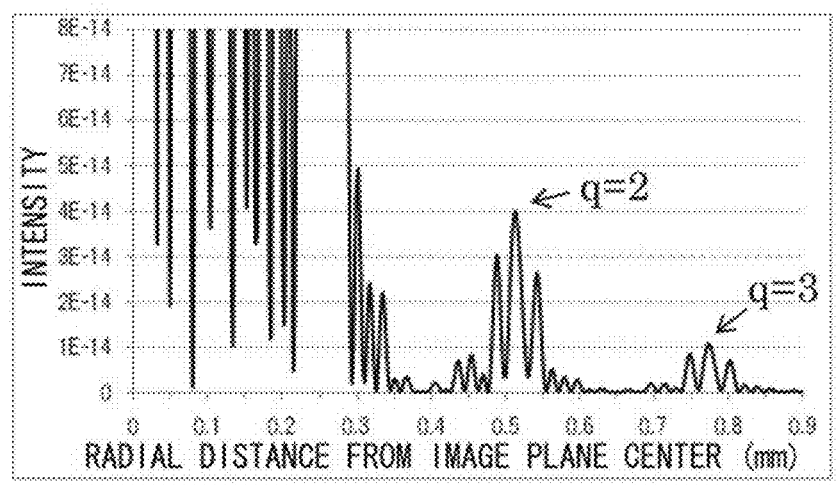
Figure 51A:
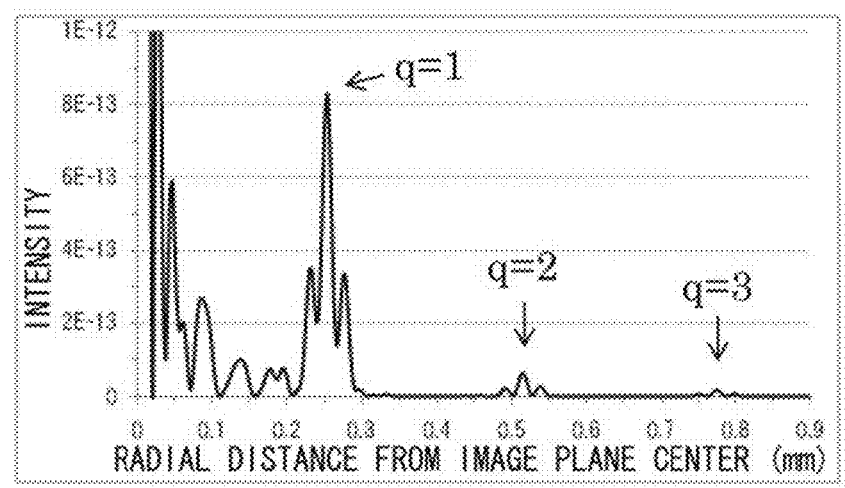
FIG. 51A is a simulation result of the image plane intensity distribution at the focal point position of 0th order diffracted light of the comparative example shown in FIG. 49B
Figure 51B:
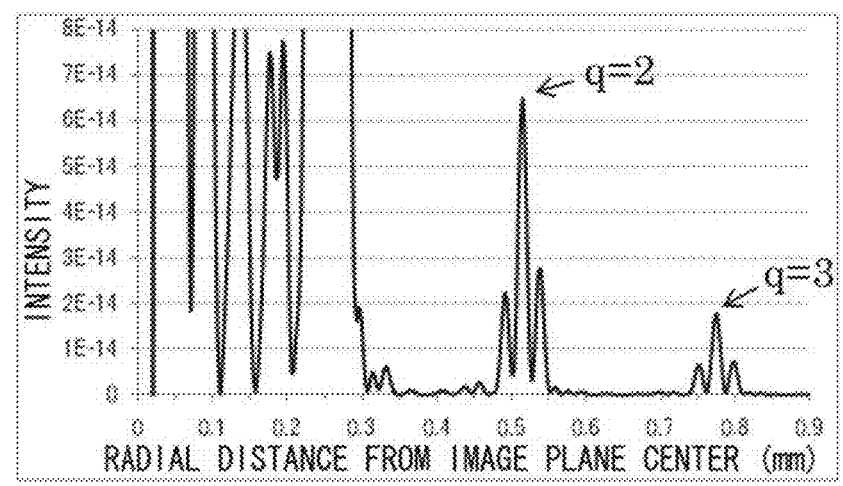
FIG. 51B is an enlarged view of a principle part of FIG. 51A.

FIG. 49A and Table 12 show a phase profile 80 of a tenth embodiment. The present embodiment has the focal point formation region 28 comprising a region 28a composed of 1st and 2nd zones in a Fresnel-pitch relation with the addition power of 2 Diopter and a region 28b composed of 3rd to 6th zones in an equal-pitch relation with the zone pitch of 0.3 mm. All the phase constants in the focal point formation region 28 are set at h=0.5. In the present embodiment, the 7th zone is set as the cancellation region 30 with the same interval as those of the equal-pitch region at 0.3 mm and the phase constant of the blaze set at h=−0.5. A phase profile 82 is shown in FIG. 49B as a comparative example of the focal point formation region 28. As evident from FIG. 49A, the blaze inclination of such cancellation region 30 is reversed from that of the focal point formation region 28. FIGS. 50A and 50B show intensity distribution on the 0th order focal point image plane of the present embodiment. FIGS. 51A and 51B show intensity distribution of a comparative example. FIGS. 50B and 51B have the vertical scale enlarged from FIGS. 50A and 51A, respectively. As described in the previous embodiments, the comparative example shows a side-band pattern (q=1, 2, 3 . . . in the figures) wherein multiple peaks deriving from the equal-pitch region are distributed with their intensity decreasing. Meanwhile, the present embodiment reveals that the intensity is reduced in any side-band. As can be seen in these examples, the phase profile with the blaze inclination reversed from that of the focal point formation region 28 can also be used as the cancellation region 30.

TABLE 12

[Tenth embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.738918 | 0 | −1.57079 | 1.57079 | 0.5 |
| | 2 | 1.044988 | 0.738918 | −1.57079 | 1.57079 | 0.5 |
| | 3 | 1.344988 | 1.044988 | −1.57079 | 1.57079 | 0.5 |
| | 4 | 1.644988 | 1.344988 | −1.57079 | 1.57079 | 0.5 |
| | 5 | 1.944988 | 1.644988 | −1.57079 | 1.57079 | 0.5 |
| | 6 | 2.244988 | 1.944988 | −1.57079 | 1.57079 | 0.5 |
| Cancellation region | 7 | 2.544988 | 2.244988 | 1.57079 | −1.57079 | −0.5 |

Results of examination on the reasons for the reduction of side-band intensity by means of reversing the direction of the blaze inclination of the focal point formation region 28 are described below in reference to the present embodiment.

Figure 52:
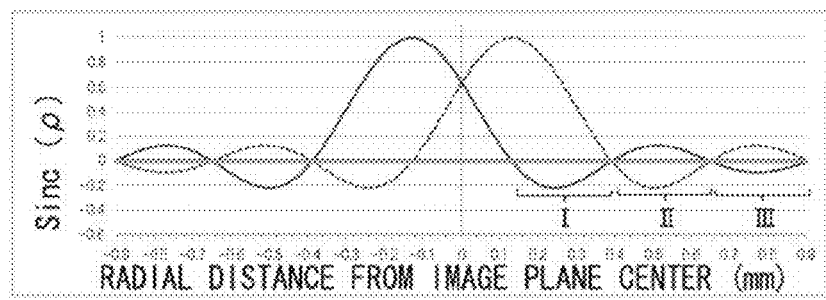
FIG. 52 is a graph showing a Sinc function that constitutes the amplitude function of the present embodiment, wherein the solid line represents the one regarding the cancellation region and the dotted line the focal point formation region.
Figure 53:
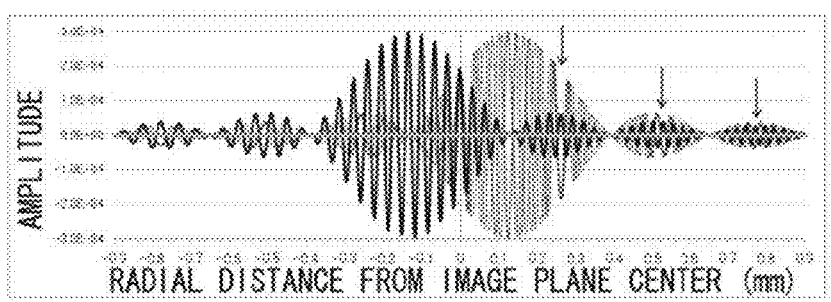
FIG. 53 is a graph showing an amplitude function of the present embodiment, wherein the solid line represents the one regarding the cancellation region and the dotted line the focal point formation region.

FIG. 52 shows a Sinc function term extracted from the amplitude function of Equation 20 above with regard to each zone in the focal point formation region and the cancellation region of the present (tenth) embodiment. The dotted line indicates the Sinc function in the focal point formation region 28 and the solid line indicates the Sinc function in the zones of the cancellation region 30. For the focal point formation region 28, only the zones in an equal-pitch relation (28b) are shown. The Sinc function in the equal-pitch region has characteristics such that all Sinc functions take an identical shape to overlap with each other when the phase constant is set equal. Meanwhile, when the phase constant is modified, the Sinc function will shift in the horizontal-axis direction. It can be seen that, as the phase constant decreases, the Sinc function shifts in the negative direction along the horizontal axis to align with the next matching node when the constant is set at h=−0.5. The extrema in the regions I, II and III of the Sinc function shifted as described above will be in an inverted relation to those of the Sinc function of the equal-pitch region 28b as part of the focal point formation region 28. Meanwhile, since the cosine function term in the amplitude function of Equation 20 does not cause any phase change even if the phase constant is changed, the phase at the position where the waves intensify each other is determined by the correlation among the extrema of the Sinc function of the respective zones. As a result, the overall amplitude function will look like FIG. 53 and the amplitude function of the cancellation region 30 turns out to be the one with the phase inverted at the positions (marked by arrows) where the amplitude functions of the focal point formation region intensify each other. Since the extrema are thus inverted between the positive and negative signs by the shift of the Sinc function, the phase is inverted as a result to exert the cancellation effect.

Another Aspect of the Tenth Embodiment

Figure 54:
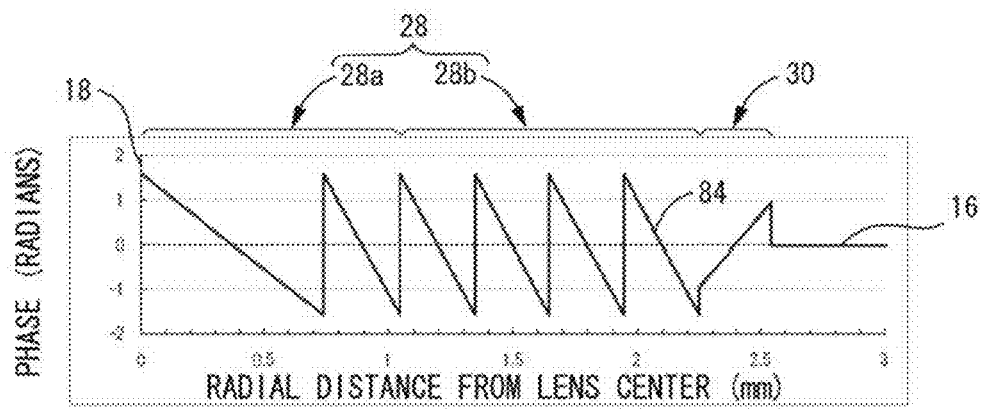
FIG. 54 is a phase profile of another aspect of the present embodiment.
Figure 55A:
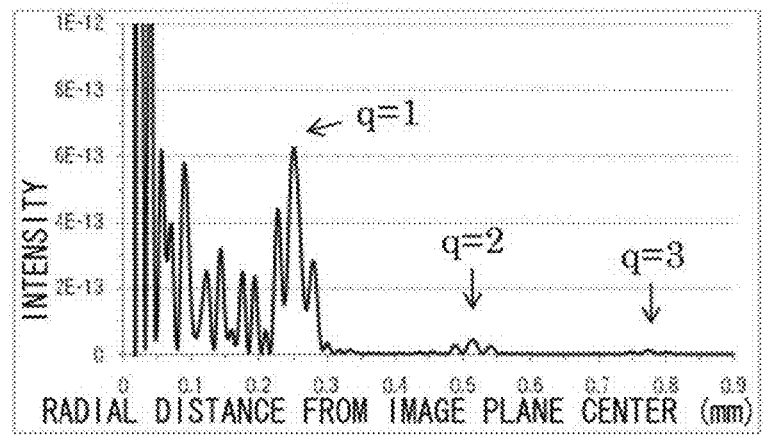
FIG. 55A shows simulation results of the image plane intensity distribution at the focal point position of 0th order diffracted light of the present aspect and FIG. 55B is an enlarged view of a principle part of FIG. 55A.
Figure 55B:
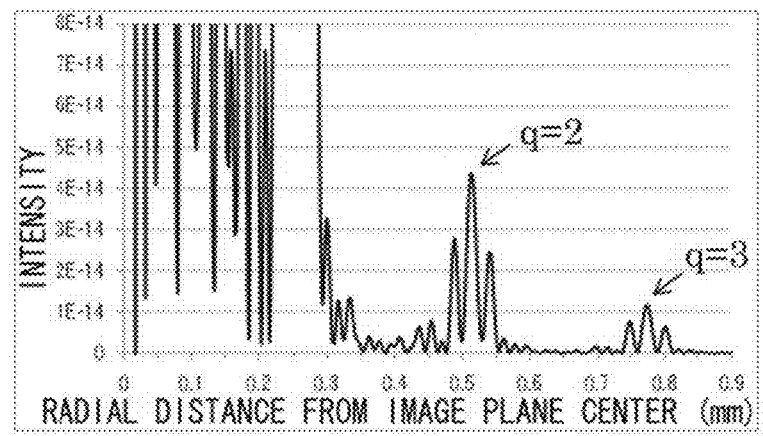

Next, as another aspect of the tenth embodiment, wherein the cancellation region 30 is modified as described above, a phase profile 84 when the phase constant in the cancellation region of the tenth embodiment is set at h=−0.3 and its intensity distribution on the 0th order focal point image plane are shown in Table 13 below and FIGS. 54, 55A, 55B, respectively.

TABLE 13

[Another aspect of the tenth embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.738918 | 0 | −1.57079 | 1.57079 | 0.5 |
| | 2 | 1.044988 | 0.738918 | −1.57079 | 1.57079 | 0.5 |
| | 3 | 1.344988 | 1.044988 | −1.57079 | 1.57079 | 0.5 |
| | 4 | 1.644988 | 1.344988 | −1.57079 | 1.57079 | 0.5 |
| | 5 | 1.944988 | 1.644988 | −1.57079 | 1.57079 | 0.5 |
| | 6 | 2.244988 | 1.944988 | −1.57079 | 1.57079 | 0.5 |
| Cancellation region | 7 | 2.544988 | 2.244988 | 0.94247 | −0.94247 | −0.3 |

Even in this example of another aspect, the side-band intensity (at q=1, 2, 3 . . . ) is distinctively reduced as opposed to the comparative example (FIGS. 51A, 51B), which indicates that the same level of cancellation effect is exerted as the tenth embodiment. Results of examination on the fact that the cancellation effect is achieved even if the phase constant is changed from h=−0.5 are described below.

Figure 56:
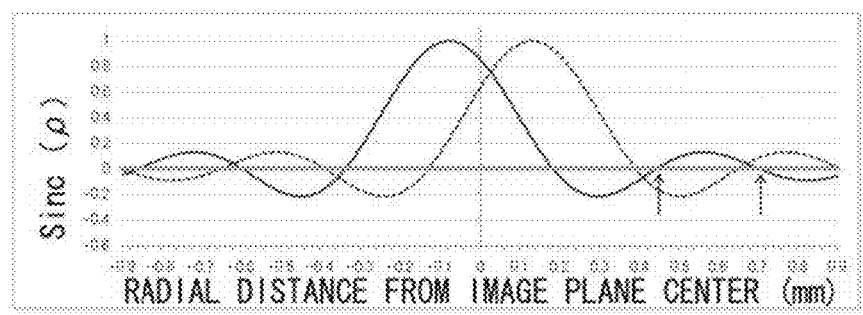
FIG. 56 is a graph showing a Sinc function that constitutes the amplitude function of the present aspect, wherein the solid line represents the one regarding the cancellation region and the dotted line the focal point formation region.
Figure 57:
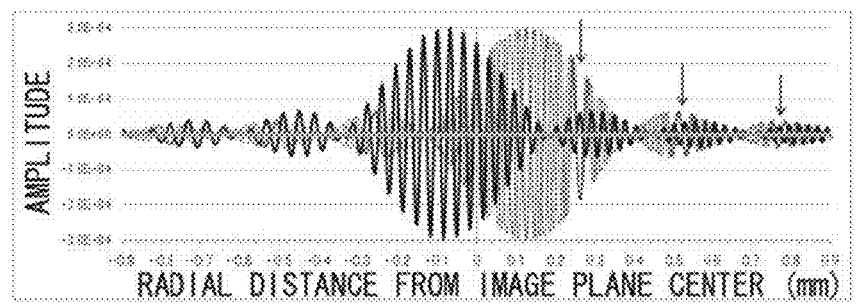
FIG. 57 is a graph showing an amplitude function of the present aspect, wherein the solid line represents the one regarding the cancellation region and the dotted line the focal point formation region.

That is, FIG. 56 shows the same Sinc function as shown in FIG. 52. If the phase constant is at h=−0.3, displacement of the Sinc function in the direction of the image plane's horizontal axis gets slightly smaller than when h=−0.5 failing to get aligned at some nodes and antinodes (shown by arrows in FIG. 56), but since the opposite relation of the Sinc function's extrema is maintained at the side-band positions in each region, amplitudes of opposite phases can be produced (FIG. 57).

Eleventh Embodiment

Figure 58A:
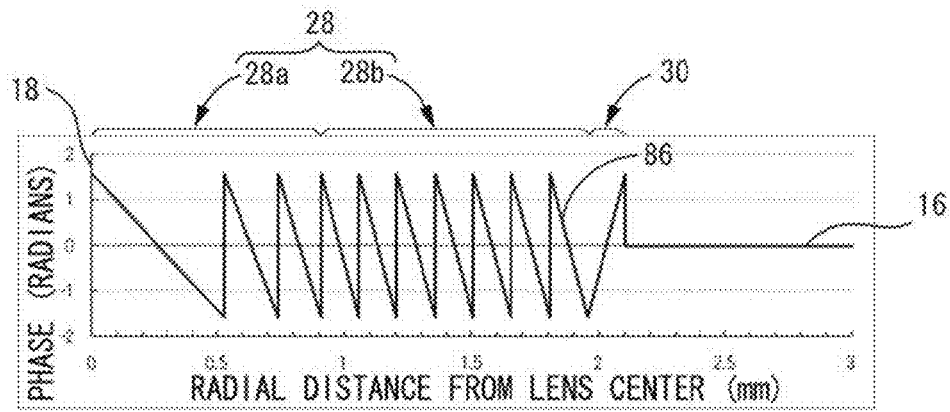
FIG. 58A is a phase profile of an eleventh embodiment of the present invention and FIG. 58B is a phase profile of a comparative example.
Figure 58B:
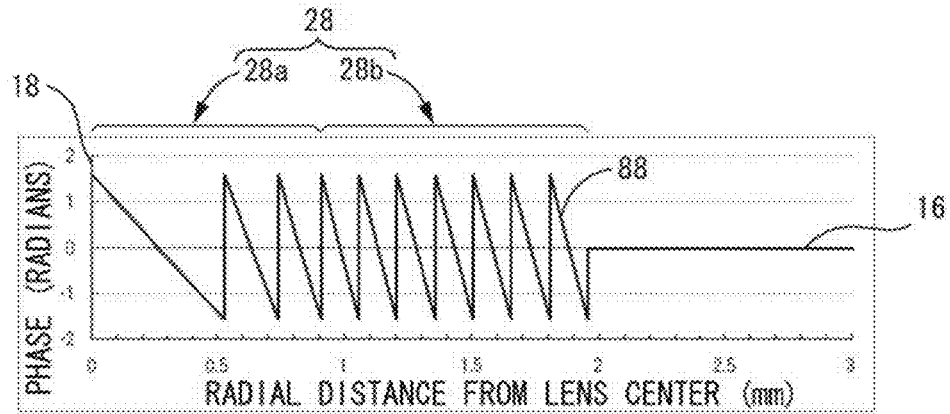
Figure 59A:
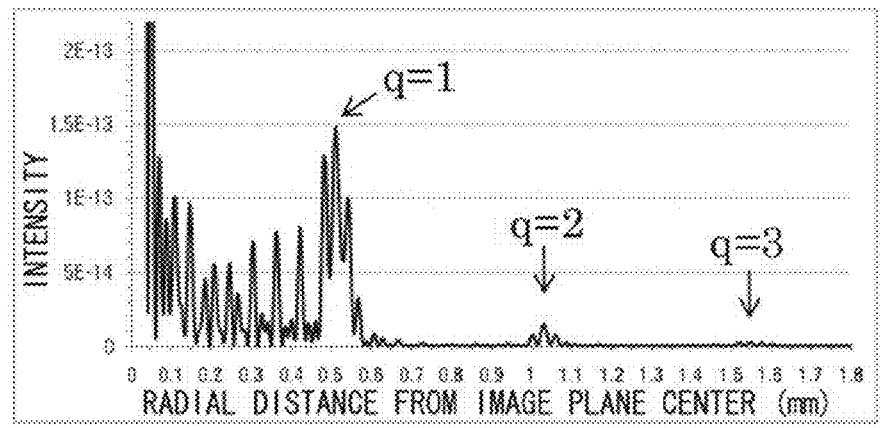
FIG. 59A shows simulation results of the image plane intensity distribution at the focal point position of 0th order diffracted light of the present embodiment and FIG. 59B is an enlarged view of a principle part of FIG. 59A.
Figure 59B:
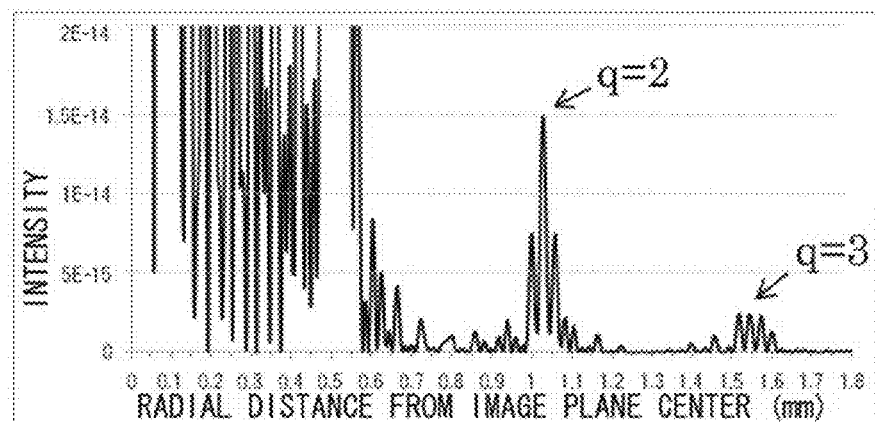

Table 14 and FIG. 58A show a phase profile 86 of an eleventh embodiment. The focal point formation region 28 of such embodiment comprises a region 28a composed of 1st to 3rd zones in a Fresnel-pitch relation with the addition power of 4 Diopter and the equal-pitch region 28b composed of 4th to 10th zones with the zone pitch at 0.15 mm. A phase profile 88 is shown in FIG. 58B as a comparative example of such focal point formation region 28. As evident from FIG. 58A, the cancellation region 30 was prepared by providing a zone adjacent to the focal point formation region 28 with the same interval as pitch of the equal-pitch region 28b and setting the phase constant at h=−0.5. FIGS. 59A and 59B show intensity distribution on the 0th order focal point image plane of the present embodiment.

TABLE 14

[Eleventh embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.522494 | 0 | −1.57079 | 1.57079 | 0.5 |
| | 2 | 0.738918 | 0.522494 | −1.57079 | 1.57079 | 0.5 |
| | 3 | 0.904986 | 0.738918 | −1.57079 | 1.57079 | 0.5 |
| | 4 | 1.054986 | 0.904986 | −1.57079 | 1.57079 | 0.5 |
| | 5 | 1.204986 | 1.054986 | −1.57079 | 1.57079 | 0.5 |
| | 6 | 1.354986 | 1.204986 | −1.57079 | 1.57079 | 0.5 |
| | 7 | 1.504986 | 1.354986 | −1.57079 | 1.57079 | 0.5 |
| | 8 | 1.654986 | 1.504986 | −1.57079 | 1.57079 | 0.5 |
| | 9 | 1.804986 | 1.654986 | −1.57079 | 1.57079 | 0.5 |
| | 10 | 1.954986 | 1.804986 | −1.57079 | 1.57079 | 0.5 |
| Cancellation region | 11 | 2.104986 | 1.954986 | 1.57079 | −1.57079 | −0.5 |

Figure 60:
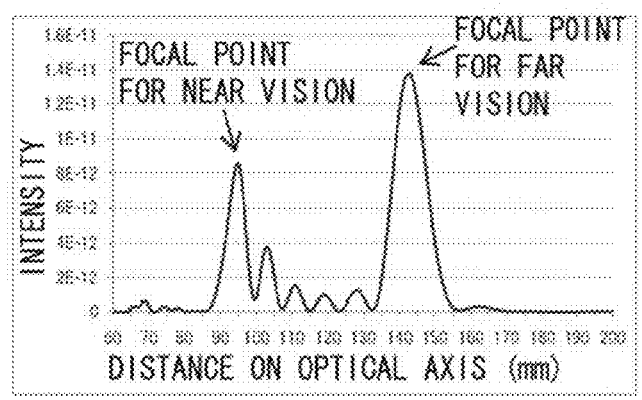
FIG. 60 shows a result of simulation of intensity distribution on the optical axis of the comparative example shown in FIG. 58B.
Figure 61A:
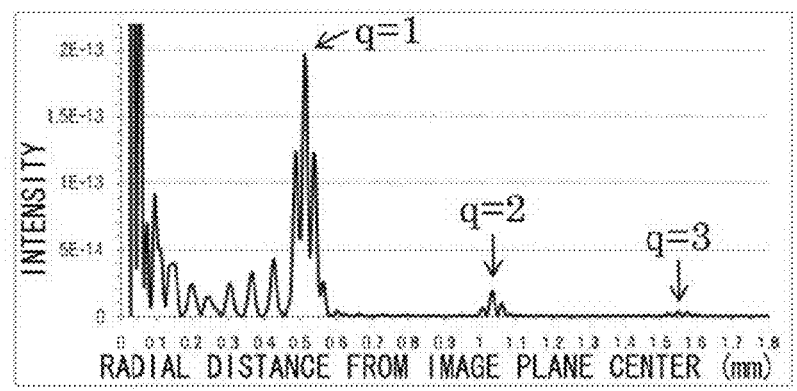
FIG. 61A is a simulation result of the image plane intensity distribution at the focal point position of 0th order diffracted light of the comparative example shown in FIG. 58B
Figure 61B:
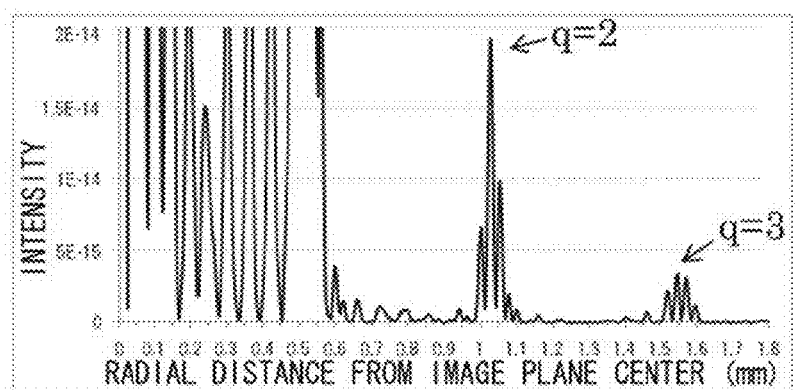
FIG. 61B is an enlarged view of a principle part of FIG. 61A.

FIG. 60 shows intensity distribution on the optical axis of the comparative example, which is a result of calculations for the 1st to 6th zones conducted to show intensity distribution assuming a range of pupil diameters corresponding to the standard illuminance during daytime. Since such focal point formation region is designed with a high addition power at 4 Diopter, the focal point position for near vision appears at a position closer to the lens. A lens with such a structure is useful as an intraocular lens to be implanted in patients who have their crystalline lens removed by a cataract surgery, for example, and thus with no power of accommodation. As shown in FIGS. 61A and 61B that represent intensity distribution on the 0th order focal point image plane of the comparative example, peaks deriving from the equal-pitch region are formed as side-bands even in such focal point formation region.

Meanwhile, as can be seen by comparing FIGS. 59A and 59B of the present embodiment with FIGS. 61A and 61B of the comparative example, the intensity of each side-band peak (q=1, 2, 3 . . . etc.) deriving from the focal point formation region is reduced by setting the cancellation region in the present embodiment. It can be understood that the method of inverting the positive and negative signs of the blaze as described above works as an effective cancellation method also in the focal point formation region where a high addition power is set.

Twelfth Embodiment

Figure 62:
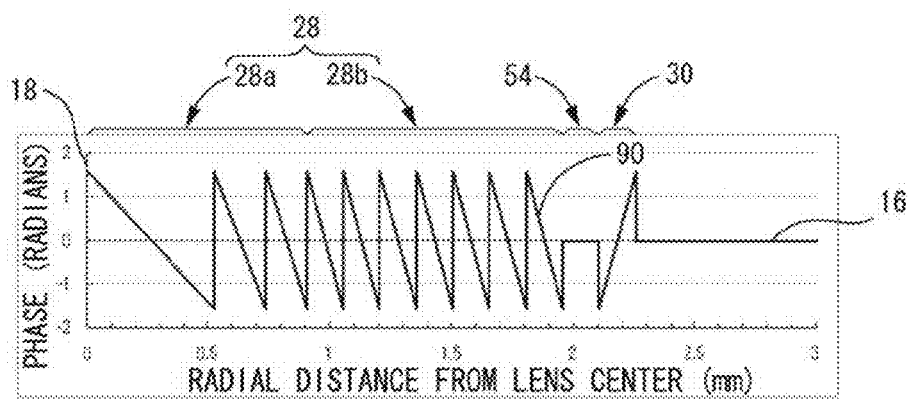
FIG. 62 is a phase profile of a twelfth embodiment of the present invention.
Figure 63A:
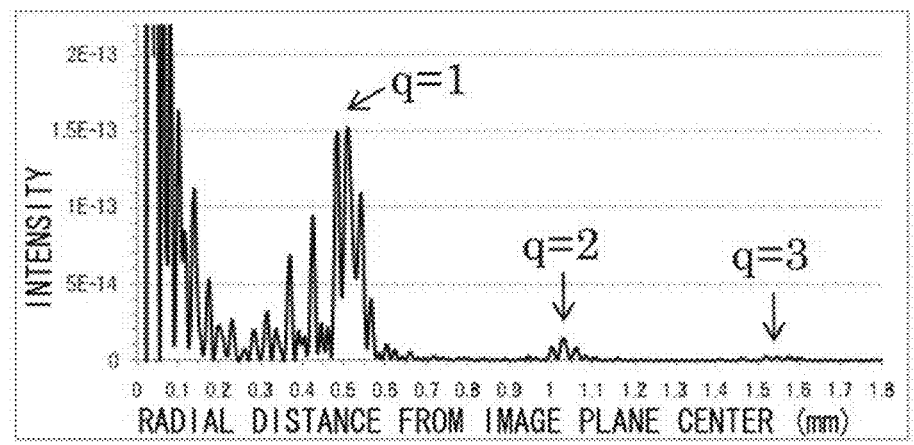
FIG. 63A shows simulation results of the image plane intensity distribution at the focal point position of 0th order diffracted light of the present embodiment and FIG. 63B is an enlarged view of a principle part of FIG. 63A.
Figure 63B:
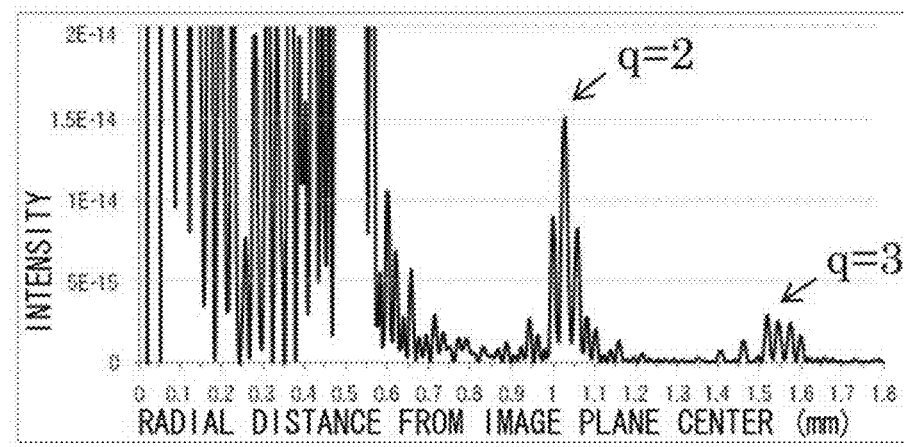

A twelfth embodiment is an example wherein the cancellation region 30 is set against the focal point formation region 28 via the refraction region 54. Table 15 and FIG. 62 show a phase profile 90 of the present embodiment. The focal point formation region of the present embodiment is the same as the one of the eleventh embodiment in which the interval of zone adjacent to the focal point formation region 28 is made equal to pitch of the equal-pitch region 28b and the phase constant is set at h=0 so as to constitute the refraction region 54 (11th zone in Table 15). Then, on its outside, the cancellation region 30 (12th zone in Table 15) is provided with the same interval and the phase constant at h=−0.5. FIGS. 63A and 63B show intensity distribution on the 0th order focal point image plane of the present embodiment.

TABLE 15

[Twelfth embodiment]

| Region | Zone No. | $r_n$ (mm) | $r_{n-1}$ (mm) | $\phi_n$ (radian) | $\phi_{n-1}$ (radian) | Phase constant h |
|---|---|---|---|---|---|---|
| Focal point formation region | 1 | 0.522494 | 0 | −1.57079 | 1.57079 | 0.5 |
| | 2 | 0.738918 | 0.522494 | −1.57079 | 1.57079 | 0.5 |
| | 3 | 0.904986 | 0.738918 | −1.57079 | 1.57079 | 0.5 |
| | 4 | 1.054986 | 0.904986 | −1.57079 | 1.57079 | 0.5 |
| | 5 | 1.204986 | 1.054986 | −1.57079 | 1.57079 | 0.5 |
| | 6 | 1.354986 | 1.204986 | −1.57079 | 1.57079 | 0.5 |
| | 7 | 1.504986 | 1.354986 | −1.57079 | 1.57079 | 0.5 |
| | 8 | 1.654986 | 1.504986 | −1.57079 | 1.57079 | 0.5 |
| | 9 | 1.804986 | 1.654986 | −1.57079 | 1.57079 | 0.5 |
| | 10 | 1.954986 | 1.804986 | −1.57079 | 1.57079 | 0.5 |
| | 11 | 2.104986 | 1.954986 | 0 | 0 | 0 |
| Cancellation region | 12 | 2.254986 | 2.104986 | 1.57079 | −1.57079 | −0.5 |

Even in the present embodiment, it is observed that intensity of the group of side-band peaks (q=1, 2, 3 . . . etc.) is further reduced from that of the comparative example (FIGS. 61A, 61B) described above to exert the cancellation effect. The cancellation effect with the interposition of such refraction region 54 is known to work effectively in the method of setting the phase shift τ described above. The method of reversing the inclination of the blaze is also found to be effective as much.

Thirteenth Embodiment

The method of providing the cancellation region wherein the inclination of the blaze is reversed can be used together with another cancellation method. As an example of such a combined method, a thirteenth embodiment is described below.

Figure 64A:
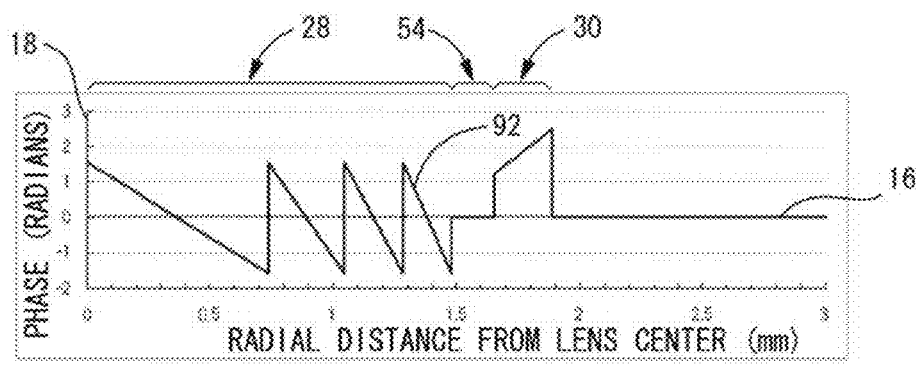
FIG. 64A is a phase profile of a thirteenth embodiment of the present invention and FIG. 64B is a phase profile of a comparative example.
Figure 64B:
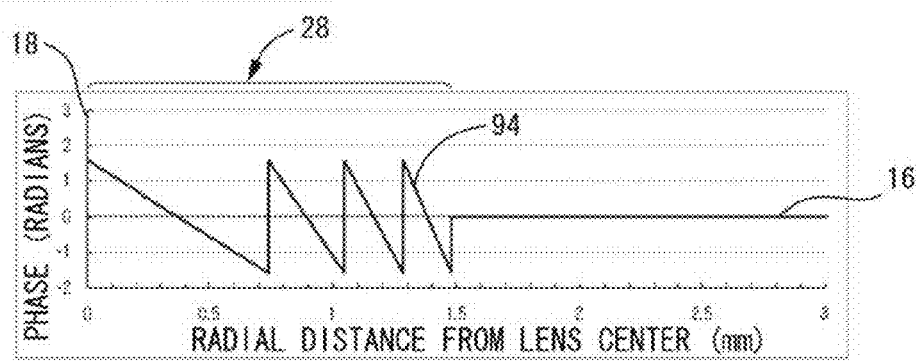
Figure 65:
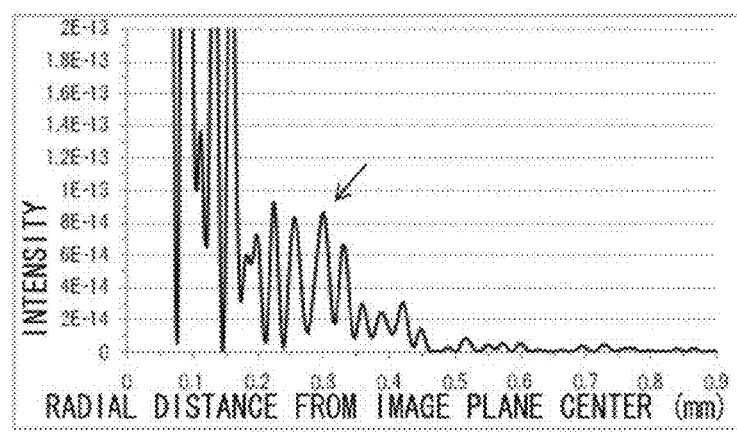
FIG. 65 shows simulation results of the image plane intensity distribution at the focal point position of 0th order diffracted light of the present embodiment.

Table 16 and FIG. 64A show a phase profile 92 of the present embodiment. The focal point formation region 28 of the present embodiment has the 1st to 4th zones composed of Fresnel-pitch zones with the addition power at 2 Diopter. FIG. 64B shows a phase profile 94 of such focal point formation region 28 as a comparative example. Also, FIG. 65 shows intensity distribution of the 0th order focal point image plane of the present embodiment, and FIG. 66 shows a comparative example thereof on the same plane.

Figure 66:
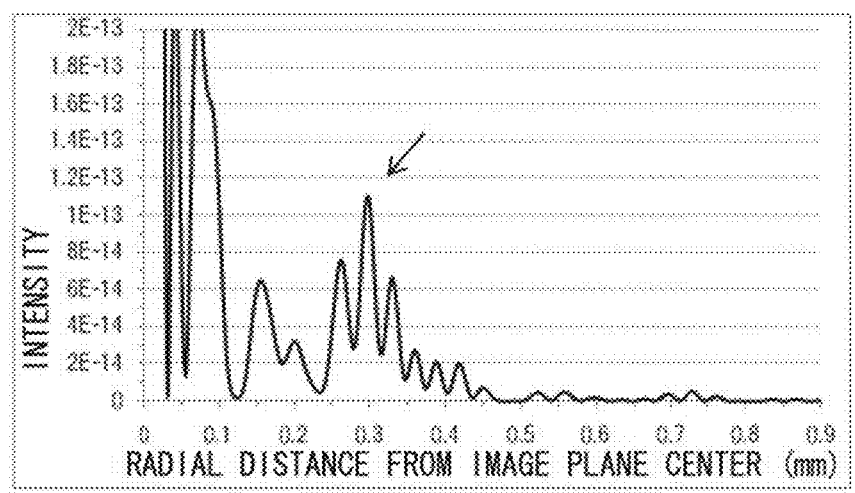
FIG. 66 is a simulation result of the image plane intensity distribution at the focal point position of 0th order diffracted light of the comparative example shown in FIG. 64B.

The comparative example shows a side-band distribution with a peak standing out at around ρ=0.3 mm (an arrow in FIG. 66). In order to reduce such peak intensity, the present embodiment sets the phase constant of the blaze in the zone interposed by the refraction region 54 at h=−0.2 and the phase shift at τ=0.6π. Such a phase profile has a configuration where the blaze with reversed inclination is lifted up in the positive direction on the coordinate axis due to the phase shift. Intensity distribution of the 0th order focal point image plane of the present embodiment (FIG. 65) indicates the stand-out peak observed in the comparative example (marked by an arrow) is now reduced. Thus, the cancellation effect can be achieved by combining the other cancellation method described above with the method of reversing the blaze inclination.

Fourteenth Embodiment

Figure 67:
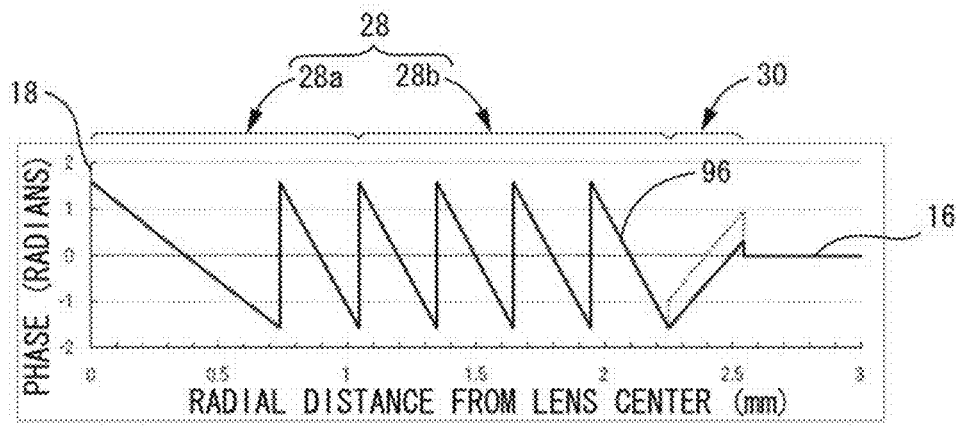
FIG. 67 is a phase profile of a fourteenth embodiment of the present invention.
Figure 68A:
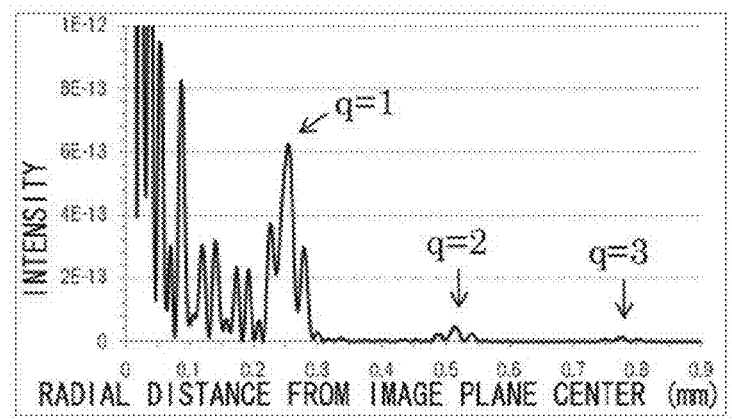
FIG. 68A shows simulation results of the image plane intensity distribution at the focal point position of 0th order diffracted light of the present embodiment and FIG. 68B is an enlarged view of a principle part of FIG. 68A.
Figure 68B:
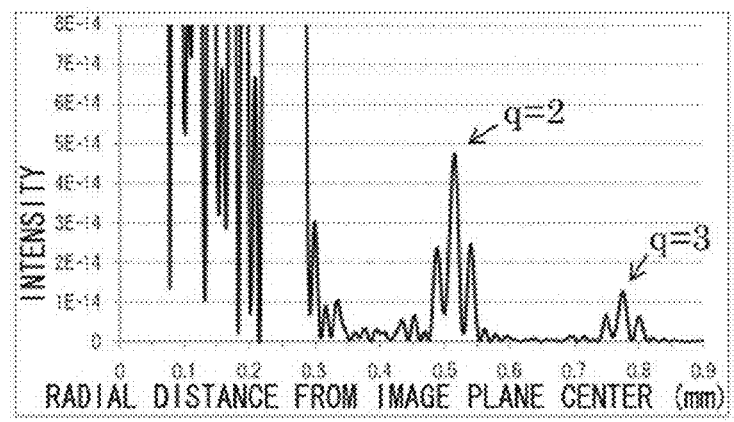

A fourteenth embodiment is another aspect of the tenth embodiment described above with a phase shift additionally set in the cancellation region 30. More specifically, it is the one where a phase shift at τ=−0.2π is additionally set in the cancellation region 30 of another aspect of the tenth embodiment. Table 17 and FIG. 67 show a phase profile 96 of the present embodiment. As evident from FIG. 67, due to such an additional setting of the phase shift, the blaze drops down from the position with no phase shift (dotted line in the figure) to align with the edge of the blaze of the inner adjacent zone (6th zone). FIGS. 68A and 68B show intensity distribution of the 0th order focal point image plane of the present embodiment. The reduction ratios of the side-bands (q=1, 2, 3 . . . etc.) are almost the same as those of the other aspect of the tenth embodiment (FIGS. 55A, 55B), which indicates the cancellation effect is maintained.

TABLE 16

[Thirteenth embodiment]

| Region | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|
| Focal point formation region | 1 | 0.738918 | 0 | −1.57079 | 1.57079 | 0.5 | 0 |
| | 2 | 1.044988 | 0.738918 | −1.57079 | 1.57079 | 0.5 | 0 |
| | 3 | 1.279844 | 1.044988 | −1.57079 | 1.57079 | 0.5 | 0 |
| | 4 | 1.477836 | 1.279844 | −1.57079 | 1.57079 | 0.5 | 0 |
| Refraction region | 5 | 1.652271 | 1.477836 | 0 | 0 | 0 | 0 |
| Cancellation region | 6 | 1.887126 | 1.652271 | 2.51327 | 1.25663 | −0.2 | 0.6π |

TABLE 17

[Seventeenth embodiment]

| Region | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|
| Focal point formation region | 1 | 0.738918 | 0 | −1.57079 | 1.57079 | 0.5 | 0 |
| | 2 | 1.044988 | 0.738918 | −1.57079 | 1.57079 | 0.5 | 0 |
| | 3 | 1.344988 | 1.044988 | −1.57079 | 1.57079 | 0.5 | 0 |
| | 4 | 1.644988 | 1.344988 | −1.57079 | 1.57079 | 0.5 | 0 |
| | 5 | 1.944988 | 1.644988 | −1.57079 | 1.57079 | 0.5 | 0 |
| | 6 | 2.244988 | 1.944988 | −1.57079 | 1.57079 | 0.5 | 0 |
| Cancellation region | 7 | 2.544988 | 2.244988 | 0.31415 | −1.57079 | −0.3 | −0.2π |

The present embodiment makes it easier to actually manufacture a diffraction-type lens with a relief structure by means of additionally setting a phase shift and eliminating level differences between adjacent zones as opposed to reversing the blaze inclination. Such a combinational use of phase shift can contribute to improving the workability of the relief configuration of the lens while maintaining the cancellation effect.

Fifteenth Embodiment

The cancellation region can be configured as composed of multiple zones with the blaze inclination reversed. As an example of using multiple blazes with the inclination reversed to make a cancellation region, a fifteenth embodiment is described below.

Figure 69:
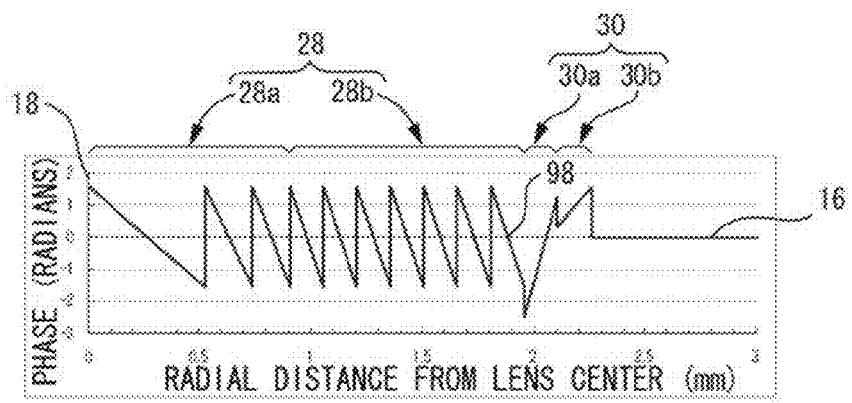
FIG. 69 is a phase profile of a fifteenth embodiment of the present invention.

Table 18 and FIG. 69 show a phase profile 98 of the present embodiment. The present embodiment is based on the eleventh embodiment described above, wherein two zones (30a, 30b) with the same interval as that of the equal-pitch region 28b are set adjacent to the focal point formation region 28 of the eleventh embodiment (FIG. 58A) while a phase constant is set at h=−0.6 and phase shift at τ=−0.2π in the 11th zone (30a), whereas a phase constant is set at h=−0.2 and phase shift at τ=0.3π in the 12th zone (30b) as shown in Table 18 to make the cancellation region 30.

TABLE 18

[Fifteenth embodiment]

| Region | Zone No. | $r_n$ (mm) | $r_{n-1}$ (mm) | $\phi_n$ (radian) | $\phi_{n-1}$ (radian) | Phase constant h | Phase shift τ (radian) |
|---|---|---|---|---|---|---|---|
| Focal point formation region | 1 | 0.522494 | 0 | −1.57079 | 1.57079 | 0.5 | 0 |
| | 2 | 0.738918 | 0.522494 | −1.57079 | 1.57079 | 0.5 | 0 |
| | 3 | 0.904986 | 0.738918 | −1.57079 | 1.57079 | 0.5 | 0 |
| | 4 | 1.054986 | 0.904986 | −1.57079 | 1.57079 | 0.5 | 0 |
| | 5 | 1.204986 | 1.054986 | −1.57079 | 1.57079 | 0.5 | 0 |
| | 6 | 1.354986 | 1.204986 | −1.57079 | 1.57079 | 0.5 | 0 |
| | 7 | 1.504986 | 1.354986 | −1.57079 | 1.57079 | 0.5 | 0 |
| | 8 | 1.654986 | 1.504986 | −1.57079 | 1.57079 | 0.5 | 0 |
| | 9 | 1.804986 | 1.654986 | −1.57079 | 1.57079 | 0.5 | 0 |
| | 10 | 1.954986 | 1.804986 | −1.57079 | 1.57079 | 0.5 | 0 |
| Cancellation region | 11 | 2.104986 | 1.954986 | 1.25663 | −2.51327 | −0.6 | −0.2π |
| | 12 | 2.254986 | 2.104986 | 1.57079 | 0.31415 | −0.2 | 0.3π |

Figure 70A:
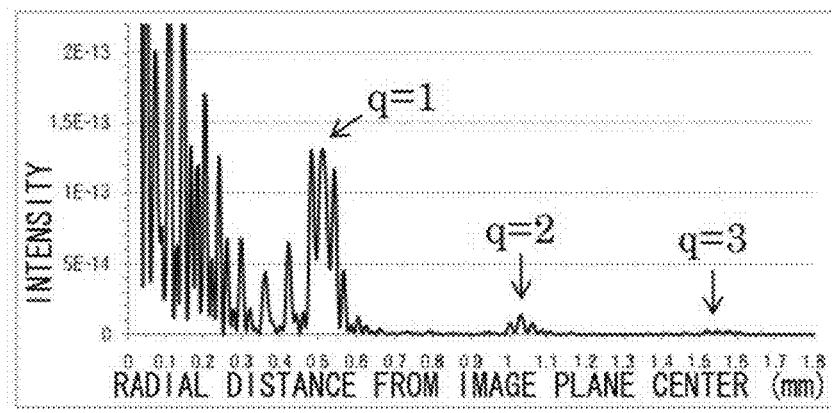
FIG. 70A shows simulation results of the image plane intensity distribution at the focal point position of 0th order diffracted light of the present embodiment and FIG. 70B is an enlarged view of a principle part of FIG. 70A.
Figure 70B:
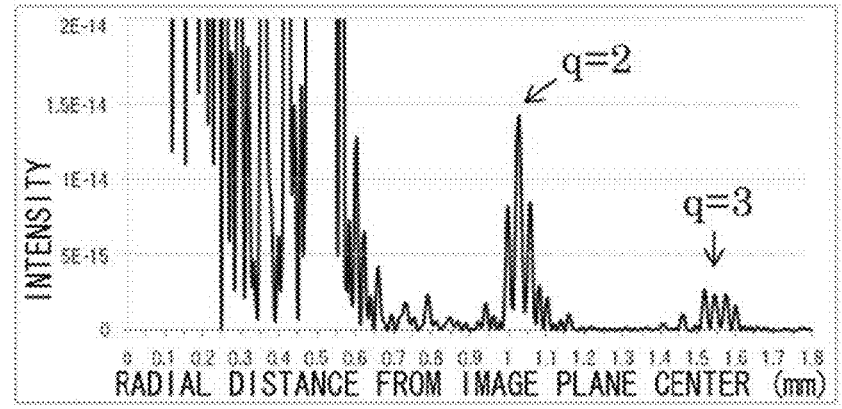

FIGS. 70A and 70B show intensity distribution of the 0th order focal point image plane of the present embodiment. Comparing it with the comparative example described above (FIG. 61A, 61B) as the focal point formation region 28, it is observed that the intensity of the group of side-band peaks (q=1, 2, 3 ... etc.) is reduced in the present embodiment, too. Also, a comparison with the eleventh and twelfth embodiments reveals that the reduction ratios of the peaks at q=2 and q=3 are at the same level, but as far as the peak at q=1 is concerned, the peak intensity has further decreased from that of the embodiments by about 10%.

Thus, it is possible to provide the cancellation region using multiple blazes, and also by additionally using the phase shift τ to be combined and adjusted with other methods of the present invention.

Also, the focal point formation region 28 and the cancellation region 30 referred to in such examples described above can be installed separately on either side of the front and back surfaces of the intended ophthalmic lens or can be installed together on the same surface thereof.

The ophthalmic lens of the present invention specifically includes a contact lens, glasses, and an intraocular lens. In addition, a corneal inlay lens that is planted into the corneal stroma to correct the vision or an artificial cornea can also be adopted. Also, for contact lenses, the present invention can be favorably applied to an oxygen-permeable hard contact lens, an aqueous or non-aqueous soft contact lens, or even an aqueous or non-aqueous oxygen-permeable soft contact lens containing silicone ingredients. As to intraocular lenses, it can also be used favorably for any of them including a hard-type intraocular lens or a soft-type intraocular lens that can be inserted into the eye in folding.

The concept and analytical means of the present invention are not particularly limited to a diffraction-type multifocal ophthalmic lens but are also applicable to a refraction-type multifocal ophthalmic lens. For example, in a refraction-type multifocal ophthalmic lens having a refractive power whereby a near vision focal point is formed by the front and rear curvature of the lens at the center of the optical part and a far vision focal point is formed by the front and rear curvature of the lens in the peripheral area, or in a refraction-type multifocal ophthalmic lens with the central portion designed for far vision and the peripheral portion for near vision, the halo formation can be caused by light beams for near vision straying into the image plane at the focal point for far vision as is the case with the diffraction-type multifocal ophthalmic lens. Since a refractive-type multifocal ophthalmic lens causes the halo based on the wave-optical mechanism as is the case with a diffraction-type lens, the analytical and design methods for the present invention can be applied to a refractive type lens to reduce the halo formation.

Since there is some possibility that the cancellation region 30 gives an impact on the quality of far and near vision in a photopic or mesopic environment, it is desirable to form the cancellation region 30 in a smaller area on the inner side of the outer periphery of the optical part 12. Also, the focal point formation region 28 is preferably formed in a larger extent than the cancellation region 30 within the area 5 mm or less in diameter of the optical part 12.

Also, it is possible to form a diffraction structure related to the present invention on a laminated body composed of two materials with different refractive indices as described in Japanese Unexamined Patent Publication No. JP-A-2001-042112.

KEYS TO SYMBOLS

10: Ophthalmic lens; 12: Optical part; 14: Optical part front surface; 16: Optical part back surface; 18: Lens central axis; 20: Diffraction structure; 21: Relief; 26, 34, 36, 40, 44, 48, 52, 56, 58, 62, 64, 66, 68, 70, 80, 84, 86, 90, 92, 96, 98: Phase profile; 28: Focal point formation region; 30: Cancellation region; 54: Refraction region; 72: Supplementary cancellation region

The invention claimed is:
1. A multifocal ophthalmic lens comprising:
a focal point formation region provided in an optical part of the lens and configured to give at least two focal points, the focal point formation region being composed of a diffraction structure where a plurality of diffraction zones are formed concentrically, and a first one of the focal points provided by the focal point formation region is a focal point for far vision and a rest of the focal points provided by the focal point formation region includes a focal point for near vision; and
at least one cancellation region being provided in the optical part, the at least one cancellation region being composed of the diffraction structure and produces on an image plane at the first one of the focal points a diffracted light with an amplitude distribution that reduces amplitudes of a light other than the one that forms the first one of the focal points, and the at least one cancellation region being disposed on an outside of a diffraction zone of the focal point formation region that gives the focal point for far vision,
wherein an amplitude distribution $A(\rho)$ for reducing the amplitude on the image plane at the first focal point by the light other than the one that forms the first focal point is given by a phase function $\phi_c(r)$ for modulating a light phase provided in the cancellation region which is expressed by Equation 2 below using the phase function $\phi_c(r)$:

$$A(\rho) = E_0 \exp\left[i\left(kf + \frac{k\rho^2}{2f}\right)\right] \times \int_{r_{n-1}}^{r_n} \left[\exp\{i\phi_C(r)\} \times \exp\left\{-i\frac{k\rho}{f} \times r\right\}\right] dr \quad \text{[Equation 2]}$$

$E_0$: Intrinsic amplitude
k: Wavenumber, defined by $k=2\pi/\lambda$ where $\lambda$ is wavelength
f: Focal length of the first focal point
$\rho$: Position in a radial direction measured from the center of image plane at the first focal point position
$r_{n-1}$: Inner radius of the cancellation region
$r_n$: Outer radius of the cancellation region
$\phi_c(r)$: Phase function of the cancellation region
r: Position measured from a lens center in the radial direction, and
the phase function $\phi_c(r)$ of the cancellation region is determined by Equation 3 below:

$$\phi_C(r) = \sum_{i=1}^{j}\left[a_i \times \sin\left\{\alpha_i\pi \times \left(\frac{r-r_{n-1}}{r_n - r_{n-1}}\right)^{s_i} + \beta_i\right\} + a_i' \times \cos\left\{\alpha_i'\pi \times \left(\frac{r-r_{n-1}}{r_n - r_{n-1}}\right)^{s_i'} + \beta_i'\right\}\right] + \tau \quad \text{[Equation 3]}$$

$a_i$, $a_i'$, $\alpha_i$, $\alpha_i'$, $\beta_i$, $\beta_i'$: Constant
$s_i$, $s_i'$: Exponent, real number other than 0
$r_n$: Outer radius of the cancellation region
$r_{n-1}$: Inner radius of the cancellation region
$\tau$: Phase shift (radian)
r: Position measured from the lens center in the radial direction.

2. The multifocal ophthalmic lens according to claim 1, wherein the focal point formation region is formed in an inner peripheral portion of the optical part, while the cancellation region is formed in an outer peripheral portion of the optical part.

3. The multifocal ophthalmic lens according to claim 2, wherein an inner diameter of a formation area of the cancellation region is made larger than a pupil diameter of a human eye under bright conditions, and an outer diameter of the formation area of the cancellation region is made smaller than the pupil diameter of the human eye under dark conditions.

4. The multifocal ophthalmic lens according to claim 2, wherein the inner diameter of the formation area of the cancellation region is set at 2-6 mm, while the outer diameter of the formation area of the cancellation region is set at 3-8 mm.

5. The multifocal ophthalmic lens according to claim 1, wherein the focal point formation region is made larger than the cancellation region within an area 5 mm or less in diameter of the optical part.

6. The multifocal ophthalmic lens according to claim 1, wherein the first focal point is given by a 0th order diffracted light from the diffraction structure while a rest of the focal points is given by a first-order diffracted light from the diffraction structure.

7. The multifocal ophthalmic lens according to claim 6, wherein at least two focal points formed by the diffraction structure of the focal point formation region are given by the diffraction zones characterized by a phase function for modulating a light phase.

8. The multifocal ophthalmic lens according to claim 7, wherein a part or whole of the phase function of the diffraction zones in the diffraction structure of the focal point formation region is composed of a blaze-like function.

9. The multifocal ophthalmic lens according to claim 6, wherein the diffraction structure of the focal point formation region includes zones having an outer radius of Fresnel pitch determined by Equation 1 below:

$$r_n = \sqrt{\frac{\{2(n-1)+g\} \times \lambda}{P_{add}}} \quad \text{[Equation 1]}$$

n: Zone number $$g = \frac{P_{add} \times r_1^2}{\lambda}$$

$\lambda$: Wavelength $P_{add}$: Addition power in setting the focal point of the first-order diffracted light using a focal point position of the 0th order diffracted light as a reference $r_n$: Outer radius of the $n^{th}$ diffraction zone $r_1$: Outer radius of the $1^{st}$ diffraction zone.

10. The multifocal ophthalmic lens according to claim 1, wherein an interval of the cancellation region is made equal to that of one of the diffraction zones of the diffraction structure in the focal point formation region.

11. The multifocal ophthalmic lens according to claim 1, wherein the at least one cancellation region comprises a plurality of cancellation regions arranged in a radial direction of the lens.

12. The multifocal ophthalmic lens according to claim 1, wherein a part or whole of the cancellation region is provided within a maximum outer diameter of the focal point formation region.

13. The multifocal ophthalmic lens according to claim 1, wherein the focal point formation region and the cancellation region are alternately formed in a radial direction of the optical part, and the at least one cancellation region comprises at least two cancellation regions formed in the radial direction of the optical part.

14. The multifocal ophthalmic lens according to claim 1, wherein the first focal point is given by a diffraction structure provided in the focal point formation region, while the diffraction structure in the focal point formation region and a diffraction structure in the cancellation region are both made as a relief structure reflecting an optical path length equivalent to a phase defined by a phase function representing a phase profile of the diffraction structure.

15. The multifocal ophthalmic lens according to claim 1, where a diffraction structure provided in the focal point formation region to form the first focal point and a diffraction structure in the cancellation region are composed of blaze-like diffraction zones formed concentrically to each other, while an inclination of the blaze in the diffraction zone of the diffraction structure in the cancellation region is reversed from that of the blaze in the diffraction zone in the focal point formation region.

16. The multifocal ophthalmic lens according to claim 15, wherein a phase shift is set up for the diffraction zone in which the inclination of the blaze is reversed in the cancellation region.

17. The multifocal ophthalmic lens according to claim 1, wherein a diffraction structure provided in the focal point formation region to form the first focal point and a diffraction structure in the cancellation region are composed of diffraction zones formed concentrically to each other, while a refraction region provided with a refracting interface is formed between the diffraction zone in the focal point formation region and the diffraction zone in the cancellation region.

18. The multifocal ophthalmic lens according to claim 1, wherein a diffraction structure provided in the focal point formation region to form the first focal point and a diffraction structure in the cancellation region are each composed of a relief structure, while the relief structure in each of the focal point formation region and the cancellation region is formed on one of front and back surfaces of the optical part of the lens.

19. The multifocal ophthalmic lens according to claim 1, wherein the multifocal ophthalmic lens is a multifocal contact lens.

20. A multifocal ophthalmic lens comprising:
a focal point formation region provided in an optical part of the lens and configured to give at least two focal points, the focal point formation region being composed of a diffraction structure where a plurality of diffraction zones are formed concentrically, and a first one of the focal points is given by a 0th order diffracted light from the diffraction structure while a rest of the focal points is given by a first-order diffracted light from the diffraction structure; and
at least one cancellation region being provided in the optical part, the at least one cancellation region produces on an image plane at the first one of the focal points a diffracted light with an amplitude distribution that reduces amplitudes of a light other than the one that forms the first one of the focal points,
wherein the diffraction structure of the focal point formation region has a periodic structure with equal pitches, and
an amplitude distribution $A(\rho)$ for reducing the amplitude on the image plane at the first focal point by the light other than the one that forms the first focal point is given by a phase function $\phi_c(r)$ for modulating a light phase provided in the cancellation region which is expressed by Equation 2 below using the phase function $\phi_c(r)$:

$$A(\rho) = E_0 \exp\left[i\left(kf + \frac{k\rho^2}{2f}\right)\right] \times \int_{r_{n-1}}^{r_n}\left[\exp\{i\phi_C(r)\} \times \exp\left\{-i\frac{k\rho}{f} \times r\right\}\right]dr \quad \text{[Equation 2]}$$

$E_0$: Intrinsic amplitude k: Wavenumber, defined by $k=2\pi/\lambda$ where $\lambda$ is wavelength f: Focal length of the first focal point $\rho$: Position in a radial direction measured from the center of image plane at the first focal point position $r_{n-1}$: Inner radius of the cancellation region $r_n$: Outer radius of the cancellation region $\phi_c(r)$: Phase function of the cancellation region r: Position measured from a lens center in the radial direction, and the phase function $\phi_c(r)$ of the cancellation region is determined by Equation 3 below:

$$\phi_c(r) = \sum_{i=1}^{j}\left[a_i \times \sin\left\{\alpha_i\pi \times \left(\frac{r-r_{n-1}}{r_n-r_{n-1}}\right)^{s_i} + \beta_i\right\} + a'_i \times \cos\left\{\alpha'_i\pi \times \left(\frac{r-r_{n-1}}{r_n-r_{n-1}}\right)^{s'_i} + \beta'_i\right\}\right] + \tau \quad \text{[Equation 3]}$$

$a_i, a'_i, \alpha_i, \alpha'_i, \beta_i, \beta'_i$: Constant $s_i, s'_i$: Exponent, real number other than 0

$r_n$: Outer radius of the cancellation region $r_{n-1}$: inner radius of the cancellation region $\tau$: Phase shift (radian)

r: Position measured from the lens center in the radial direction.

21. A multifocal ophthalmic lens comprising:

a focal point formation region provided in an optical part of the lens and configured to give at least two focal points; and at least one cancellation region being provided in the optical part that, on an image plane at a first one of the focal points, produces a diffracted light with an amplitude distribution that reduces amplitudes of a light other than the one that forms the first one of the focal points, wherein an amplitude distribution $A(\rho)$ for reducing the amplitude on the image plane at the first focal point by the light other than the one that forms the first focal point is given by a phase function $\phi_c(r)$ for modulating a light phase provided in the cancellation region which is expressed by Equation 2 below using the phase function $\phi_c(r)$:

$$A(\rho) = E_0\exp\left[i\left(kf + \frac{k\rho^2}{2f}\right)\right] \times \int_{r_{n-1}}^{r_n}\left[\exp\{i\phi_C(r)\} \times \exp\left\{-i\frac{k\rho}{f} \times r\right\}\right]dr \quad \text{[Equation 2]}$$

$E_0$: Intrinsic amplitude k: Wavenumber, defined by $k=2\pi/\lambda$ where $\lambda$ is wavelength f: Focal length of the first focal point $\rho$: Position in a radial direction measured from the center of image plane at the first focal point position $r_{n-1}$: Inner radius of the cancellation region $r_n$: Outer radius of the cancellation region $\phi_c(r)$: Phase function of the cancellation region r: Position measured from a lens center in the radial direction, and the phase function $\phi_c(r)$ of the cancellation region is determined by Equation 3 below:

$$\phi_c(r)=\sum_{i=1}^{i}[a_i \times \sin\{\alpha_i\pi \times (r-r_{n-1}/r_n-r_{n-1})^{s_i}+\beta_i\}+\alpha'_i \times \cos\{\alpha'_i\pi \times (r-r_{n-1}/r_n-r_{n-1})^{s'_i}+\beta'_i\}]+\tau \quad \text{[Equation 3]}$$

$a_i, a'_i, \alpha_i, \alpha'_i, \beta_i, \beta'_i$: Constant $s_i, s'_i$: Exponent, real number other than 0

$r_n$: Outer radius of the cancellation region $r_{n-1}$: Inner radius of the cancellation region $\tau$: Phase shift (radian)

r: Position measured from the lens center in the radial direction.

22. The multifocal ophthalmic lens according to claim 21, wherein the phase function $\phi_c(r)$ is composed of a blaze-like function.

23. The multifocal ophthalmic lens according to claim 22, wherein the blaze-like function is determined by Equation 4 below:

$$\phi_c(r) = \left(\frac{\phi_n - \phi_{n-1}}{r_n - r_{n-1}}\right) \times r + \left(\frac{\phi_{n-1} \times r_n - \phi_n \times r_{n-1}}{r_n - r_{n-1}}\right) + \tau \quad \text{[Equation 4]}$$

$\phi_n$: Phase at a position of the outer radius of the cancellation region $\phi_{n-1}$: Phase at a position of the inner radius of the cancellation region $r_n$: Outer radius of the cancellation region $r_{n-1}$: Inner radius of the cancellation region $\tau$: Phase shift (radian)

r: Position measured from the lens center in the radial direction.

24. The multifocal ophthalmic lens according to claim 21, wherein the phase shift $\tau$ is within a range defined by Equation 5 below:

$$(2m-1.75)\times\pi \leq \tau \leq 2m\pi \ (m: \text{integer}). \quad \text{[Equation 5]}$$

25. The multifocal ophthalmic lens according to claim 24, wherein the phase shift ti is determined by Equation 6 below, $$\tau=(2u-1)\pi \ (u: \text{integer}). \quad \text{[Equation 6]}$$

26. A method of manufacturing a multifocal ophthalmic lens, the method comprising:

forming a focal point formation region provided in an optical part of the lens to give at least two focal points, the focal point formation region being composed of a diffraction structure where a plurality of diffraction zones are formed concentrically, and a first one of the focal points provided by the focal point formation region is a focal point for far vision and a rest of the focal points provided by the focal point formation region includes a focal point for near vision; and disposing a cancellation region on an outside of a diffraction zone of the focal point formation region that gives the focal point for far vision that, on an image plane at a first one of the focal points, is capable of reducing amplitudes of a light other than the one that forms the first focal point by means of a phase function $\phi_c(r)$ of Equation 7 below that expresses an amplitude distribution $A(\rho)$ that reduces the amplitudes of the light other than the one that forms the first focal point on the image plane at the first focal point:

$$A(\rho) = \quad \text{[Equation 7]}$$
$$E_0\exp\left[i\left(kf + \frac{k\rho^2}{2f}\right)\right] \times \int_{r_{n-i}}^{r_n}\left[\exp\{i\phi_C(r)\} \times \exp\left\{-i\frac{k\rho}{f} \times r\right\}\right]dr$$

$E_0$: Intrinsic amplitude k: Wavenumber, defined by $k=2\pi/\lambda$ where $\lambda$ is wavelength f: Focal length of the first focal point $\rho$: Position in a radial direction measured from a center of image plane at the first focal point position $r_{n-1}$: Inner radius of the cancellation region
$r_n$: Outer radius of the cancellation region
$\phi_c(r)$: Phase function of the cancellation region
r: Position measured from a lens center in the radial direction, and the phase function $\phi_c(r)$ of the cancellation region is determined by Equation 8 below:

$$\phi_c(r) = \sum_{i=1}^{j} \left[ a_i \times \sin\left\{\alpha_i \pi \times \left(\frac{r - r_{n-1}}{r_n - r_{n-1}}\right)^{s_i} + \beta_i\right\} + a_i' \times \cos\left\{\alpha_i' \pi \times \left(\frac{r - r_{n-1}}{r_n - r_{n-1}}\right)^{s_i'} + \beta_i'\right\} \right] + \tau \quad \text{[Equation 8]}$$

$a_i$, $a_i'$, $\alpha_i$, $\alpha_i'$, $\beta_i$, $\beta_i'$: Constant
$s_i$, $s_i'$: Exponent, real number other than 0
$r_n$: Outer radius of the cancellation region
$r_{n-1}$: Inner radius of the cancellation region
$\tau$: Phase shift (radian)
r: Position measured from the lens center in the radial direction.

27. The method of manufacturing the multifocal ophthalmic lens according to claim 26, wherein the phase function $\phi_c(r)$ of the cancellation region is determined by Equation 9 below:

$$\phi_c(r) = \left(\frac{\phi_n - \phi_{n-1}}{r_n - r_{n-1}}\right) \times r + \left(\frac{\phi_{n-1} \times r_n - \phi_n \times r_{n-1}}{r_n - r_{n-1}}\right) + \tau \quad \text{[Equation 9]}$$

$\phi_n$: Phase at a position of the outer radius of the cancellation region
$\phi_{n-1}$: Phase at a position of the inner radius of the cancellation region
$r_n$: Outer radius of the cancellation region
$r_{n-1}$: Inner radius of the cancellation region
$\tau$: Phase shift (radian)
r: Position measured from the lens center in the radial direction.

* * * * *